(12) United States Patent
Pinney et al.

(10) Patent No.: US 10,807,932 B2
(45) Date of Patent: Oct. 20, 2020

(54) BENZOSUBERENE ANALOGUES AND RELATED COMPOUNDS WITH ACTIVITY AS ANTICANCER AGENTS

(71) Applicant: Baylor University, Waco, TX (US)

(72) Inventors: Kevin G. Pinney, Waco, TX (US); Haichan Niu, Waco, TX (US); Deboprosad Mondal, Waco, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 0 days.

(21) Appl. No.: 16/542,869

(22) Filed: Aug. 16, 2019

(65) Prior Publication Data

US 2020/0055805 A1 Feb. 20, 2020

Related U.S. Application Data

(60) Provisional application No. 62/719,362, filed on Aug. 17, 2018.

(51) Int. Cl.
*C07C 43/23* (2006.01)
*C07C 49/755* (2006.01)
*A61P 35/00* (2006.01)

(52) U.S. Cl.
CPC .............. *C07C 43/23* (2013.01); *A61P 35/00* (2018.01); *C07C 49/755* (2013.01)

(58) Field of Classification Search
CPC ......... C07C 43/23; C07C 49/755; A61P 35/00
USPC ........................................................ 514/690
See application file for complete search history.

(56) References Cited

PUBLICATIONS

Herdman et al., Structural interrogation of benzosuberene-based inhibitors of tubulin polymerization, 2015, Bioorganic & Medicinal Chemistry, 23, 7497-7520 (Year: 2015).*

* cited by examiner

*Primary Examiner* — Kristin A Vajda
(74) *Attorney, Agent, or Firm* — Jackson Walker LLP

(57) ABSTRACT

A series of benzosuberene analogues demonstrate effective inhibition of tubulin polymerization, cytotoxicity against human cancer cell lines, and vascular disruption in tumors.

11 Claims, 11 Drawing Sheets

9   R = CH₃                              n = 1       34   R₁ = CH₃,    R₂ = Br,   R₃ = H          23   R₄ = H
20  R = (CH₂)₃CH₃                        n = 1       33   R₁ = OH,     R₂ = Br,   R₃ = H          35   R₄ = OH
28  R = O(CH₂)₂O(CH₂)₂OCH₃               n = 1       57   R₁ = OCH₃,   R₂ = H,    R₃ = OH         24   R₄ = (=O)
31  R = O(CH₂)₂OH                        n = 1       69   R₁ = OH,     R₂ = H,    R₃ = NHAc
47  R = COOEt                            n = 1
48  R = CH₂OH                            n = 1
38  R = CN                               n = 1
46  R = CHO                              n = 1
39  R = CN                               n = 0

88   R₅ = H                                          76                                            77
89   R₅ = PO(ONa)₂

91                                                   93

Scheme 1 Synthesis of 9

Scheme 2 Synthesis of 20

Scheme 3 Synthesis of 23, 24, 28, 31, 33, 34, 35

Scheme 4 Synthesis of 38, 39, 40

Scheme 5 Synthesis of 47, 48

Scheme 6 Synthesis of 57, 69

Scheme 7 Synthesis of 76, 77

Scheme 8 Synthesis of 88, 89

Scheme 9 Synthesis of 91, 93

BENZOSUBERENE ANALOGUES AND RELATED COMPOUNDS WITH ACTIVITY AS ANTICANCER AGENTS

This application claims priority to U.S. Provisional Patent Application Ser. No. 62/719,362, entitled "Benzosuberene Analogues and Related Compounds with Activity as Anticancer Agents," filed Aug. 17, 2018, the entire contents of which are hereby incorporated by reference.

BACKGROUND

The present disclosure relates to potent small-molecule inhibitors of tubulin polymerization and uses thereof.

Cancer, known medically as a malignant neoplasm, is comprised of a broad group of diseases involving unregulated cell growth. In cancer, cells divide and grow uncontrollably, forming malignant tumors, which may invade both locally and to distal portions of the body. In 2007, cancer was responsible for approximately 13% of all human deaths worldwide (7.9 million). Incidence rates are rising as more people live longer and as lifestyle changes occur in the developing world. There remains an urgent need for the discovery and development of new anticancer agents.

Solid tumors require a functional vasculature to supply oxygen and nutrients to their cells when they exceed 1 mm$^3$ in size. Unlike normal vasculature, the tumor-associated vascular network tends to expand irregularly, incorporating fragile and chaotic bulges and blind ends. The primitive character and inherent fragility of tumor-associated vasculature, along with the seminal observations that blocking established tumor-associated blood flow leads to tumor regression in mice, positioned tumor-associated vasculature as a promising target for cancer therapy. Two categories of small-molecule, vascular-targeted therapies have been developed: angiogenesis inhibiting agents (AIAs) that inhibit neovascularization in developing tumors; and, separately, vascular disrupting agents (VDAs) that irreversibly damage established tumor-associated vasculature. The two major sub-divisions of VDAs include biologics and small-molecule anticancer agents. The majority of small-molecule VDAs function as inhibitors of tubulin polymerization, which destabilize the tubulin-microtubule protein system by binding to the colchicine site on β-tubulin in close proximity to the α,β-tubulin heterodimer interface. The endothelial cells lining microvessels undergo rapid cytoskeletal disruption, manifested by morphological changes (flat to round) in response to inhibition of their tubulin-microtubule protein system cytoskeleton triggered by VDA binding to the colchicine site. This rapid endothelial cell cytoskeletal rearrangement leads to irreversible damage to the tumor-associated vasculature, culminating in tumor necrosis.

SUMMARY

The present disclosure pertains to a series of benzosuberene analogues that serve as small-molecule inhibitors of tubulin polymerization that function both as antiproliferative agents (cytotoxins) and as vascular disrupting agents (VDAs), which cause selective and irreversible damage to tumor-associated vasculature, thereby depriving the tumor of the blood, nutrients, and oxygen it needs to survive.

The natural products colchicine, combretastatin A-4 (CA4), and combretastatin A-1 (CA1), along with the synthetic analogue phenstatin, are potent colchicine site inhibitors of tubulin polymerization that function as promising VDAs. These molecules have provided structural inspiration and guidance for the design, synthesis, and biological evaluation of many second-generation (and beyond) molecules in a world-wide effort to identify a small-molecule colchicine site agent with the necessary efficacy coupled with safety to be utilized as a cancer therapeutic in humans. To date, no small-molecule therapeutic agent that interacts with the colchicine site and functions as either an antiproliferative agent or a VDA (or demonstrates a dual mechanism of action) has reached FDA approval. Structural similarities between these natural products include a trimethoxy phenyl ring, a separate hydroxylated p-methoxy aryl moiety, and a bridging functionality connecting the two rings with a comparable centroid-to-centroid distance. FIG. 1A shows representative small-molecule inhibitors of tubulin polymerization: colchicine, combretastatins (CA4, CA1), phenstatin, dihydronaphthalene analogues (KGP03, KGP05), benzosuberene analogues (KGP18, KGP156), indole analogue (OXi8006), and benzo[b]furan analogue (BNC105). Molecular recognition for the colchicine site has led to the discovery of promising synthetic analogues and derivatives, including stilbenoid, benzo[b]thiophene, benzofuran, dihydronaphthalene, benzosuberene, and indole-based molecules shown in FIG. 1A. Numerous other studies have investigated a myriad of structural and functional group modifications to the A-ring, the B-ring, and the ethylene bridge of combretastatin A-4.

Two benzosuberene-based analogues (referred to as KGP18 and its amino congener KGP156) emerged from studies as molecules with high relevance as potential preclinical candidates due, in part, to their potent inhibition of tubulin polymerization, pronounced cytotoxicity against human cancer cell lines, and promising activity as VDAs. Studies have investigated a variety of functional group modifications on both the fused and pendant aryl rings of tubulin-binding benzosuberene and dihydronaphthalene molecular frameworks. FIG. 1B shows selected KGP18 derivatives as inhibitors of tubulin polymerization with modifications at the C-4 position of the A ring and the C-6, 7, 8 positions of the B ring. Interestingly, a benzosuberene B-ring diene analogue was identified as one of the most potent cytotoxic agents amongst a synthesized series of eleven members, and this same molecule (compound 88 herein) was obtained herein as an unexpected product. It is noteworthy that a new class of benzodiazepines has been reported as inhibitors of tubulin polymerization.

DETAILED DESCRIPTION OF PREFERRED EMBODIMENTS

The present disclosure relates to benzosuberene analogues as inhibitors of tubulin polymerization. In particular, the present disclosure relates to a series of structurally varied analogues using KGP18 and KGP05 as lead compounds and further adopted our methodology to investigate functional group modifications on the A-ring (C-4 position) and the B-ring (C-6, 7, 8, 9 positions), along with regiochemical translocation of the pendant aryl ring (C-ring) in regard to their influence on inhibition of tubulin polymerization and cytotoxicity against several human cancer cell lines.

A variety of functional group modifications have been explored and it has been determined that the C-1 position of these substituted benzosuberene analogues is of special importance in regard to maintaining potent inhibition of tubulin assembly, which was exemplified by molecules incorporating hydroxy, methoxy, and halogen moieties. Motivated by the potent activity of these benzosuberene analogues, an efficient ring-closing metathesis (RCM) approach to achieve the benzosuberene scaffold has been described and other benzosuberene analogues with substitutions at various positions have been developed. However, benzosuberene analogues incorporating carbon chain homologues and other functional groups at the C-1 position, along with modified functionalities on the seven-member ring, have not been previously investigated.

Figure 1A:
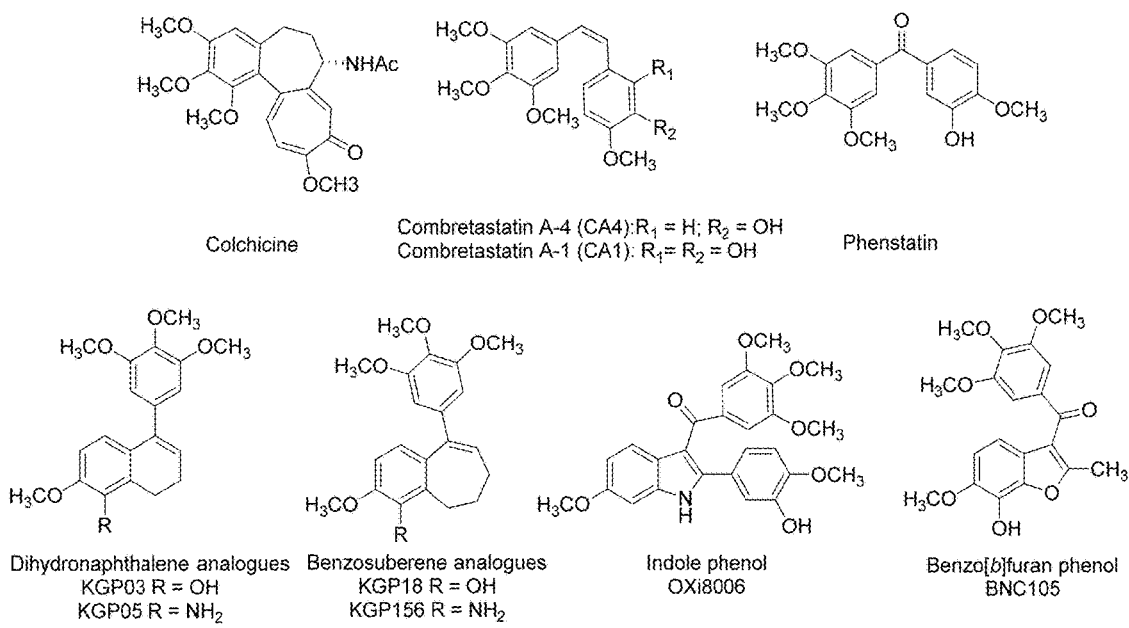
FIG. 1A shows representative small-molecule inhibitors of tubulin polymerization.
Figure 1B:
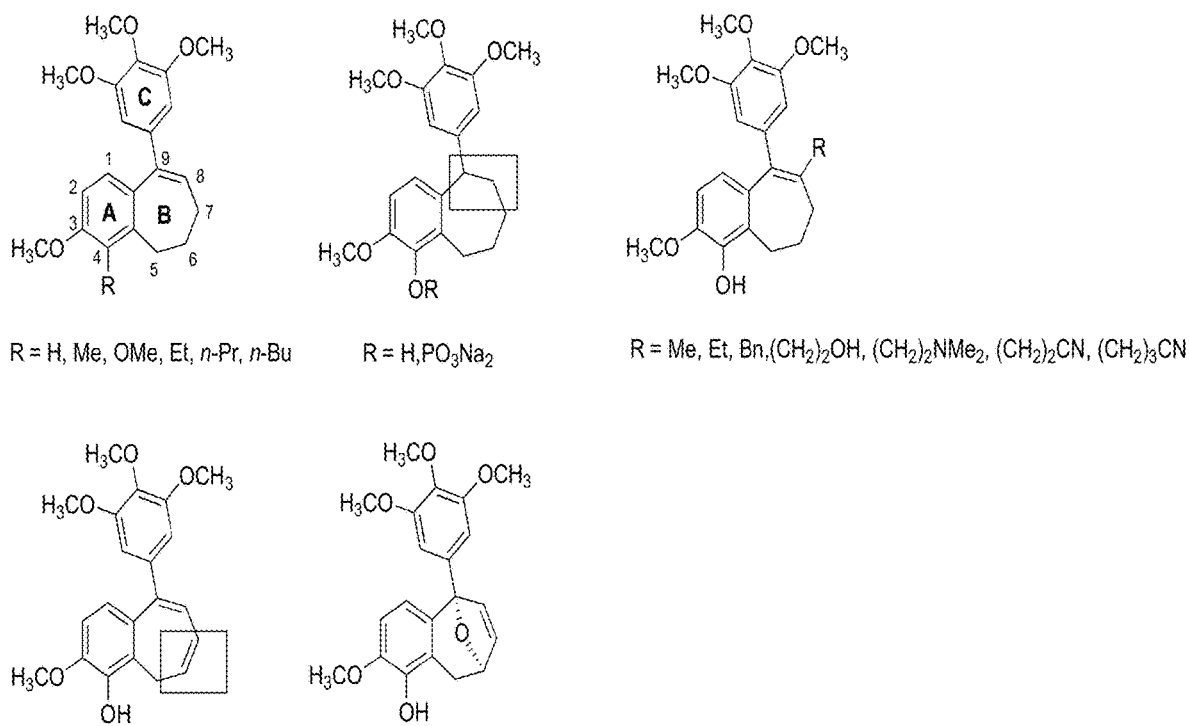
FIG. 1B shows selected KGP18 derivatives as inhibitors of tubulin polymerization.
Figure 2:
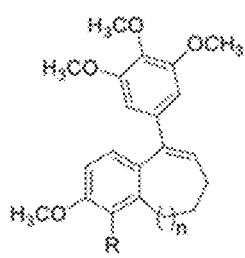
FIG. 2 shows exemplary benzosuberene and dihydronaphthalene analogues in accordance with preferred embodiments described herein.
Figure 2:
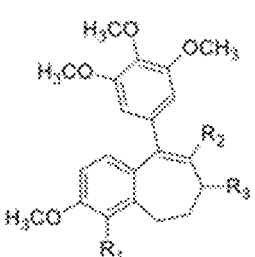
Figure 2:
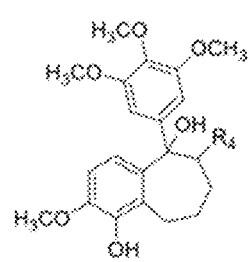
Figure 2:
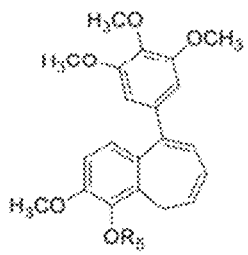
Figure 2:
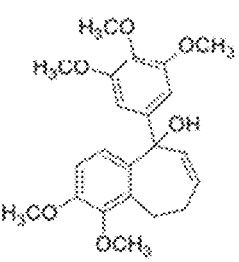
Figure 2:
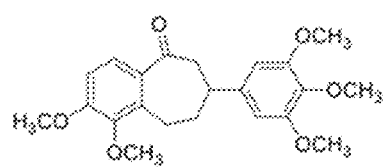
Figure 2:
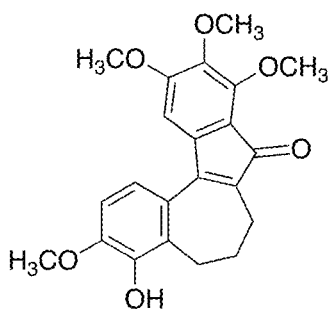
Figure 2:
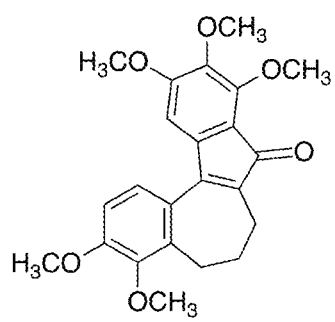

New benzosuberene and dihydronaphthalene analogues depicted in FIG. 2 have been synthesized and investigated for their for their cytotoxicity against selected human cancer cell lines and their ability to inhibit tubulin polymerization.

Preferred embodiments of the benzosuberene and dihydronaphthalene analogues described herein include a compound having the following structure:

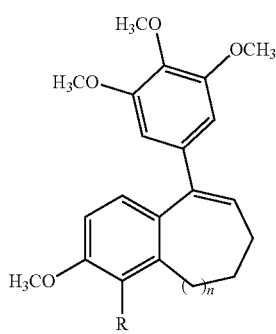

wherein R is $CH_3$, $(CH_2)_3CH_3$, $O(CH_2)_2O(CH_2)_2OCH_3$, $O(CH_2)_2OH$, COOEt, $CH_2OH$, CN, or CHO, and wherein n is 0 or 1. In additional preferred embodiments, when R is CN, n is 0. In additional preferred embodiments, when R is $CH_3$, $(CH_2)_3CH_3$, $O(CH_2)_2O(CH_2)_2OCH_3$, $O(CH_2)_2OH$, COOEt, $CH_2OH$, CN, or CHO, n is 1.

Additional preferred embodiments of the benzosuberene and dihydronaphthalene analogues described herein include a compound having the following structure:

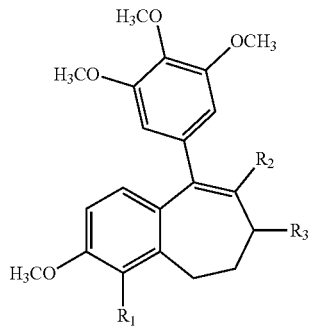

wherein $R_1$ is $CH_3$, OH, $OCH_3$, or OH, $R_2$ is Br or H, and $R_3$ is H, OH, or NHAc. In additional preferred embodiments, $R_1$ is $CH_3$, $R_2$ is Br, and $R_3$ is H. In additional preferred embodiments, $R_1$ is OH, $R_2$ is Br, and $R_3$ is H. In additional preferred embodiments, $R_1$ is $OCH_3$, $R_2$ is H, and $R_3$ is OH. In additional preferred embodiments, $R_1$ is OH, $R_2$ is H, and $R_3$ is NHAc.

Additional preferred embodiments of the benzosuberene and dihydronaphthalene analogues described herein include a compound having the following structure:

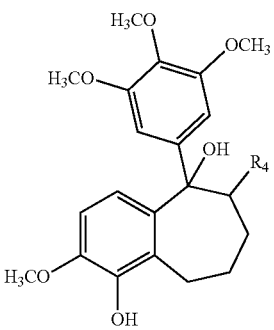

wherein $R_4$ is H, OH, or (=O).

Additional preferred embodiments of the benzosuberene and dihydronaphthalene analogues described herein include a compound having the following structure:

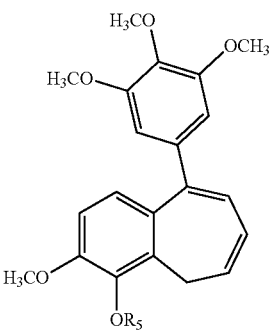

wherein $R_5$ is $PO(ONa)_2$.

Additional preferred embodiments of the benzosuberene and dihydronaphthalene analogues described herein include a compound having one of the following structures:

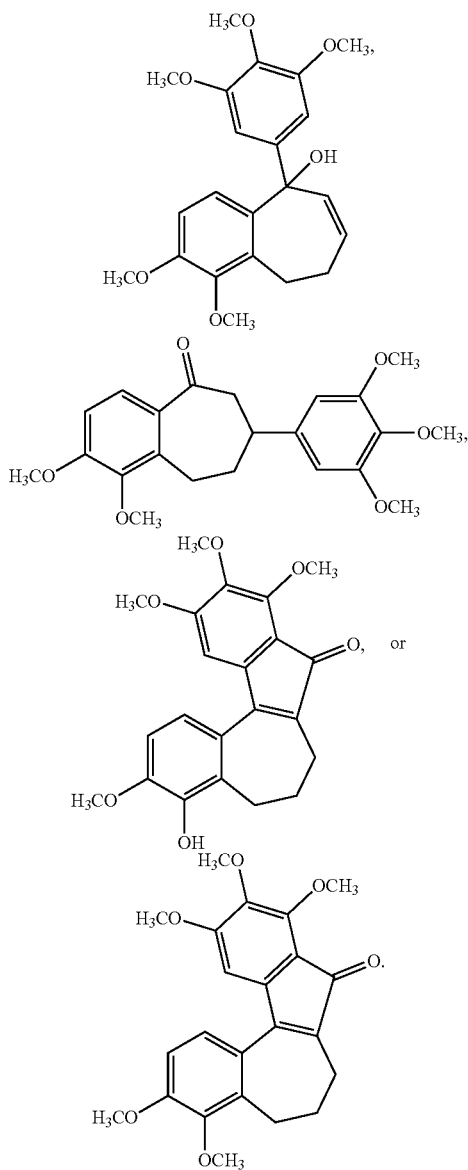

Additional preferred embodiments relate to methods for inhibiting tubulin polymerization, methods for disrupting vascularization, and methods for treating cancer comprising administering preferred embodiments of the benzosuberene analogues described herein to a subject with cancer or with a tumor.

In another aspect of the present invention there is provided a pharmaceutical composition including a therapeutically effective amount of a benzosuberene analogue as defined above and a pharmaceutically acceptable excipient, adjuvant, carrier, buffer or stabiliser. A "therapeutically effective amount" is to be understood as an amount of an exemplary probiotic that is sufficient to show inhibitory effects on tubulin polymerization, vascularization and/or proliferation of tumors or cancerous cells. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilisers, buffers, antioxidants and/or other additives may be included as required.

In another aspect, there is provided the use in the manufacture of a medicament of a therapeutically effective amount of a benzosuberene analogue as defined above for administration to a subject.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

Certain preferred embodiments of the benzosuberene analogues described herein involve chlorosulfonyl isocyanate induced cycloketone formation. Chlorosulfonyl isocyanate (CSI), was first discovered by Graf and co-workers in Germany in the early 1950s and is in liquid form in room temperature, fumes in moist air reacts with water violently, and is incompatible with protic solvents. CSI is probably the most chemically reactive isocyanate species. CSI is a versatile reagent, due in part to the fact that this molecule has two electrophilic sites for nucleophilic reagents attack, namely carbonyl carbon and sulfur of the sulfonyl group, and a cycloaddition can take place at the isocyanate portion. The methodology of synthesizing β-lactams from olefins with CSI was first developed by Graf and co-workers in the 1960s.

Figure 14:
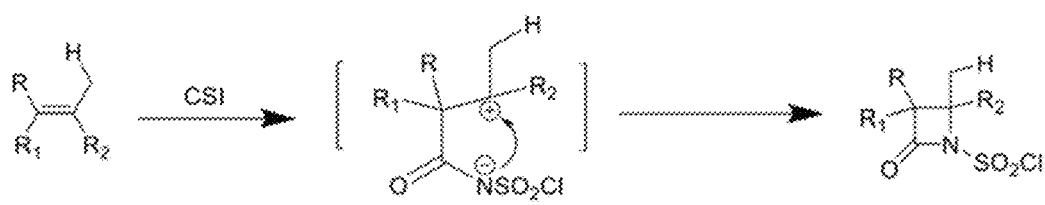
FIG. 14 shows a mechanism of β-lactam formation through chlorosulfonyl isocyanate (CSI).

One of the most common types of CSI reactivity is the addition involving initial attack on the isocyanate carbon. CSI can be attacked by nucleophiles like alcohols (thiols/phenols) and amines, to afford N-chlorosulfonyl carbamates and urea derivatives. In some cases, primary alcohols can be selectively derivatized by CSI without affecting other stereocenters and other groups in complex molecules. FIG. 14 shows the mechanism of β-lactam formation through CSI. For monosubstituted alkenes, this methodology primarily yields the desired β-lactam products. However, for trisubstituted alkenes, different types of reactions might take place, including substitution of the alkene hydrogen or cyclization. Both concerted and nonconcerted 1,4-dipolar mechanisms have been proposed for these reactions. A variety of alkenes that produce β-lactams through [2+2] cycloaddition has been thoroughly studied. However, no cyclized ketone formation with participation of adjacent aryl ring was reported.

Example 1. Synthesis

Tetrahydrofuran (THF), carbon tetrachloride, dichloromethane, methanol, dimethylformamide (DMF), and acetonitrile were used in their anhydrous forms. Reactions were performed under nitrogen gas. Thin-layer chromatography (TLC) plates (precoated glass plates with silica gel 60 F254, 0.25 mm thickness) were used to monitor reactions. Purification of intermediates and products was carried out with a Biotage Isolera flash purification system using silica gel (200-400 mesh, 60 Å) or RP-18 pre-packed columns or manually in glass columns. Intermediates and products synthesized were characterized on the basis of their $^1$H NMR (500 or 600 MHz), $^{13}$C NMR (125 or 150 MHz) spectroscopic data using a Varian VNMRS 500 MHz or Bruker DPX 600 MHz instrument. Spectra were recorded in CDCl$_3$, D$_2$O, (CD$_3$)$_2$CO, or CD$_3$OD. All chemicals shifts are expressed in ppm (δ), and peak patterns are reported as broad (br), singlet (s), doublet (d), triplet (t), quartet (q), pentet (p), sextet (sext), septet (sept), double doublet (dd), double double doublet (ddd), and multiplet (m).

Purity of the final compounds was further analyzed at 25° C. using an Agilent 1200 HPLC system with a diode-array detector (λ=190-400 nm), a Zorbax XDB-C18 HPLC column (4.6 mm Å~150 mm, 5 μm), and a Zorbax reliance cartridge guard-column; Method: solvent A, acetonitrile, solvent B, H$_2$O; gradient, 10% A/90% B to 100% A/0% B over 0 to 40 min; post-time 10 min; flow rate 1.0 mL/min; injection volume 20 μL; monitored at wavelengths of 210, 230, 254, 280, and 320 nm. Purity of target molecules (with reported biological data) was ≥95% (as determined by HPLC at one or more scanned wavelengths) with the exception of compound 27 (94.3% at 254 nm). Mass spectrometry was carried out under positive or negative ESI (electrospray ionization) using a Thermo Scientific LTQ Orbitrap Discovery instrument.

Figure 3:
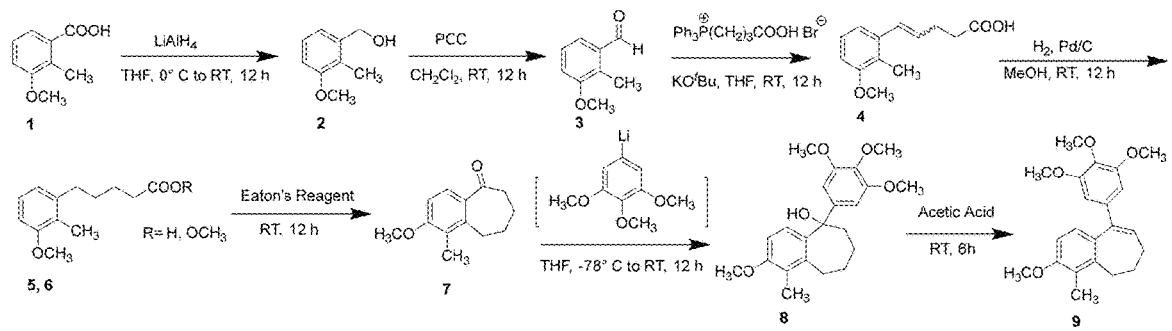
FIG. 3 shows synthetic Scheme 1 for the synthesis of a representative compound described herein.

FIG. 3 shows Scheme 1, synthesis of compound 9: 1-methy-2-methoxy-5-(3', 4', 5'-trimethoxyphenyl)-benzosuber-5-ene. The tertiary alcohol (2.38 g, 6.4 mmol) was dissolved in acetic acid (15 mL) and stirred for 6 hours. The reaction was quenched with water (100 mL) and then extracted with EtOAc, washed with brine, and dried with Na$_2$SO$_4$. The organic layer was concentrated and purified by flash chromatography using a prepacked 100 g silica column [solvent A: EtOAc; solvent B: hexane; gradient: 7% A/93% B (3 CV), 7% A/93% B→60% A/40% B (10 CV), 60% A/40% B (1 CV); flow rate: 25 mL/min; monitored at 254 and 280 nm] affording the target molecule (1.78 g, 5.0 mmol, 78%) as a white powder. $^1$H NMR (CDCl$_3$, 500 MHz) δ 6.86 (1H, d, J=10.0 Hz), 6.70 (1H, d, J=10.0 Hz), 6.52 (2H, s), 6.32 (1H, t, J=7.5 Hz), 2.68 (2H, t, J=6.5 Hz), 2.29 (3H, s), 2.12 (2H, p, J=7.0 Hz), 1.91 (2H, q, J=7.5 Hz). $^{13}$C NMR (CDCl$_3$, 125 MHz) δ 156.5, 152.8, 143.5, 141.7, 138.6, 137.3, 133.0, 127.4, 126.5, 123.2, 107.4, 105.3, 60.9, 56.1, 55.5, 34.0, 27.7, 25.5, 11.8. HRMS: Obsvd 355.1906 [M+H]$^+$, calcd for C$_{22}$H$_{27}$O$_5$: 355.1904. HPLC: 19.87 min.

Figure 4:
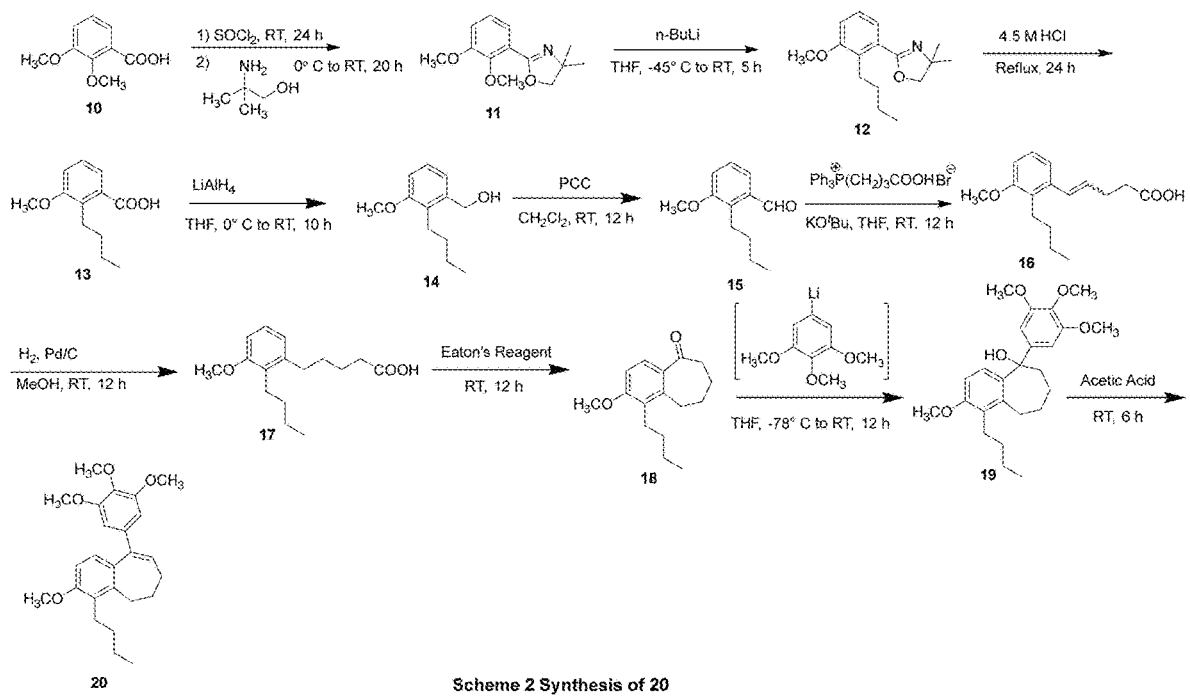
FIG. 4 shows synthetic Scheme 2 for the synthesis of a representative compound described herein.

FIG. 4 shows Scheme 2, synthesis of compound 20: 4-Butyl-3-methoxy-9-(30,40,50-trimethoxyphenyl)-6,7-dihydro-5H-benzo[7]annulene. The tertiary alcohol (0.76 g, 1.8 mmol) was dissolved in acetic acid (10 mL), and the reaction mixture was stirred for 6 h. The reaction was quenched with water (50 mL) and extracted with EtOAc (3*20 mL). The combined organic phase was washed with brine, dried with Na$_2$SO$_4$ and concentrated under reduced pressure. The crude reaction product was purified by flash chromatography using a prepacked 50 g silica column [solvent A: EtOAc; solvent B: hexanes; gradient: 7% A/93% B (3 CV), 7% A/93% B?60% A/40% B (10 CV), 60% A/40% B (1 CV); flow rate: 40 mL/min; monitored at 254 and 280 nm] to afford the target molecule (0.76 g, 1.8 mmol, quantitative) as a yellowish oil. 1H NMR (CDCl3, 500 MHz) d 6.84 (1H, d, J=8.5 Hz), 6.69 (1H, d, J=8.5 Hz), 6.51 (2H, s), 6.32 (1H, t, J=7.4 Hz), 3.86 (3H, s), 3.83 (3H, s), 3.81 (6H, s), 2.74 (2H, m), 2.68 (2H, t, J=6.9 Hz), 2.13 (2H, p, J=7.0 Hz), 1.91 (2H, q, J=7.3 Hz), 1.53 (2H, m), 1.46 (2H, m), 0.98 (3H, t, J=7.3 Hz). $^{13}$C NMR (CDCl3, 125 MHz) d 156.4, 152.8, 143.5, 141.2, 138.7, 137.3, 133.1, 128.5, 127.5, 126.4, 107.5, 105.3, 60.9, 56.2, 55.4, 34.9, 32.9, 27.3, 26.3, 25.5, 23.2, 14.1. HRMS: Obsd 397.2374 [M+H]+, calcd for C$_{25}$H$_{33}$O$_4$: 397.2373. HPLC: 22.30 min.

Figure 5:
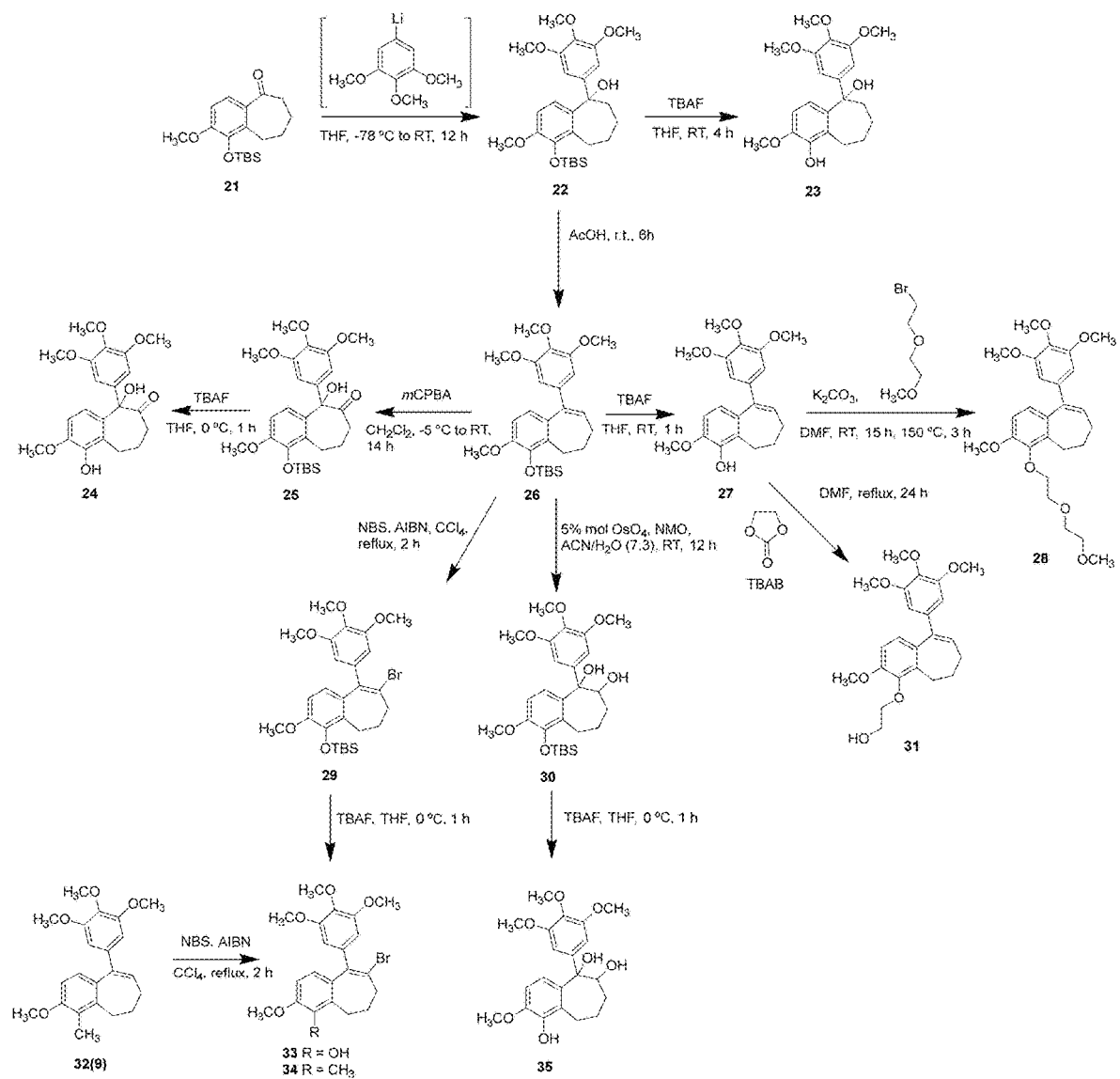
FIG. 5 shows synthetic Scheme 3 for the synthesis of representative compounds described herein.

FIG. 5 shows Scheme 3, synthesis of compounds 23, 24, 28, 31, 33, 34, and 35. Structural modifications included: 1) functional group (R) modifications on the fused aryl ring including the installation of alcohol, aldehyde, nitrile, and ester groups along with ether linkages to facilitate extension of the polar alcohol moiety away from the fused six-seven ring system; 2) R$_2$ and R$_3$ incorporation at the olefinic and allylic positions of the seven-membered ring introduced —Br, —OH, and —NHAc groups; 3) modification (R$_4$ position) of the fused aliphatic ring adjacent to the tertiary alcohol site; 4) olefination and pendant trimethoxy phenyl ring regiochemistry on the fused non-aromatic ring. The synthesis of analogues 23, 24, 28, 31, 33, 35 was initiated from a common intermediate ketone 21 that was readily available utilizing previous methodolgy. Treatment of benzosuberone 21 with trimethoxyphenyllithium (prepared from the corresponding bromide) generated tertiary alcohol 22, which was subsequently converted to diol 23 upon removal of the phenolic TBS protecting group. Separately, tertiary alcohol 22 was converted to its corresponding benzosuberene 26, which underwent treatment with a series of oxidants (m-CPBA, NBS, OsO$_4$) to facilitate epoxidation followed by ring opening and oxidation, bromination, and Upjohn dihydroxylation. Following the removal of protecting groups, target compounds 24, 33, and 35 were obtained. Similarly, reaction of 4-methylbenzosuberene 32(9) (prepared previously) with NBS/AIBN afforded vinylbromide 33. Lead compound 27 (referred to as KGP18), also available through this methodology, was directly converted to its corresponding ether analogues 28 and 31 (Scheme 3).

1-((Tert-butyldimethylsilyl)oxy)-2-methoxy-5-(3,4,5-trimethoxyphenyl)-6,7,8,9-tetrahydro-5H-benzo[7]annulen-5-ol (22)

To an oven dried flask, THF (10 mL) and 3,4,5-trimethoxyphenyl bromide (0.89 g, 3.6 mmol) were added, and the solution was cooled to −78° C. n-BuLi (1.44 mL, 3.60 mmol) was added dropwise to the reaction mixture, which was then stirred at −78° C. for 1 h. TBS-protected ketone (21) (0.77 g, 2.4 mmol) in THF (5 mL) was then added slowly to the flask, and the reaction mixture was stirred while warming from −78° C. to room temperature over 12 h. The reaction mixture was quenched with water and extracted with EtOAc (3×30 mL). The combined organic phase was dried over sodium sulfate and evaporated under reduced pressure. The crude reaction product was purified by flash chromatography using a pre-packed 50 g silica column [solvent A: EtOAc; solvent B: hexanes; gradient: 2% A/98% B (1 CV), 2% A/98% B→20% A/80% B (10 CV), 20% A/80% B (2 CV); flow rate: 50 mL/min; monitored at 254 and 280 nm] to afford tertiary alcohol 22 (1.05 g, 2.15 mmol, 89%) as a clear oil. $^1$H NMR (500 MHz, CDCl$_3$) δ 7.15 (1H, d, J=9 Hz), 6.69 (1H, d, J=9 Hz), 6.50 (2H, s), 3.84 (3H, s), 3.80 (3H, s), 3.75 (6H, s), 3.29 (1H, m), 2.56 (1H, m), 2.26 (1H, m), 2.12 (2H, m), 1.90 (1H, m), 1.75 (2H, m), 0.99 (9H, s), 0.17 (3H, s), 0.15 (3H, s). $^{13}$C NMR (125 MHz, CDCl$_3$) δ 153.1, 149.4, 142.0, 141.9, 138.7, 137.3, 132.9, 119.8, 108.0, 104.4, 80.2, 61.0, 56.2, 54.8, 41.4, 27.1, 26.4, 26.2, 25.5, 19.1, −3.8, −4.0.

2-Methoxy-5-(3,4,5-trimethoxyphenyl)-6,7,8,9-tetrahydro-5H-benzo[7]annulene-1,5-diol (23)

TBS-protected tertiary alcohol 22 (0.41 g, 0.84 mmol) was dissolved in THF (6 mL), and TBAF (1.01 mL, 1 M in THF, 1.01 mmol) was added, and the reaction mixture was stirred at room temperature for 4 h. The solution was washed with water and extracted with EtOAc (3×20 mL). The combined organic phase was dried over sodium sulfate and evaporated under reduced pressure. The crude reaction product was purified by flash chromatography using a pre-packed 10 g silica column [solvent A: EtOAc; solvent B: hexanes; gradient: 3% A/97% B (1 CV), 3% A/97% B→30% A/70% B (10 CV), 30% A/70% B (2 CV); flow rate: 12 mL/min; monitored at 254 and 280 nm] to afford phenol (0.11 g, 0.29 mmol, 35%) as a colorless oil. $^1$H NMR (500 MHz, CDCl$_3$) δ 7.04 (1H, d, J=9 Hz), 6.70 (1H, d, J=9 Hz), 6.52 (2H, s), 5.79 (1H, s), 3.91 (3H, s), 3.84 (3H, s), 3.76 (6H, s), 3.23 (1H, m), 2.56 (1H, m), 2.35 (1H, m), 2.11 (1H, m), 1.92 (1H, m), 1.75 (2H, m), 1.47 (1H, m). $^{13}$C NMR (125 MHz, CDCl$_3$) δ 153.1, 145.6, 142.7, 141.9, 139.4, 137.3, 127.2, 118.2, 107.3, 104.4, 80.2, 61.0, 56.3, 56.0, 41.5, 26.8, 26.3, 24.7. HRMS: Obsvd 397.1623 [M+Na$^+$], Calcd for C$_{21}$H$_{26}$O$_6$Na: 397.1622. HPLC: 16.33 min.

Tert-butyl((3-methoxy-9-(3,4,5-trimethoxyphenyl)-6,7-dihydro-5H-benzo[7]annulen-4-yl)oxy)dimethylsilane (26)

TBS-protected tertiary alcohol 22 (0.64 g, 1.3 mmol) was dissolved in acetic acid (10 mL), and the reaction mixture was stirred at room temperature for 6 h. The unreacted acetic acid was removed under reduced pressure. The resulting reaction mixture was washed with water and extracted with EtOAc (3×30 mL). The combined organic extracts were washed with brine, dried over sodium sulfate, evaporated under reduced pressure and purified by flash chromatography using a pre-packed 25 g silica column [solvent A: EtOAc, solvent B: hexanes; gradient: 5% A/95% B (1 CV), 5% A/95% B→50% A/50% B (10 CV), 50% A/50% B (2 CV); flow rate: 25 mL/min; monitored at 254 and 280 nm] to afford a clear oil that solidified as a colorless solid of TBS-protected benzosuberene analogue 26 (0.41 g, 0.87 mmol, 66%). $^1$H NMR (CDCl$_3$, 500 MHz) δ 6.68 (1H, d, J=8.5 Hz), 6.61 (1H, d, J=8.5 Hz), 6.48 (2H, s), 6.32 (1H, t, J=7 Hz), 3.85 (3H, s), 3.81 (3H, s), 3.79 (6H, s), 2.76 (2H, t, J=7 Hz), 2.10 (2H, m), 1.95 (2H, m), 1.04 (9H, s), 0.23 (6H, s). $^{13}$C NMR (CDCl$_3$, 125 MHz) δ 152.9, 148.8, 143.2, 141.6, 138.8, 137.3, 133.9, 133.4, 127.0, 122.5, 108.5, 105.3, 61.0, 56.2, 54.8, 34.1, 26.3, 25.7, 24.4, 19.2, −3.7.

1-(Tert-butyldimethylsilyl)oxy)-5-hydroxy-2-methoxy-5-(3,4,5-trimethoxyphenyl)-5,7,8,9-tetrahydro-6H-benzo[7]annulen-6-one (25)

To a solution of TBS-protected benzosuberene 26 (0.51 g, 1.1 mmol) dissolved in CH$_2$Cl$_2$ (20 mL) was added m-CPBA (0.36 g, 2.1 mmol) at −5° C., and the reaction mixture was stirred for 2 h and then at room temperature for 12 h. The solution was washed with saturated Na$_2$S$_2$O$_3$ and saturated NaHCO$_3$ and extracted with CH$_2$Cl$_2$ (3×20 mL). The combined organic layers were dried over sodium sulfate and evaporated under reduced pressure. The crude product was purified by flash chromatography using a pre-packed 50 g silica column [solvent A: EtOAc; solvent B: hexanes; gradient: 5% A/95% B (1 CV), 5% A/95% B→60% A/40% B (10 CV), 60% A/40% B (2 CV); flow rate: 100 mL/min; monitored at 254 and 280 nm] to afford tertiary alcohol 25 (0.256 g, 0.51 mmol, 47%) as a yellow oil. $^1$H NMR (600 MHz, CDCl$_3$) δ 7.26 (1H, d, J=9 Hz), 6.76 (1H, d, J=9 Hz), 6.42 (2H, s), 5.01 (1H, s), 3.83 (3H, s), 3.81 (3H, s), 3.75 (6H, s), 3.10 (2H, m), 2.82 (1H, m), 2.70 (1H, m), 1.98 (1H, m), 1.76 (1H, m). $^{13}$C NMR (150 MHz, CDCl$_3$) δ 211.1, 153.4, 150.2, 142.1, 138.0, 137.5, 131.4, 131.1, 127.8, 109.1, 105.2, 85.6, 61.0, 56.3, 54.8, 39.7, 26.2, 25.8, 24.2, 19.1, −3.7, −3.9.

1,5-Dihydroxy-2-methoxy-5-(3,4,5-trimethoxyphenyl)-5,7,8,9-tetrahydro-6H-benzo[7]annulen-6-one (24)

TBS-protected benzosuberane 25 (0.17 g, 0.33 mmol) was dissolved in THF (10 mL). TBAF (0.33 mL, 1 M, 0.33 mmol) was added, and the reaction mixture was stirred at room temperature for 1 h at 0° C. A brine (30 mL) solution was added, and the reaction mixture was extracted with EtOAc (3×30 mL). The combined organic phase was dried over sodium sulfate, filtered, evaporated under reduced pressure, and purified by flash chromatography using a pre-packed 50 g silica column [solvent A: EtOAc; solvent B: hexanes; gradient: 5% A/95% B (1 CV), 5% A/95% B→60% A/40% B (10 CV), 60% A/40% B (2 CV); flow rate: 100 mL/min; monitored at 254 and 280 nm] to afford phenol 24 (123 mg, 0.320 mmol, 96%) as a white solid. $^1$H NMR (600 MHz, CDCl$_3$) δ 7.17 (1H, d, J=8.4 Hz), 6.77 (1H, d, J=9 Hz), 6.43 (2H, s), 5.88 (1H, s), 5.00 (1H, s), 3.90 (3H, s), 3.82 (3H, s), 3.74 (6H, s), 3.08 (2H, m), 2.84 (1H, m), 2.68 (1H, m), 1.99 (1H, m), 1.83 (1H, m). $^{13}$C NMR (150 MHz, CDCl$_3$) δ 211.0, 153.3, 146.4, 142.8, 138.0, 137.2, 131.6, 125.7, 120.2, 108.4, 105.2, 85.5, 60.9, 56.3, 56.0, 39.4, 25.4, 23.3. HRMS: Obsvd 411.1414 [M+Na$^+$], Calcd for C$_{21}$H$_{24}$O$_7$Na: 411.1414. HPLC: 15.75 min.

3-Methoxy-9-(3,4,5-trimethoxyphenyl)-6,7-dihydro-5H-benzo[7]annulen-4-ol (27)

TBS-protected benzosuberene 24 (0.41 g, 0.87 mmol) was dissolved in THF (10 mL). TBAF (1.13 mL, 1.13 mmol) was added, and the reaction mixture was stirred at room temperature for 1 h. The solution was washed with water and extracted with EtOAc (3×20 mL). The combined organic phase was dried over sodium sulfate and evaporated under reduced pressure. The crude reaction product was purified by flash chromatography using a pre-packed 10 g silica column [solvent A: EtOAc; solvent B: hexanes; gradient: 3% A/97% B (1 CV), 3% A/97% B→30% A/70% B (10 CV), 30% A/70% B (2 CV); flow rate: 12 mL/min; monitored at 254 and 280 nm] to afford phenol 27 (0.25 g, 0.70 mmol, 81%) as a white solid. $^1$H NMR (CDCl$_3$, 500 MHz) δ 6.71 (1H, d, J=9 Hz), 6.56 (1H, d, J=9 Hz), 6.50 (2H, s), 6.34 (1H, t, J=7.5 Hz), 5.74 (1H, s), 3.91 (3H, s), 3.86 (3H, s), 3.80 (6H, s), 2.76 (2H, t, J=7 Hz), 2.14 (2H, m), 1.97 (2H, m). $^{13}$C NMR (CDCl$_3$, 125 MHz) δ 152.9, 145.2, 142.9, 142.4, 138.6, 134.4, 127.9, 127.4, 121.0, 110.1, 107.8, 105.4, 61.1, 56.3, 56.1, 33.7, 25.9, 23.7.

3-Methoxy-4-(2-(2-methoxyethoxy)ethoxy)-9-(3,4,5-trimethoxyphenyl)-6,7-dihydro-5H-benzo[7]annulene (28)

Phenol 27 (0.11 g, 0.31 mmol) was dissolved in DMF (6 mL), and K$_2$CO$_3$ (0.12 g, 0.86 mmol) was added. The solution was stirred at room temperature for 20 min. 1-Bromo-2-(2-methoxyethoxy) ethane in 90% purity (0.07 mL, 0.5 mmol) was added, the reaction mixture was stirred at room temperature for 15 h. The solution was washed with water and extracted with EtOAc (3×40 mL). The combined organic phase was dried over sodium sulfate and evaporated under reduced pressure. The crude reaction product was purified by flash chromatography using a pre-packed 10 g silica column [solvent A: EtOAc; solvent B: hexanes; gradient: 3% A/97% B (1 CV), 3% A/97% B→30% A/70% B (20 CV), 30% A/70% B (2 CV); flow rate: 12 mL/min; monitored at 254 and 280 nm] to afford ether 28 (25 mg, 0.06 mmol, 18%) as a colorless oil. $^1$H NMR (500 MHz, CDCl$_3$) δ 6.74 (2H, m), 6.48 (2H, s), 6.32 (1H, t, J=7.5 Hz), 4.18 (2H, t, J=5 Hz), 3.87 (2H, t, J=5.5 Hz), 3.85 (6H, s), 3.79 (6H, s), 3.76 (2H, m), 3.60 (2H, m), 3.40 (3H, s), 2.78 (2H, t, J=6.5 Hz), 2.13 (2H, m), 1.93 (2H, m). $^{13}$C NMR (125 MHz, CDCl$_3$) δ 152.9, 151.5, 145.1, 142.9, 138.5, 137.4, 136.1, 133.8, 127.3, 125.3, 109.3, 105.3, 72.8, 72.2, 70.78, 70.77, 61.0, 59.2, 56.2, 55.7, 34.5, 25.7, 24.2. HRMS: Obsvd 481.2198 [M+Na$^+$], Calcd for C$_{26}$H$_{34}$O$_7$Na: 481.2197. HPLC: 21.65 min.

((8-Bromo-3-methoxy-9-(3,4,5-trimethoxyphenyl)-6,7-dihydro-5H-benzo[7]annulen-4-yl)oxy)(tert-butyl)dimethylsilane (29)

To a solution of TBS-protected benzosuberene (102 mg, 0.22 mmol) in CCl$_4$ (30 mL) was added NBS (46 mg, 0.26 mmol) and AIBN (3.6 mg, 0.02 mmol). The solution was heated at reflux for 2 h, followed by the addition of water (20 mL) and extraction with CH$_2$Cl$_2$ (3×30 mL). The combined organic phase was dried over sodium sulfate, filtered, and the solvent was removed under reduced pressure. The crude product was obtained as a yellow oil and taken to the next step directly without any further purification.

1-((Tert-butyldimethylsilyl)oxy)-2-methoxy-5-(3,4,5-trimethoxyphenyl)-6,7,8,9-tetrahydro-5H-benzo[7]annulene-5,6-diol (30)

To a solution of TBS-protected benzosuberene 26 (1.00 g, 2.12 mmol) in acetone/water (35 mL/15 mL) were added OsO$_4$ (270 mg, 1.06 mmol) and N-methylmorpholine-N-oxide (0.66 mL, 4.8 M, 3.2 mmol) at room temperature, and the reaction mixture was stirred for 12 h. A saturated sodium hydrosulfite (20 mL) solution was added, and the reaction mixture was extracted with EtOAc (5×20 mL). The combined organic extracts were washed with brine, dried over sodium sulfate, filtered, evaporated under reduced pressure, and purified by flash chromatography using a pre-packed 50 g silica column [solvent A: EtOAc; solvent B: hexanes; gradient: 5% A/95% B (1 CV), 5% A/95% B→60% A/40% B (10 CV), 60% A/40% B (2 CV); flow rate: 100 mL/min; monitored at 254 and 280 nm] to afford diol 30 (0.35 mg, 0.69 mmol, 33%) as an orange oil. $^1$H NMR (600 MHz, CDCl$_3$) δ 7.30 (1H, d, J=8.4 Hz), 6.74 (1H, d, J=9 Hz), 6.47 (2H, s), 4.51 (1H, s, b), 3.81 (3H, s), 3.80 (3H, s), 3.72 (6H, s), 3.42 (1H, m), 3.33 (1H, s), 2.15 (1H, m), 1.96 (2H, m), 1.83 (1H, m), 1.62 (1H, m), 1.51 (1H, m), 0.98 (9H, s), 0.15 (6H, d, J=3.6 Hz). $^{13}$C NMR (150 MHz, CDCl$_3$) δ 153.1, 149.8, 142.0, 138.8, 137.7, 133.1, 132.7, 122.3, 108.5, 105.0, 83.1, 76.5, 60.9, 56.2, 54.7, 32.7, 26.2, 25.9, 21.3, 19.0, −3.9, −4.0.

2-((3-Methoxy-9-(3,4,5-trimethoxyphenyl)-6,7-dihydro-5H-benzo[7]annulen-4-yl)oxy)ethan-1-ol (31)

Phenol 27 (0.14 g, 0.39 mmol) was dissolved in DMF (3 mL), then ethylene carbonate (70 mg, 0.79 mmol) and tetrabutyl ammonium bromide (0.13 g, 0.39 mmol) were added together. The solution was stirred and heated at reflux for 24 h. The reaction mixture was diluted with brine, extracted with EtOAc (3×10 mL), and the combined organic layers were dried over sodium sulfate, filtered, concentrated under reduced pressure, and purified by flash chromatography using a pre-packed 25 g silica column [solvent A: EtOAc; solvent B: hexanes; gradient: 7% A/93% B (1 CV), 7% A/93% B→60% A/40% B (10 CV), 60% A/40% B (2 CV); flow rate: 25 mL/min; monitored at 254 and 280 nm] to afford alcohol 31 (0.11 g, 0.27 mmol, 68%). $^1$H NMR (500 MHz, CDCl$_3$) δ 6.76 (2H, m), 6.47 (2H, s), 6.33 (1H, t, J=7.5 Hz), 4.12 (2H, m), 3.89 (2H, m), 3.88 (3H, s), 3.84 (3H, s), 3.79 (6H, s), 2.75 (2H, t, J=7 Hz), 2.15 (2H, m), 1.95 (2H, m). $^{13}$C NMR (125 MHz, CDCl$_3$) δ 152.9, 151.1, 145.0, 142.8, 138.3, 137.4, 136.1, 134.2, 127.3, 125.7, 109.2, 105.3, 76.1, 62.2, 61.0, 56.2, 55.8, 34.6, 25.6, 24.6. HRMS: Obsvd 423.1780 [M+Na$^+$], Calcd for C$_{23}$H$_{28}$O$_6$Na: 423.1778. HPLC: 13.77 min.

8-Bromo-3-methoxy-9-(3,4,5-trimethoxyphenyl)-6,7-dihydro-5H-benzo[7]annulen-4-ol (33)

Brominated benzosuberene 29 (0.12 g, 0.22 mmol, crude) was dissolved in THF (20 mL), and TBAF (0.22 mL, 1 M, 0.22 mmol) was added to the solution at 0° C. The reaction mixture was stirred for 1 h, washed with brine (20 mL), and extracted with EtOAc (3×30 mL). The combined organic phase was dried over sodium sulfate, filtered, and evaporated under reduced pressure. The resulting material was purified by flash chromatography using a pre-packed 50 g silica column [solvent A: EtOAc; solvent B: hexanes; gradient: 7% A/93% B (1 CV), 7% A/93% B→40% A/60% B (10 CV), 40% A/60% B (2 CV); flow rate: 100 mL/min; monitored at 254 and 280 nm] to afford brominated phenol 33 (97 mg, 0.22 mmol, 100% over two steps) as a white crystalline solid. $^1$H NMR (600 MHz, CDCl$_3$) δ 6.63 (1H, d, J=8.4 Hz), 6.45 (2H, s), 6.41 (1H, d, J=8.4 Hz), 5.74 (1H, s), 3.88 (3H, s), 3.87 (3H, s), 3.80 (6H, s), 2.88 (2H, t, J=7.2 Hz), 2.58 (2H, t, J=7.2 Hz), 2.26 (2H, m). $^{13}$C NMR (150 MHz, CDCl$_3$) δ 152.7, 145.5, 142.5, 140.8, 137.9, 137.3, 135.3, 126.4, 121.5, 121.1, 108.0, 107.5, 61.0, 56.3, 56.1, 38.5, 32.5, 23.2. HRMS: Obsvd 457.0621 [M+Na$^+$], Calcd for C$_{21}$H$_{23}$BrO$_5$Na: 457.0621. HPLC: 17.54 min.

8-Bromo-3-methoxy-4-methyl-9-(3,4,5-trimethoxyphenyl)-6,7-dihydro-5H-benzo[7]annulene (34)

KGP391 32(9) (68 mg, 0.19 mmol) was dissolved in CCl$_4$ (20 mL), and NBS (37 mg, 0.21 mmol) and AIBN (3.1 mg, 0.02 mmol) were added carefully avoiding shaking or metal spatula since AIBN can be explosive. The reaction mixture was refluxed and stirred for 2 h. The solution was washed with water and extracted by CH$_2$Cl$_2$, the organic phase was further washed by brine and dried over sodium sulfate, filtered, concentrated under reduced pressure, and purified by flash chromatography using a pre-packed 10 g silica column [solvent A: EtOAc; solvent B: hexanes; gradient: 6% A/94% B (1 CV), 6% A/94% B→70% A/30% B (10 CV), 70% A/30% B (2 CV); flow rate: 12 mL/min; monitored at 254 and 280 nm] to afford brominated benzosuberene analogue 34 (66 mg, 0.15 mmol, 80%) as a white solid. $^1$H NMR (600 MHz, CDCl$_3$) δ 6.70 (1H, d, J=7 Hz), 6.62 (1H, d, J=7 Hz), 6.47 (2H, s), 3.88 (3H, s), 3.81 (9H, s), 2.81 (2H, m), 2.53 (2H, m), 2.26 (3H, s), 2.24 (2H, m). $^{13}$C NMR (150 MHz, CDCl$_3$) δ 156.8, 152.7, 141.4, 140.2, 138.0, 137.2, 134.2, 127.6, 123.5, 120.5, 107.7, 107.4, 61.0, 56.3, 55.6, 38.3, 33.0, 27.5, 11.9. HRMS: Obsvd 457.0808 [M+Na$^+$], Calcd for C$_{22}$H$_{25}$BrO$_4$Na: 455.0828. HPLC: 25.38 min.

2-Methoxy-5-(3,4,5-trimethoxyphenyl)-6,7,8,9-tetrahydro-5H-benzo[7]annulene-1,5,6-triol (35)

To a solution of TBS-protected phenol 30 (0.35 g, 0.69 mmol) in THF (20 mL) was added TBAF (0.76 mL, 1 M in THF, 0.76 mmol) at 0° C. The reaction mixture was stirred for 1 h, subsequently washed with brine (30 mL), and extracted with EtOAc (3×30 mL). The resultant organic phase was dried over sodium sulfate, filtered, evaporated under reduced pressure, and purified by flash chromatography using a pre-packed 50 g silica column [solvent A: EtOAc; solvent B: hexanes; gradient: 12% A/88% B (1 CV), 12% A/88% B→100% A/0% B (10 CV), 100% A/0% B (2 CV); flow rate: 100 mL/min; monitored at 254 and 280 nm] to afford diol phenol 35 (138 mg, 0.35 mmol, 51%) as a yellow solid. $^1$H NMR (600 MHz, CDCl$_3$) δ 7.24 (1H, d, J=8.4 Hz), 6.78 (1H, d, J=8.4 Hz), 6.51 (2H, s), 5.82 (1H, s), 4.56 (1H, m), 3.93 (3H, s), 3.83 (3H, s), 3.75 (6H, s), 3.37 (1H, m), 3.21 (1H, s), 2.24 (1H, m), 2.05 (1H, m), 1.96 (1H, m), 1.69 (2H, m). $^{13}$C NMR (150 MHz, CDCl$_3$) δ 153.3, 146.1, 142.8, 138.6, 137.9, 133.8, 127.0, 120.6, 107.9, 105.2, 83.3, 76.8, 61.0, 56.3, 56.0, 32.7, 25.1, 21.2. HRMS: Obsvd 413.1571 [M+Na$^+$], Calcd for C$_{21}$H$_{26}$O$_7$Na: 413.1571. HPLC: 13.71 min.

Figure 6:
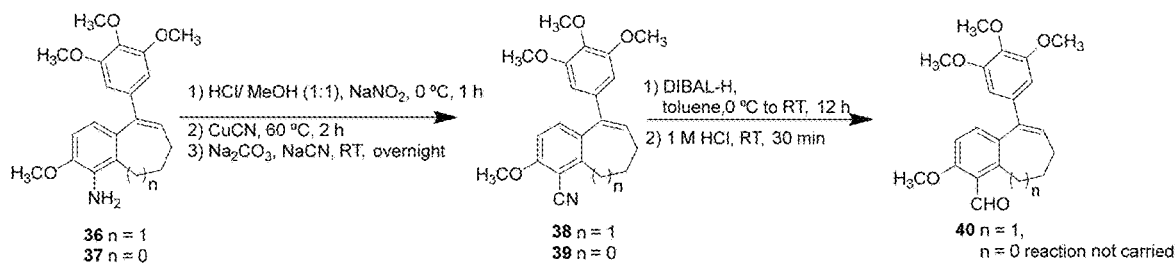
FIG. 6 shows synthetic Scheme 4 for the synthesis of representative compounds described herein.

FIG. 6 shows Scheme 4, synthesis of compounds 38, 39 and 40. Lead compounds benzosuberene 36 (referred to as KGP156) and its corresponding dihydronaphthalene analogue 37 (referred to as KGP05), which were readily available from our previous synthetic studies, were subjected to a Sandmeyer radical-nucleophilic aromatic substitution protocol to generate nitrile analogues 38 and 39 (Scheme 4). The benzosuberene aldehyde analogue 40 was obtained after subsequent reduction of the nitrile analogue.

3-Methoxy-9-(3,4,5-trimethoxyphenyl)-6,7-dihydro-5H-benzo[7]annulene-4-carbonitrile (38)

To KGP156 (0.10 g, 0.28 mmol) in a 2 M HCl/CH$_3$OH solution (5 mL/5 mL) was added NaNO$_2$ (77.7 mg, 1.12 mmol) at 0° C., and the mixture was stirred for 1 h. CuCN was added (50.4 mg, 0.56 mmol), and the reaction mixture was heated at 60° C. for 2 h. Na$_2$CO$_3$ and NaCN were added (50 mg of each), and the reaction mixture was stirred for 12 h at room temperature. A saturated FeCl$_3$ solution (50 mL) was added to quench the reaction, and the reaction mixture was extracted with EtOAc (3×30 mL). The combined organic phase was washed with brine and a saturated NaHCO$_3$ solution, then dried over sodium sulfate and evaporated under reduced pressure. The crude reaction was purified by flash chromatography using a pre-packed 50 g silica column [solvent A: EtOAc; solvent B: hexanes; gradient: 5% A/95% B (1 CV), 5% A/95% B→60% A/40% B (10 CV), 60% A/40% B (2 CV); flow rate: 100 mL/min; monitored at 254 and 280 nm] to afford nitrile 38 (41 mg, 0.11 mmol, 40%) as a yellow solid. $^1$H NMR (600 MHz, CDCl$_3$) δ 7.20 (1H, d, J=8.4 Hz), 6.80 (1H, d, J=8.4 Hz), 6.43 (1H, t, J=7.8 Hz), 6.42 (2H, s), 3.94 (3H, s), 3.86 (3H, s), 3.80 (6H, s), 2.90 (2H, t, J=7.2 Hz), 2.26 (2H, m), 1.94 (2H, m). $^{13}$C NMR (150 MHz, CDCl$_3$) δ 160.7, 153.1, 147.5, 141.6, 137.6, 137.5, 134.9, 133.4, 128.7, 116.1, 108.5, 105.0, 101.7, 61.1, 56.3, 56.2, 34.8, 25.7, 25.4. HRMS: Obsvd 388.1521 [M+Na$^+$], Calcd for C$_{22}$H$_{23}$NO$_4$Na: 388.1519. HPLC: 20.75 min.

2-Methoxy-5-(3,4,5-trimethoxyphenyl)-7,8-dihydronaphthalene-1-carbonitrile (39)

KGP05 (48.6 mg, 0.14 mmol) was dissolved in 2 M HCl/CH$_3$OH (2 mL/2 mL). The solution was cooled to 0° C., NaNO$_2$ (39.2 mg, 0.56 mmol) was added, and the resultant reaction mixture was stirred at 0° C. for 1 h. The reaction mixture was heated at 60° C. for 2 h before the addition of CuCN (25.5 mg, 0.28 mmol). After the reaction mixture was cooled to room temperature, Na$_2$CO$_3$ and NaCN were added to adjust the pH to 10 and provide more nitrile ions for improving the yield, followed by an additional 12 h of stirring. FeCl$_3$ was added to quench the reaction, followed by extraction with EtOAc (3×20 mL). The combined organic phase was washed with brine and a saturated NaHCO$_3$ solution, dried over sodium sulfate, and evaporated under reduced pressure. The crude reaction product was purified by flash chromatography using a pre-packed 50 g silica column [solvent A: EtOAc; solvent B: hexanes; gradient: 12% A/88% B (1 CV), 12% A/88% B→60% A/40% B (10 CV), 60% A/40% B (2 CV); flow rate: 100 mL/min; monitored at 254 and 280 nm] to afford nitrile 39 (17 mg, 0.046 mmol, 32%) as a white foam. $^1$H NMR (600 MHz, CDCl$_3$) δ 7.20 (1H, d, J=8.4 Hz), 6.69 (1H, d, J=9 Hz), 6.50 (2H, s), 6.03 (1H, t, J=4.8 Hz), 3.91 (3H, s), 3.88 (3H, s), 3.84 (6H, s), 3.06 (2H, t, J=7.8 Hz), 2.43 (2H, m). $^{13}$C NMR (150 MHz, CDCl$_3$) δ 160.3, 153.3, 142.9, 138.5, 137.6, 135.8, 130.8, 128.8, 126.1, 115.6, 108.3, 105.8, 101.6, 61.1, 56.3, 56.2, 26.8, 22.7. HRMS: Obsvd 374.1363 [M+Na+], Calcd for $C_{21}H_{21}NO_4Na$: 374.1363. HPLC: 20.92 min.

3-Methoxy-9-(3,4,5-trimethoxyphenyl)-6,7-dihydro-5H-benzo[7]annulene-4-carbaldehyde (40)

To a solution of nitrile 38 (48 mg, 0.13 mmol) in toluene (15 mL) was added DIBAL-H (0.16 mL, 1 M, 0.16 mmol) at 0° C., and the resultant solution was stirred for 12 h while warming to room temperature. 1 M HCl (100 mL) was added to the reaction mixture, which was stirred for 30 min at room temperature while the solution color turned to yellow. EtOAc (3×50 mL) was used to extract the organic compound. The combined organic phase was dried over sodium sulfate and concentrated under reduced pressure. The crude product was purified by flash chromatography using a pre-packed 50 g silica column [solvent A: EtOAc; solvent B: hexanes; gradient: 5% A/95% B (1 CV), 5% A/95% B→60% A/40% B (10 CV), 60% A/40% B (2 CV); flow rate: 100 mL/min; monitored at 254 and 280 nm] to afford aldehyde 40 (37.8 mg, 0.10 mmol, 78%) as a white solid. $^1$H NMR (600 MHz, $CDCl_3$) δ 10.68 (1H, s), 7.18 (1H, d, J=7.2 Hz), 6.82 (1H, d, J=8.4 Hz), 6.47 (2H, s), 6.43 (1H, t, J=7.8 Hz), 3.92 (3H, s), 3.86 (3H, s), 3.81 (6H, s), 2.99 (2H, m), 2.27 (2H, m), 1.91 (2H, m). $^{13}$C NMR (150 MHz, $CDCl_3$) δ 193.3, 161.8, 153.2, 145.2, 141.9, 138.2, 137.6, 135.5, 134.7, 128.8, 123.7, 108.7, 105.3, 61.1, 56.3, 55.9, 31.7, 25.7, 22.8. HRMS: Obsvd 391.1519 [M+Na+], Calcd for $C_{22}H_{24}O_5Na$: 391.1516. HPLC: 22.39 min.

Figure 7:
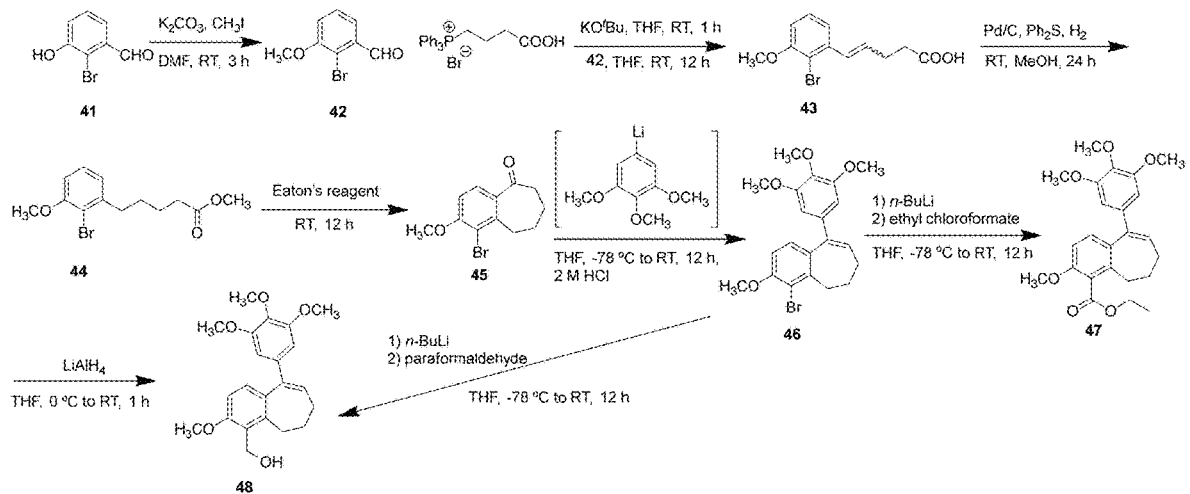
FIG. 7 shows synthetic Scheme 5 for the synthesis of representative compounds described herein.

FIG. 7 shows Scheme 5, synthesis of compounds 47 and 48. As part of a larger program focused on the use of potently cytotoxic benzosuberene and dihydronaphthalene analogues as payloads in antibody-drug conjugates (ADCs) and as prodrugs targeted for selective release in regions of profound tumor hypoxia, the possibility of replacing the heteroatom [oxygen (phenol) or nitrogen (aniline)] at the 4-position with a short carbon chain terminating with a primary alcohol (or amino) moiety was considered, thus maintaining its hydrogen-bond donor nature and serving as a viable position for future attachment of various linkers. Accordingly, methylation of phenolic bromo-aldehyde 41 (Scheme 5), followed by Wittig olefination and subsequent hydrogenation (under $Ph_2S$ mediation to maintain the aryl bromine group) afforded methyl ester 44. Benzosuberone 45 was obtained through an intramolecular Friedel-Crafts annulation facilitated by Eaton's reagent (7.7% weight percent $P_2O_5$ in $CH_3SO_3H$), and subsequent treatment of compounds 45 with trimethoxyphenyllithium, followed by reaction work-up under acidic conditions, generated benzosuberene intermediate 46. Corresponding fluorine and chlorine benzosuberene analogues were previously investigated. Halogen-lithium exchange, followed by reaction with ethyl chloroformate, afforded ethyl ester 47, which was reduced ($LiAlH_4$) to generate benzylic alcohol 48. Notably, while it proved possible to obtain analogue 48 directly from intermediate 46, the isolated yield was quite low (≤8%) under these conditions, which was likely due, in part, to the low solubility of paraformaldehyde at low temperature in THF and its low reactivity as a polymer.

2-Bromo-3-methoxybenzaldehyde (42)

To a solution of 2-bromo-3-hydroxybenzaldehyde 41 (2.50 g, 12.4 mmol) in DMF (50 mL) was added $CH_3I$ (1.01 mL, 16.2 mmol) and $K_2CO_3$ (1.35 g, 13.7 mmol). The reaction mixture was stirred at room temperature for 3 h. The solvent was removed under reduced pressure, and the residue was washed with water (50 mL) and extracted with EtOAc (3×50 mL). The organic phases were combined and concentrated without further purification to afford 2-bromo-3-methoxybenzaldehyde 42 (2.67 g, 12.4 mmol, 100%) as a brown solid. $^1$H NMR (600 MHz, $CDCl_3$) δ 10.44 (1H, s), 7.52 (1H, d, J=7.8 Hz), 7.38 (1H, t, J=7.8 Hz), 7.13 (1H, d, J=8.4 Hz), 3.96 (3H, s). $^{13}$C NMR (150 MHz, $CDCl_3$) δ 192.4, 156.4, 134.9, 128.5, 121.6, 117.3, 117.1, 56.8.

5-(2-Bromo-3-methoxyphenyl)pent-4-enoic acid (43)

To dissolved 3-(carboxypropyl)triphenyl phosphonium bromide (5.33 g, 12.4 mmol) in THF (250 mL) was added potassium tert-butoxide (3.08 g, 27.3 mmol), and the reaction mixture was stirred at room temperature for 1 h. 2-Bromo-3-methoxybenzaldehyde 42 (2.67 g, 16.2 mmol) was added, and the reaction mixture was stirred at room temperature for 12 h. The THF was removed under reduced pressure, and the resulting material was quenched and acidified with 2 M HCl (30 mL) and extracted with EtOAc (3×50 mL). The combined organic phase was dried over sodium sulfate, filtered, and evaporated under reduced pressure. The crude reaction product was purified by flash chromatography using a pre-packed 100 g silica column [solvent A: EtOAc; solvent B: hexanes; gradient: 12% A/88% B (1 CV), 12% A/88% B→60% A/40% B (10 CV), 60% A/40% B (2 CV); flow rate: 100 mL/min; monitored at 254 and 280 nm] to afford carboxylic acid 43 (1.74 g, 6.10 mmol, 49%) as a white solid. NMR characterization was performed after the next step.

Methyl 5-(2-bromo-3-methoxyphenyl)pentanoate (44)

To dissolved carboxylic acid 43 (0.69 g, 2.42 mmol) in $CH_3OH$ (30 mL) was added 10% palladium on carbon (0.26 g), $Ph_2S$ (40 µL, 0.24 mmol), and two balloons with hydrogen gas. After stirring for 24 h, the mixture was filtered through Celite®, and the Celite® was washed with EtOAc (3×50 mL). The combined organic phase ($CH_3OH$ and EtOAc) was evaporated under reduced pressure. The residue was purified by flash chromatography using a pre-packed 50 g silica column [solvent A: EtOAc; solvent B: hexanes; gradient: 7% A/93% B (1 CV), 7% A/93% B→40% A/60% B (10 CV), 40% A/60% B (2 CV); flow rate: 100 mL/min; monitored at 254 and 280 nm] to afford saturated ester 44 (0.48 g, 1.6 mmol, 66%) as a colorless oil. $^1$H NMR (600 MHz, $CDCl_3$) δ 7.54 (1H, t, J=7.8 Hz), 7.19 (1H, d, J=8.4 Hz), 7.10 (1H, d, J=7.8 Hz), 4.24 (3H, s), 4.02 (3H, s), 3.14 (2H, m), 2.72 (2H, m), 2.07 (2H, m), 2.02 (2H, m). $^{13}$C NMR (150 MHz, $CDCl_3$) δ 174.2, 156.1, 143.3, 127.8, 122.5, 113.9, 109.5, 56.4, 51.6, 36.1, 34.0, 29.4, 24.8.

1-Bromo-2-methoxy-6,7,8,9-tetrahydro-5H-benzo[7]annulen-5-one (45)

To ester 44 (0.48 g, 1.6 mmol) was added Eaton's reagent (8.5 mL), and the mixture was stirred at room temperature for 12 h. The reaction mixture was then poured over ice and neutralized with sodium carbonate. The aqueous layer was extracted with EtOAc (3×40 mL). The combined organic phase was dried over sodium sulfate, evaporated under reduced pressure, and purified by flash chromatography using a pre-packed 50 g silica column [solvent A: EtOAc; solvent B: hexanes; gradient: 5% A/95% B (1 CV), 5% A/95% B→40% A/60% B (10 CV), 40% A/60% B (2 CV);

flow rate: 100 mL/min; monitored at 254 and 280 nm] to afford benzosuberone 45 (0.20 g, 0.74 mmol, 47%) as a colorless oil. $^1$H NMR (600 MHz, CDCl$_3$) δ 7.63 (1H, d, J=8.4 Hz), 6.82 (1H, d, J=8.4 Hz), 3.94 (3H, s), 3.17 (2H, m), 2.69 (2H, m), 1.85 (2H, m), 1.75 (2H, m). $^{13}$C NMR (150 MHz, CDCl$_3$) δ 205.2, 159.0, 142.1, 133.7, 129.1, 114.1, 109.4, 56.6, 40.5, 31.2, 23.9, 20.7.

4-Bromo-3-methoxy-9-(3,4,5-trimethoxyphenyl)-6,7-dihydro-5H-benzo[7]annulene (46)

To an oven dried flask, THF (20 mL) and 3, 4, 5-trimethoxyphenyl bromide (1.12 g, 4.53 mmol) were added, and the solution was cooled to −78° C. n-Buli (1.81 mL, 2.5 M, 4.52 mmol) was slowly added to the reaction mixture, which was then stirred at −78° C. for 45 min. Benzosuberone 45 (0.61 g, 2.3 mmol) was then added to the flask dropwise, and the reaction mixture was stirred while warming from −78° C. to room temperature over 12 h. The reaction mixture was washed with water and extracted with EtOAc (3×40 mL). The combined organic phase was dried over sodium sulfate and evaporated under reduced pressure. The crude reaction product was purified by flash chromatography using a pre-packed 50 g silica column [solvent A: EtOAc; solvent B: hexanes; gradient: 7% A/93% B (1 CV), 7% A/93% B→20% A/80% B (10 CV), 20% A/80% B (2 CV); flow rate: 100 mL/min; monitored at 254 and 280 nm] to afford brominated benzosuberone 46 (0.46 g, 1.1 mmol, 49%) as a white solid. $^1$H NMR (600 MHz, CDCl$_3$) δ 6.97 (1H, d, J=8.4 Hz), 6.75 (1H, d, J=8.4 Hz), 6.48 (2H, s), 6.37 (1H, t, J=7.8 Hz), 3.92 (3H, s), 3.86 (3H, s), 3.81 (6H, s), 2.95 (2H, t, J=7.2 Hz), 2.17 (2H, m), 1.92 (2H, m). $^{13}$C NMR (150 MHz, CDCl$_3$) δ 154.9, 153.1, 143.0, 142.8, 138.0, 137.6, 134.4, 129.1, 127.8, 113.4, 109.1, 105.3, 61.0, 56.4, 56.3, 33.8, 31.9, 25.4.

Ethyl 3-methoxy-9-(3,4,5-trimethoxyphenyl)-6,7-dihydro-5H-benzo[7]annulene-4-carboxylate (47)

To a solution of brominated benzosuberone 46 (0.15 g, 0.36 mmol) in THF (20 mL) was added n-Buli (0.34 mL, 1.6 M, 0.54 mmol) dropwise at −78° C. The reaction mixture was stirred at −78° C. for 30 min, followed by the addition of ethyl chloroformate (61.5 μL, 0.64 mmol). The reaction mixture was stirred while warming from −78° C. to room temperature over 12 h. The reaction mixture was washed with water and extracted with EtOAc (3×30 mL). The combined organic phase was dried over sodium sulfate and evaporated under reduced pressure. The crude product was purified by flash chromatography using a pre-packed 50 g silica column [solvent A: EtOAc; solvent B: hexanes; gradient: 7% A/93% B (1 CV), 7% A/93% B→40% A/60% B (10 CV), 40% A/60% B (2 CV); flow rate: 100 mL/min; monitored at 254 and 280 nm] to afford benzosuberene ester 47 (51.8 mg, 0.13 mmol, 35%) as a colorless oil. $^1$H NMR (600 MHz, CDCl$_3$) δ 7.03 (1H, d, J=8.4 Hz), 6.76 (1H, d, J=9 Hz), 6.47 (2H, s), 6.37 (1H, t, J=7.8 Hz), 4.43 (2H, q, J=7.2 Hz), 3.85 (3H, s), 3.84 (3H, s), 3.79 (6H, s), 2.56 (2H, t, J=6.6 Hz), 2.17 (2H, m), 1.96 (2H, m), 1.41 (3H, t, J=7.2 Hz). $^{13}$C NMR (150 MHz, CDCl$_3$) δ 168.8, 155.2, 153.0, 142.3, 140.2, 138.1, 137.5, 133.2, 131.6, 127.7, 123.4, 108.6, 105.2, 61.4, 61.0, 56.3, 55.9, 34.9, 29.6, 25.3, 14.4. HRMS: Obsvd 435.1778 [M+Na$^+$], Calcd for C$_{24}$H$_{28}$O$_6$Na: 435.1778. HPLC: 22.42 min.

(3-Methoxy-9-(3,4,5-trimethoxyphenyl)-6,7-dihydro-5H-benzo[7]annulen-4-yl)methanol (48)

Ester 47 (0.12 g, 0.28 mmol) was dissolved in THF (10 mL), and the solution was cooled to 0° C. LiAlH$_4$ (77 μL, 4 M in ether, 0.31 mmol) was added to the solution dropwise, and the reaction mixture was stirred while warming to room temperature for 1 h. The reaction mixture was washed with water and extracted with EtOAc (3×20 mL). The combined organic phase was dried over sodium sulfate and evaporated under reduced pressure. The crude reaction product was purified by flash chromatography using a pre-packed 50 g silica column [solvent A: EtOAc; solvent B: hexanes; gradient: 12% A/88% B (1 CV), 12% A/88% B→60% A/40% B (10 CV), 60% A/40% B (2 CV); flow rate: 100 mL/min; monitored at 254 and 280 nm] to afford benzyl alcohol 48 (54.3 mg, 0.15 mmol, 52%) as a white solid. $^1$H NMR (600 MHz, CDCl$_3$) δ 6.97 (1H, d, J=9 Hz), 6.75 (1H, d, J=9 Hz), 6.50 (2H, s), 6.35 (1H, t, J=7.8 Hz), 4.87 (2H, s), 3.89 (3H, s), 3.86 (3H, s), 3.81 (6H, s), 2.79 (2H, t, J=7.2 Hz), 2.16 (2H, p, J=7.2 Hz), 1.92 (2H, m). $^{13}$C NMR (150 MHz, CDCl$_3$) δ 157.1, 153.1, 143.3, 142.4, 138.5, 137.5, 133.8, 130.2, 127.1, 126.0, 107.9, 105.4, 61.1, 57.7, 56.3, 55.7, 35.3, 27.6, 25.4. HRMS: Obsvd 393.1672 [M+Na$^+$], Calcd for C$_{22}$H$_{26}$O$_5$Na: 393.1672. HPLC: 19.09 min.

Figure 8:
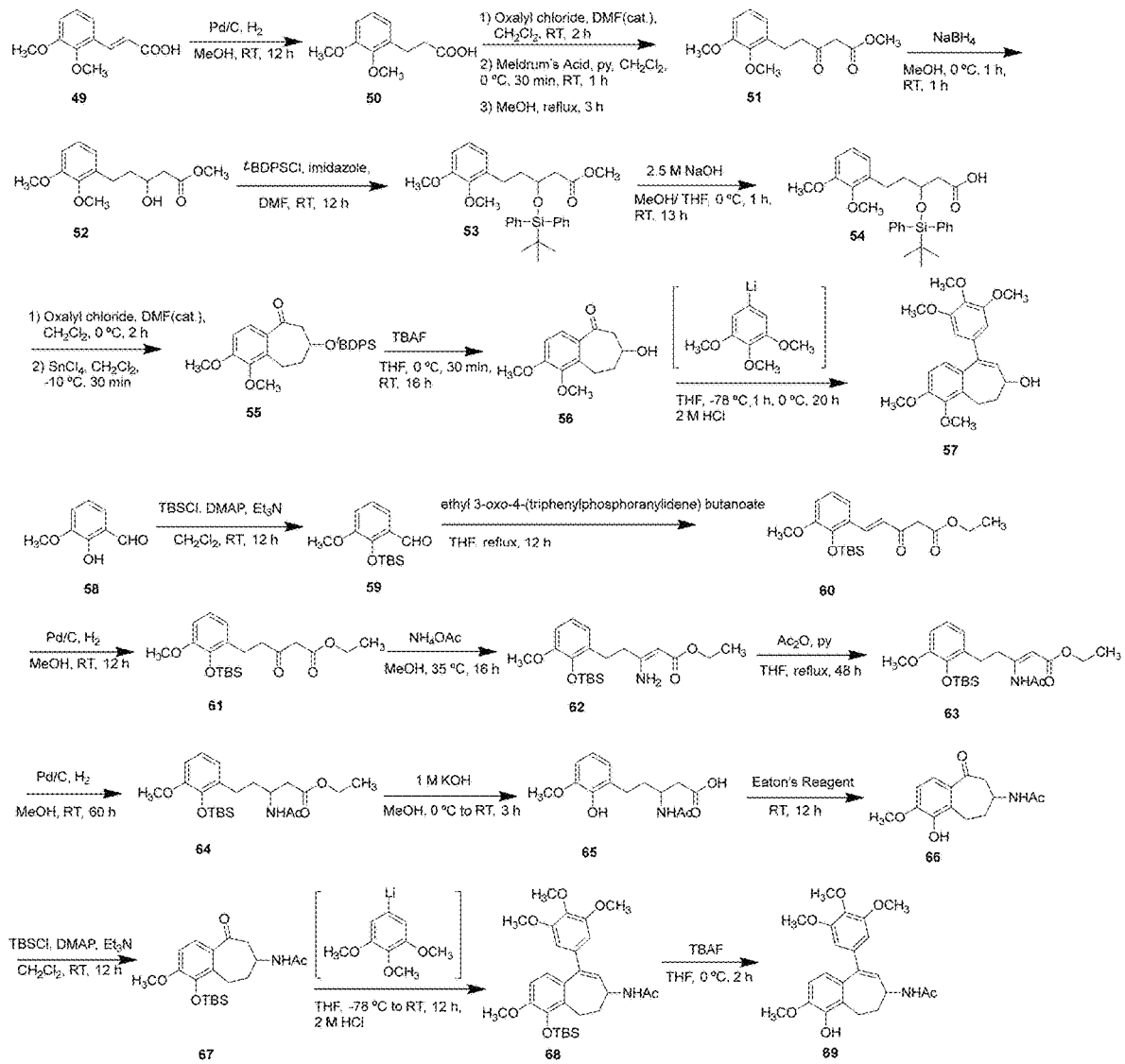
FIG. 8 shows synthetic Scheme 6 for the synthesis of representative compounds described herein.

FIG. 8 shows Scheme 6, synthesis of compounds 57 and 69. Secondary allylic alcohol 57 and its corresponding N-acetyl congener 69 (Scheme 6) were prepared to investigate structure-activity relationship correlations associated with heteroatom incorporation on the conformationally flexible fused seven-membered ring. Appropriate aldehyde chain elongations were facilitated by Meldrum's acid (towards 57) and Wittig-ylide methodology (towards 69), and subsequent functional group transformations (including installation of carboxylic acid moieties obtained under saponification conditions) afforded protected alcohol 54 and N-acetamide 65, separately. Lewis acid mediated cyclization to obtain the benzosuberone molecular core was achieved by treatment of the requisite acyl chloride with either tin tetrachloride (to obtain ketone 55) or Eaton's reagent (to obtain ketone 66). In each case, the pendant ring was installed through reaction with 3,4,5-trimethoxyphenyl-lithium. The secondary alcohol moiety (target compound 57) was revealed (by deprotection) prior to the organolithium step, while the phenolic moiety (target compound 69) was revealed after the organolithium reaction (Scheme 6). Both compounds 56 and 57 undergo elimination first (allylic alcohol), then demethylation if treated with a Lewis acid such as AlCl$_3$ or BCl$_3$.

S 3-(2,3-Dimethoxyphenyl)propanoic acid (50)

To cinnamic acid 49 (5.0 g, 24 mmol) was added methanol (50 mL) and 10% Pd/C (0.8 g). Two hydrogen balloons were installed through the rubber septum, and the reaction mixture was stirred at room temperature for 4 h. The reaction mixture was filtered through Celite®, and the Celite® was washed with EtOAc (3×50 mL). The organic solvents (CH$_3$OH and EtOAc) were evaporated under reduced pressure to afford carboxylic acid 50 (5.0 g, 24 mmol, quantitative) as a white solid. No further purification was needed. $^1$H NMR (600 MHz, CDCl$_3$) δ 6.98 (1H, t, J=7.8 Hz), 6.78 (2H, m), 3.86 (3H, s), 3.84 (3H, s), 2.95 (2H, t, J=7.8 Hz), 2.66 (2H, t, J=7.8 Hz). $^{13}$C NMR (150 MHz, CDCl$_3$) δ 178.9, 152.8, 147.2, 134.1, 124.1, 121.8, 110.9, 60.7, 55.8, 34.8, 25.4.

Methyl 5-(2,3-dimethoxyphenyl)-3-oxopentanoate (51)

To dissolved carboxylic acid 50 (5.05 g, 24.0 mmol) in dichloromethane (96 mL) were added oxalyl chloride (4.12 mL, 47.2 mmol) and a catalytic amount of DMF (0.15 mL). The reaction mixture was stirred at room temperature for 1 h, at which time an additional catalytic amount of DMF (0.15 mL) was added, and the reaction solution stirred for 1 h at room temperature. The solvent and unreacted oxalyl chloride were removed under reduced pressure to afford acyl chloride as a yellow crystalline solid, which was re-dissolved in dichloromethane (50 mL) and cooled to 0° C. Meldrum's acid (3.47 g, 24.1 mmol) and pyridine (4.33 mL, 53.8 mmol) were added, and the reaction mixture was stirred for 30 min at 0° C., then 1 h at room temperature. The mixture was diluted with dichloromethane (50 mL), and washed with 2 M HCl (20 mL), followed by brine (30 mL). The organic layer was dried over sodium sulfate and concentrated in vacuo. The residue was dissolved in $CH_3OH$ (50 mL) and heated at reflux for 3 h. The solvent was removed under reduced pressure. The crude product was purified by flash chromatography using a pre-packed 100 g silica column [solvent A: EtOAc; solvent B: hexanes; gradient: 7% A/93% B (1 CV), 7% A/93% B→60% A/40% B (10 CV), 60% A/40% B (2 CV); flow rate: 40 mL/min; monitored at 254 and 280 nm] to afford the ester 51 (3.57 g, 13.4 mmol, 56%) as a pale-yellow oil. $^1H$ NMR (600 MHz, $CDCl_3$) δ 6.96 (1H, t, J=7.8 Hz), 6.77 (1H, d, J=9 Hz), 6.74 (1H, d, J=7.8 Hz), 3.84 (3H, s), 3.81 (3H, s), 3.71 (3H, s), 3.44 (2H, s), 2.89 (2H, m), 2.83 (2H, m). $^{13}C$ NMR (150 MHz, $CDCl_3$) δ 202.1, 167.6, 152.7, 147.0, 134.2, 124.0, 121.8, 110.6, 60.5, 55.6, 52.3, 49.0, 43.6, 24.2.

Methyl
5-(2,3-dimethoxyphenyl)-3-hydroxypentanoate (52)

To a well-stirred solution of ketone 51 (0.50 g, 1.9 mmol) in $CH_3OH$ (8 mL) at 0° C., sodium borohydride (24 mg, 0.63 mmol) was added in one aliquot. The reaction mixture was initially stirred at 0° C. for 1 h, and then stirred at room temperature for another 1 h. The solvent was removed under reduced pressure. The residue was washed with water (10 mL) and extracted with diethyl ether (3×10 mL). The combined organic phase was dried over sodium sulfate and concentrated under reduced pressure. The crude product was purified by flash chromatography using a prepacked 50 g silica column [solvent A: EtOAc; solvent B: hexanes; gradient: 7% A/93% B (3 CV), 7% A/93% B→60% A/40% B (10 CV), 60% A/40% B (1 CV); flow rate: 40 mL/min; monitored at 254 and 280 nm] to afford alcohol 52 (0.40 g, 1.5 mmol, 79%). $^1H$ NMR (600 MHz, $CDCl_3$) δ 6.98 (1H, t, 7.8 Hz), 6.78 (2H, m), 3.97 (1H, m), 3.85 (3H, s), 3.82 (3H, s), 3.69 (3H, s), 2.76 (2H, t, J=7.8 Hz), 2.48 (2H, m), 1.78 (2H, m). $^{13}C$ NMR (150 MHz, $CDCl_3$) δ 173.3, 152.8, 147.2, 135.4, 124.2, 122.1, 110.5, 67.2, 60.8, 55.8, 51.8, 41.4, 37.6, 25.9.

Methyl 3-((tert-butyldiphenylsilyl)oxy)-5-(2,3-dimethoxyphenyl)pentanoate (53)

To a solution of alcohol 52 (0.38 g, 0.14 mmol) and imidazole (0.16 g, 2.3 mmol) in DMF (2.6 mL) at room temperature was added TBDPSCl (0.55 mL, 2.1 mmol) in one aliquot. The reaction mixture was stirred for 14 h, diluted with brine (10 mL), and extracted with $Et_2O$ (3×10 mL). The organic extracts were combined and dried over sodium sulfate, filtered, concentrated under reduced pressure, and purified by flash chromatography using a pre-packed 25 g silica column [solvent A: EtOAc; solvent B: hexanes; gradient: 7% A/93% B (1 CV), 7% A/93% B→30% A/70% B (10 CV), 30% A/70% B (2 CV); flow rate: 75 mL/min; monitored at 254 and 280 nm] to afford ester 53 (0.35 g, 0.69 mmol, 49%) as a colorless oil. $^1H$ NMR (600 MHz, $CDCl_3$) δ 7.72 (3H, m), 7.67 (1H, m), 7.38 (6H, m), 6.91 (1H, t, J=7.8 Hz), 6.73 (1H, d, J=9.6 Hz), 6.55 (1H, d, J=9 Hz), 4.29 (1H, m), 3.83 (3H, s), 3.71 (3H, s), 3.54 (3H, s), 2.58 (4H, m), 1.76 (2H, m), 1.06 (9H, s). $^{13}C$ NMR (150 MHz, $CDCl_3$) δ 172.0, 152.8, 147.1, 136.1, 136.0, 135.9, 135.3, 134.9, 134.2, 134.1, 129.8, 129.7, 127.9, 127.7, 127.6, 123.9, 121.8, 110.2, 70.5, 60.7, 55.8, 51.5, 41.9, 38.2, 27.1, 26.7, 25.4.

3-((Tert-butyldiphenylsilyl)oxy)-5-(2,3-dimethoxyphenyl)pentanoic Acid (54)

To a solution of ester 53 (0.67 g, 1.3 mmol) in $CH_3OH$/THF (2.2 mL/1.1 mL) at 0° C. was added 2.5 M NaOH (1.76 mL). The reaction mixture was stirred for 1 h at 0° C., and then 13 h at room temperature, acidified by 2 M HCl (10 mL), and extracted with $Et_2O$ (3×10 mL). The organic extracts were combined and dried over sodium sulfate, filtered, concentrated under reduced pressure, and purified by flash chromatography using a pre-packed 25 g silica column [solvent A: EtOAc; solvent B: hexanes; gradient: 7% A/93% B (1 CV), 7% A/93% B→30% A/70% B (10 CV), 30% A/70% B (2 CV); flow rate: 75 mL/min; monitored at 254 and 280 nm] to afford carboxylic acid 54 (0.26 g, 0.53 mmol, 40%) as a colorless oil. $^1H$ NMR (600 MHz, $CDCl_3$) δ 7.67 (4H, m), 7.41 (6H, m), 6.89 (1H, t, J=8.4 Hz), 6.72 (1H, d, J=8.4 Hz), 6.52 (1H, m), 4.20 (1H, m), 3.83 (3H, s), 3.69 (3H, s), 2.50 (4H, m), 1.80 (2H, m), 1.06 (9H, s). $^{13}C$ NMR (150 MHz, $CDCl_3$) δ 152.6, 146.94, 146.93, 135.9, 135.8, 129.9, 129.8, 129.77, 127.7, 127.6, 123.81, 123.80, 121.6, 110.2, 70.2, 60.5, 55.6, 40.8, 37.6, 26.9, 25.3, 19.3.

7-((Tert-butyldiphenylsilyl)oxy)-1,2-dimethoxy-6,7,8,9-tetrahydro-5H-benzo[7]annulen-5-one (55)

To a solution of carboxylic acid 54 (5.37 g, 10.9 mmol) in dichloromethane (40 mL) was added oxalyl chloride (4.5 mL, 52 mmol) and 3 drops of DMF as catalyst at room temperature. The resultant reaction mixture was stirred for 2 h. The solvent and unreacted oxalyl chloride were removed under reduced pressure. The residue acyl chloride was dissolved in dichloromethane (50 mL). The solution was cooled to −10° C., at which point $SnCl_4$ (3.63 mL, 1 M in $CH_2Cl_2$, 3.63 mmol) was added, followed by stirring at −10° C. for 1 h. The reaction was quenched with cold water and extracted with EtOAc (3×50 mL). The organic extracts were combined and dried over sodium sulfate, filtered, concentrated under reduced pressure, and purified by flash chromatography using a pre-packed 100 g silica column [solvent A: EtOAc; solvent B: hexanes; gradient: 7% A/93% B (1 CV), 7% A/93% B→40% A/60% B (10 CV), 40% A/60% B (2 CV); flow rate: 75 mL/min; monitored at 254 and 280 nm] to afford cyclized ketone 55 (2.80 g, 5.90 mmol, 54%) as a colorless oil. $^1H$ NMR (600 MHz, $CDCl_3$) δ 7.63 (4H, m), 7.56 (1H, d, J=8.4 Hz), 7.39 (6H, m), 6.81 (1H, d, J=9 Hz), 6.29 (1H, m), 3.90 (3H, s), 3.78 (3H, s), 3.17 (1H, m), 3.03 (2H, m), 2.88 (1H, m), 1.98 (1H, m), 1.84 (1H, m), 1.03 (9H, s). $^{13}C$ NMR (150 MHz, $CDCl_3$) δ 199.5, 155.8, 146.2, 137.9, 136.0, 135.9, 134.1, 133.9, 133.1, 129.9, 129.8, 127.81, 127.77, 125.7, 109.6, 68.3, 60.9, 55.9, 50.4, 36.2, 27.0, 21.3, 19.3.

7-Hydroxy-1,2-dimethoxy-6,7,8,9-tetrahydro-5H-benzo[7]annulen-5-one (56)

To a solution of ketone 55 (0.73 g, 1.5 mmol) in THF (10 mL) was added TBAF (3.1 mL 1 M in THF, 3.1 mmol), and the reaction mixture was stirred for 30 min at 0° C. and 16 h at room temperature. The reaction was quenched with brine (10 mL) and extracted with EtOAc (3×20 mL). The organic extracts were combined and dried over sodium sulfate, filtered, concentrated under reduced pressure, and purified by flash chromatography using a pre-packed 50 g silica column [solvent A: EtOAc; solvent B: hexanes; gradient: 12% A/88% B (1 CV), 12% A/88% B→20% A/80% B (10 CV), 20% A/80% B (2 CV); flow rate: 75 mL/min; monitored at 254 and 280 nm] to afford alcohol 56 (0.16 g, 0.66 mmol, 49%) as a yellow oil. $^1$H NMR (600 MHz, CDCl$_3$) δ 7.60 (1H, d, J=8.4 Hz), 6.84 (1H, d, J=8.4 Hz), 4.33 (1H, m), 3.91 (3H, s), 3.80 (3H, s), 3.08 (3H, m), 2.99 (1H, m), 1.89 (2H, m). $^{13}$C NMR (150 MHz, CDCl$_3$) δ 199.3, 156.0, 146.3, 137.7, 132.6, 125.8, 109.8, 67.3, 60.9, 56.0, 50.3, 35.8, 21.4.

3,4-Dimethoxy-9-(3,4,5-trimethoxyphenyl)-6,7-dihydro-5H-benzo[7]annulen-7-ol (57)

To a solution of 3, 4, 5-trimethoxyphenyl bromide (0.49 g, 2.0 mmol) in THF (20 mL) at −78° C. was added n-BuLi (1.85 mL, 1.6 M in hexanes, 2.98 mmol), and the reaction mixture was stirred for 1 h. Benzosuberone 56 (0.16 g, 0.66 mmol) in THF (5 mL) was added slowly. The reaction mixture was stirred at 0° C. for 20 h. 2 M HCl (20 mL) was added, and the mixture was extracted with EtOAc (4×20 mL). The combined organic phase was further washed by brine and dried over sodium sulfate, filtered, and concentrated under reduced pressure and purified by flash chromatography using a pre-packed 25 g silica column [solvent A: EtOAc; solvent B: hexanes; gradient: 12% A/88% B (1 CV), 12% A/88% B→80% A/20% B (10 CV), 80% A/20% B (2 CV); flow rate: 100 mL/min; monitored at 254 and 280 nm] to afford alcohol 57 (0.10 g, 0.26 mmol, 39%) as a brown solid. $^1$H NMR (600 MHz, CDCl$_3$) δ 6.75 (2H, m), 6.51 (2H, s), 6.28 (1H, d, J=4.8 Hz), 4.18 (1H, m), 3.877 (3H, s), 3.875 (3H, s), 3.86 (3H, s), 3.80 (6H, s), 3.16 (1H, m), 2.53 (1H, m), 2.43 (1H, m), 2.15 (1H, m). $^{13}$C NMR (150 MHz, CDCl$_3$) δ 153.1, 152.0, 146.1, 139.4, 137.8, 137.4, 135.7, 132.9, 131.5, 125.5, 109.6, 105.5, 70.0, 61.4, 61.1, 56.3, 55.8, 43.2, 22.4. HRMS: Obsvd 409.1621 [M+Na$^+$], Calcd for C$_{22}$H$_{26}$O$_6$Na: 409.1622. HPLC: 16.79 min.

2-((Tert-butyldimethylsilyl)oxy)-3-methoxybenzaldehyde (59)

To a well-stirred solution of 2-hydroxy-3-methoxybenzaldehyde 58 (0.50 g, 3.3 mmol) in dichloromethane (30 mL) was added TBSCl (0.74 g, 4.9 mmol), DMAP (0.12 g, 0.99 mmol), and Et$_3$N (0.69 mL, 4.9 mmol). The reaction mixture was stirred for 12 h at room temperature, at which point brine (50 mL) was added, and the reaction mixture was extracted with dichloromethane (3×40 mL). The organic extracts were combined and dried over sodium sulfate, filtered, concentrated under reduced pressure, and purified by flash chromatography using a pre-packed 50 g silica column [solvent A: EtOAc; solvent B: hexanes; gradient: 7% A/93% B (1 CV), 7% A/93% B→40% A/60% B (10 CV), 40% A/60% B (2 CV); flow rate: 75 mL/min; monitored at 254 and 280 nm] to afford protected aldehyde 59 (0.50 g, 1.86 mmol, 57%) as a pale yellow oil. $^1$H NMR (600 MHz, CDCl$_3$) δ 10.51 (1H, s), 7.36 (1H, d, J=7.8 Hz), 7.03 (1H, d, J=7.8 Hz), 6.94 (1H, t, J=8.4 Hz), 3.81 (3H, s), 0.99 (9H, s), 0.20 (6H, s). $^{13}$C NMR (150 MHz, CDCl$_3$) δ 190.4, 150.8, 149.2, 127.9, 121.2, 119.1, 117.0, 55.2, 26.0, 19.0, 4.1.

Ethyl 5-(2-((tert-butyldimethylsilyl)oxy)-3-methoxyphenyl)-3-oxopent-4-enoate (60)

To dissolved ethyl 3-oxo-4-(triphenylphophoranylidene) butanoate (3.22 g, 8.26 mmol) in THF (20 mL) was added protected aldehyde 59 (2.2 g, 8.3 mmol), and the reaction mixture was heated at reflux and stirred for 17 h. The solvent was removed under reduced pressure, and the residue was taken up as a slurry and purified by flash chromatography using a pre-packed 100 g silica column [solvent A: EtOAc; solvent B: hexanes; gradient: 12% A/88% B (1 CV), 12% A/88% B→40% A/60% B (10 CV), 40% A/60% B (2 CV); flow rate: 100 mL/min; monitored at 254 and 280 nm] to afford ester 60 (2.50 g, 6.59 mmol, 80%) as an off white solid. NMR characterization was conducted after the next step.

Ethyl 5-(2-((tert-butyldimethylsilyl)oxy)-3-methoxyphenyl)-3-oxopentanoate (61)

To dissolved ester 60 (2.50 g, 6.59 mmol) in methanol (60 mL) was added 10% palladium on carbon (0.54 g), and hydrogen gas was introduced with a balloon. The reaction mixture was stirred at room temperature for 12 h and filtered through Celite®, and the Celite® was washed with EtOAc (3×40 mL). The combined organic phase (CH$_3$OH and EtOAc) was evaporated under reduced pressure. The resulting organic material was purified by flash chromatography using a pre-packed 100 g silica column [solvent A: EtOAc; solvent B: hexanes; gradient: 7% A/93% B (1 CV), 7% A/93% B→40% A/60% B (10 CV), 40% A/60% B (2 CV); flow rate: 100 mL/min; monitored at 254 and 280 nm] to afford saturated ester 61 (1.15 g, 3.02 mmol, 46%) as a light-yellow oil. $^1$H NMR (600 MHz, CDCl$_3$) δ 6.81 (1H, m), 6.71 (1H, d, J=7.8 Hz), 4.16 (2H, q, J=7.2 Hz), 3.76 (3H, s), 3.39 (2H, s), 2.90 (2H, m), 2.83 (2H, m), 1.25 (3H, t, J=7.2 Hz), 0.98 (9H, s), 0.18 (6H, s). $^{13}$C NMR (150 MHz, CDCl$_3$) δ 202.3, 167.2, 150.0, 142.8, 131.8, 121.9, 121.0, 109.7, 61.4, 54.8, 49.4, 43.2, 26.2, 24.8, 18.9, 14.2, −3.7.

Ethyl (Z)-3-amino-5-(2-((tert-butyldimethylsilyl)oxy)-3-methoxyphenyl)pent-2-enoate (62)

To keto-ester 61 (1.10 g, 2.89 mmol) dissolved in methanol (15 mL) was added dry ammonium acetate (1.11 g, 14.5 mmol). The reaction mixture was stirred at 35° C. for 16 h. The methanol was removed under vacuum, and the residue was suspended in EtOAc (30 mL) and filtered. The filtrate was washed with EtOAc (4×20 mL). The combined organic layer was dried over sodium sulfate and concentrated under reduced pressure to afford amine 62 (1.02 g, 2.69 mmol, 93%) as pale yellow crystals. No further purification was performed. $^1$H NMR (600 MHz, CDCl$_3$) δ 6.82 (1H, m), 6.72 (2H, m), 4.58 (1H, s), 4.11 (2H, m), 3.78 (3H, s), 2.87 (2H, m), 2.40 (2H, m), 1.26 (3H, t, J=7.2 Hz), 1.00 (9H, s), 0.19 (6H, s). $^{13}$C NMR (150 MHz, CDCl$_3$) δ 170.7, 163.6, 150.0, 142.8, 131.8, 122.0, 121.1, 109.8, 83.5, 58.7, 54.8, 36.7, 29.3, 26.3, 19.0, 14.7, −3.6.

Ethyl (Z)-3-acetamido-5-(2-((tert-butyldimethylsilyl)oxy)-3-methoxyphenyl)pent-2-enoate (63)

To amine 62 (4.02 g, 10.6 mmol) dissolved in THF (50 mL) was added pyridine (1.71 mL, 21.2 mmol) and acetic anhydride (6.00 mL, 63.6 mmol). The reaction mixture was stirred for 48 h under reflux. The THF was removed under vacuum, and the residue was dissolved in EtOAc (50 mL)

and washed with water (50 mL), 2 M HCl (20 mL), saturated NaHCO$_3$ (50 mL) and brine (50 mL). The combined organic layer was dried over sodium sulfate and concentrated under reduced pressure. The resulting organic material was purified by flash chromatography using a pre-packed 100 g silica column [solvent A: EtOAc; solvent B: hexanes; gradient: 7% A/93% B (1 CV), 7% A/93% B→40% A/60% B (10 CV), 40% A/60% B (2 CV); flow rate: 100 mL/min; monitored at 254 and 280 nm] to afford N-acetamide 63 (2.17 g, 5.15 mmol, 49%) as a yellow oil. $^1$H NMR (600 MHz, CDCl$_3$) δ 6.80 (2H, m), 6.70 (1H, m), 4.90 (1H, s), 4.14 (2H, m), 3.76 (3H, s), 3.00 (2H, m), 2.86 (2H, m), 2.15 (3H, s), 1.26 (3H, m), 0.98 (9H, s), 0.17 (6H, s). $^{13}$C NMR (150 MHz, CDCl$_3$) δ 169.3, 168.3, 158.2, 149.8, 142.7, 132.0, 122.2, 120.9, 109.5, 96.2, 59.8, 54.7, 34.5, 28.7, 26.2, 25.3, 18.9, 14.3, −3.8.

Ethyl 3-acetamido-5-(2-((tert-butyldimethylsilyl)oxy)-3-methoxyphenyl)pentanoate (64)

Unsaturated N-acetamide 63 (2.17 g, 5.15 mmol) was dissolved in CH$_3$OH (30 mL). Palladium (10%) on carbon (0.53 g) and a hydrogen gas balloon were introduced, and the solution was stirred at room temperature for 60 h and filtered through Celite®. The Celite® was washed with EtOAc (3×50 mL). The combined organic phase (CH$_3$OH and EtOAc) was evaporated under reduced pressure. The resulting organic material was purified by flash chromatography using a pre-packed 100 g silica column [solvent A: EtOAc; solvent B: hexanes; gradient: 7% A/93% B (1 CV), 7% A/93% B→50% A/50% B (10 CV), 50% A/50% B (2 CV); flow rate: 100 mL/min; monitored at 254 and 280 nm] to afford saturated N-acetamide 64 (0.96 g, 2.3 mmol, 44%) as a colorless oil. $^1$H NMR (600 MHz, CDCl$_3$) δ 6.83 (1H, t, J=7.8 Hz), 6.71 (2H, m), 6.03 (1H, d, J=9 Hz), 4.29 (1H, m), 4.11 (2H, q, J=7.2 Hz), 3.77 (3H, s), 2.74 (1H, m), 2.62 (1H, m), 2.59 (1H, m), 2.51 (1H, m), 1.96 (3H, s), 1.82 (2H, m), 1.24 (3H, t, J=7.2 Hz), 1.00 (9H, s), 0.17 (6H, d, J=10.8 Hz). $^{13}$C NMR (150 MHz, CDCl$_3$) δ 172.1, 169.6, 150.0, 142.7, 132.7, 121.9, 121.0, 109.4, 60.7, 54.8, 46.3, 38.8, 34.3, 27.6, 26.3, 23.7, 19.0, 14.3, −3.6, −3.7.

3-Acetamido-5-(2-hydroxy-3-methoxyphenyl)pentanoic acid (65)

To dissolved unsaturated ester 64 (0.96 g, 2.3 mmol) in methanol (5 mL) was added 1 M KOH (7.48 mL). The reaction was stirred from 0° C. to room temperature over 3 h. The methanol was removed under vacuum, and 2 M HCl (5 mL) was added to the residue, which was then extracted with EtOAc (3×20 mL). The combined organic phase was evaporated under reduced pressure. The resulting organic material was purified by flash chromatography using a pre-packed 100 g silica column [solvent A: EtOAc; solvent B: hexanes; gradient: 12% A/88% B (1 CV), 12% A/88% B→100% A/0% B (35 CV), 100% A/0% B (2 CV); flow rate: 100 mL/min; monitored at 254 and 280 nm] to afford carboxylic acid 65 (0.38 g, 1.8 mmol, 58%) as a colorless oil. $^1$H NMR (600 MHz, CDCl$_3$) δ 6.74 (3H, m), 6.34 (1H, d, J=9 Hz), 4.25 (1H, m), 3.85 (3H, s), 2.64 (4H, m), 1.97 (3H, s), 1.91 (2H, m). $^{13}$C NMR (150 MHz, CDCl$_3$) δ 175.6, 171.0, 146.6, 143.5, 127.3, 122.5, 119.8, 108.9, 56.2, 46.7, 38.9, 34.1, 26.8, 23.5.

N-(1-hydroxy-2-methoxy-5-oxo-6,7,8,9-tetrahydro-5H-benzo[7]annulen-7-yl)acetamide (66)

Carboxylic acid 65 (0.70 g, 2.5 mmol) was dissolved in Eaton's reagent (14 mL), and the reaction mixture was stirred at room temperature for 12 h. Ice was added to the reaction mixture, which generated a significant amount of heat. A saturated sodium carbonate solution was added until neutral pH was achieved. The mixture was extracted with dichloromethane (4×30 mL). The organic phase was further washed by brine and dried over sodium sulfate, filtered, and concentrated under reduced pressure and purified by flash chromatography using a pre-packed 50 g silica column [solvent A: CH$_3$OH; solvent B: CH$_2$Cl$_2$; gradient: 1% A/99% B (1 CV), 1% A/99% B→10% A/90% B (10 CV), 10% A/90% B (2 CV); flow rate: 100 mL/min; monitored at 254 and 280 nm] to afford cyclized ketone 66 (0.37 g, 1.4 mmol, 57%) as a yellow oil. $^1$H NMR (600 MHz, CDCl$_3$) δ 7.34 (1H, d, J=8.4 Hz), 6.79 (1H, d, J=9 Hz), 5.91 (1H, s), 4.48 (1H, m), 3.94 (3H, s), 3.23 (1H, m), 3.13 (1H, m), 2.83 (2H, m), 2.73 (1H, m), 2.44 (1H, m), 1.96 (3H, s). $^{13}$C NMR (150 MHz, CDCl$_3$) δ 201.1, 169.6, 149.3, 142.9, 133.1, 129.0, 121.1, 108.2, 56.3, 47.0, 45.7, 32.9, 23.6, 22.6.

N-(1-((tert-butyldimethylsilyl)oxy)-2-methoxy-5-oxo-6,7,8,9-tetrahydro-5H-benzo[7]annulen-7-yl)acetamide (67)

To a solution of cyclized ketone 66 (0.37 g, 1.4 mmol) in dichloromethane (20 mL) at room temperature was added TBSCl (0.32 g, 2.1 mmol), DMAP (52 mg, 0.42 mmol) and trimethylamine (0.30 mL, 2.1 mmol), and the resultant reaction mixture was stirred for 12 h. The reaction mixture was subsequently washed with brine (30 mL), and extracted with dichloromethane (3×40 mL). The combined organic layer was dried over sodium sulfate and concentrated under reduced pressure. The resulting organic material was purified by flash chromatography using a pre-packed 50 g silica column [solvent A: CH$_3$OH; solvent B: CH$_2$Cl$_2$; gradient: 0% A/100% B (1 CV), 0% A/100% B→5% A/95% B (10 CV), 5% A/95% B (2 CV); flow rate: 100 mL/min; monitored at 254 and 280 nm] to afford protected ketone 67 (0.36 g, 0.95 mmol, 68%) as off-white solid. $^1$H NMR (600 MHz, CDCl$_3$) δ 7.41 (1H, d, J=8.4 Hz), 6.78 (1H, d, J=9 Hz), 5.61 (1H, br), 4.46 (1H, m), 3.84 (3H, s), 3.26 (1H, m), 3.16 (1H, m), 2.80 (2H, m), 2.71 (1H, m), 2.45 (1H, m), 1.96 (3H, s), 1.00 (9H, s), 0.17 (6H, d, J=14.4 Hz). $^{13}$C NMR (150 MHz, CDCl$_3$) δ 201.1, 169.6, 153.4, 142.4, 134.7, 129.0, 122.6, 109.1, 55.1, 46.9, 45.8, 40.0, 33.2, 26.2, 23.6, 19.1, −3.7, −3.8.

N-(1-((tert-butyldimethylsilyl)oxy)-2-methoxy-5-(3,4,5-trimethoxyphenyl)-6,7,8,9-tetrahydro-5H-benzo[7]annulen-7-yl)acetamide (68)

To an oven-dried flask, THF (20 mL) and 3, 4, 5-trimethoxyphenyl bromide (0.16 g, 0.64 mmol) were added, and the solution was cooled to −78° C. n-BuLi (1.6 M, 0.59 mL, 0.94 mmol) was added to the reaction mixture slowly, which was then stirred at −78° C. for 45 min. Benzosuberone 67 (80 mg, 0.21 mmol) was then added dropwise to the flask, and the reaction mixture was stirred while warming from −78° C. to room temperature over 12 h. 2 M HCl (20 mL) was added, and the reaction mixture was stirred for 30 min, then extracted with EtOAc (3×50 mL). The combined organic phase was dried over sodium sulfate and evaporated under reduced pressure. The crude reaction product was purified by flash chromatography using a pre-packed 20 g silica column [solvent A: EtOAc; solvent B: hexanes; gradient: 12% A/88% B (1 CV), 12% A/88% B→100% A/0% B (10 CV), 100% A/0% B (2 CV); flow rate: 100 mL/min; monitored at 254 and 280 nm] to afford cross-coupling product benzosuberene 68 (63.6 mg, 0.120 mmol, 57%) as a crystalline white solid. $^1$H NMR (600 MHz, CDCl$_3$) δ 6.68 (1H, d, J=9 Hz), 6.58 (1H, d, J=8.4 Hz), 6.47 (2H, s), 5.98 (1H, d, J=6 Hz), 5.54 (1H, d, J=8.4 Hz, br), 4.39 (1H, m), 3.85 (3H, s), 3.80 (3H, s), 3.79 (9H, s), 3.20-2.46 (4H, m), 1.95 (3H, s), 1.03 (9H, s), 0.25 (3H, s), 0.22 (3H). $^{13}$C NMR (150 MHz, CDCl$_3$) δ 169.0, 152.8, 149.1, 141.7, 141.5, 137.9, 137.6, 132.7, 132.3, 128.4, 122.9, 108.9, 105.4, 60.9, 56.2, 54.7, 47.8, 41.0, 26.2, 23.6, 22.9, 19.0, −3.6, −3.9.

N-(1-hydroxy-2-methoxy-5-(3,4,5-trimethoxyphenyl)-6,7,8,9-tetrahydro-5H-benzo[7]annulen-7-yl)acetamide (69)

Protected benzosuberene N-acetamide 68 (63.6 mg, 0.12 mmol) was dissolved in THF (2 mL) and cooled to 0° C. TBAF (0.24 mL, 0.24 mmol) was added, and the reaction mixture was stirred at 0° C. for 2 h. The solution was washed with water and extracted with EtOAc (3×20 mL). The combined organic phase was dried over sodium sulfate, filtered, and concentrated under reduced pressure and purified b$_2$y flash chromatography using a pre-packed 25 g silica column [solvent A: CH$_3$OH; solvent B: CH$_2$Cl$_2$; gradient: 5% A/95% B (1 CV), 10% A/90% B→10% A/90% B (10 CV), 10% A/90% B (2 CV); flow rate: 100 mL/min; monitored at 254 and 280 nm] to afford benzosuberene N-acetamide 69 (22 mg, 0.05 mmol, 44%) as a white solid. $^1$H NMR (600 MHz, CDCl$_3$) δ 6.71 (1H, d, J=9 Hz), 6.54 (1H, d, J=8.4 Hz), 6.48 (2H, s), 5.98 (1H, d, J=6 Hz), 5.76 (1H, s), 5.56 (1H, d, J=9 Hz, br), 4.38 (1H, m), 3.91 (3H, s), 3.86 (3H, s), 3.80 (6H, s), 3.17-2.43 (4H, m), 1.96 (3H, s). $^{13}$C NMR (150 MHz, CDCl$_3$) δ 169.2, 153.0, 145.7, 142.5, 141.4, 137.83, 137.75, 133.3, 128.8, 126.9, 121.5, 108.3, 105.6, 61.1, 56.4, 56.2, 48.1, 40.8, 23.8, 22.3. HRMS: Obsvd 436.1730 [M+Na$^+$], Calcd for C$_{23}$H$_{29}$NO$_6$Na: 436.1731. HPLC: 9.92 min.

Figure 9:
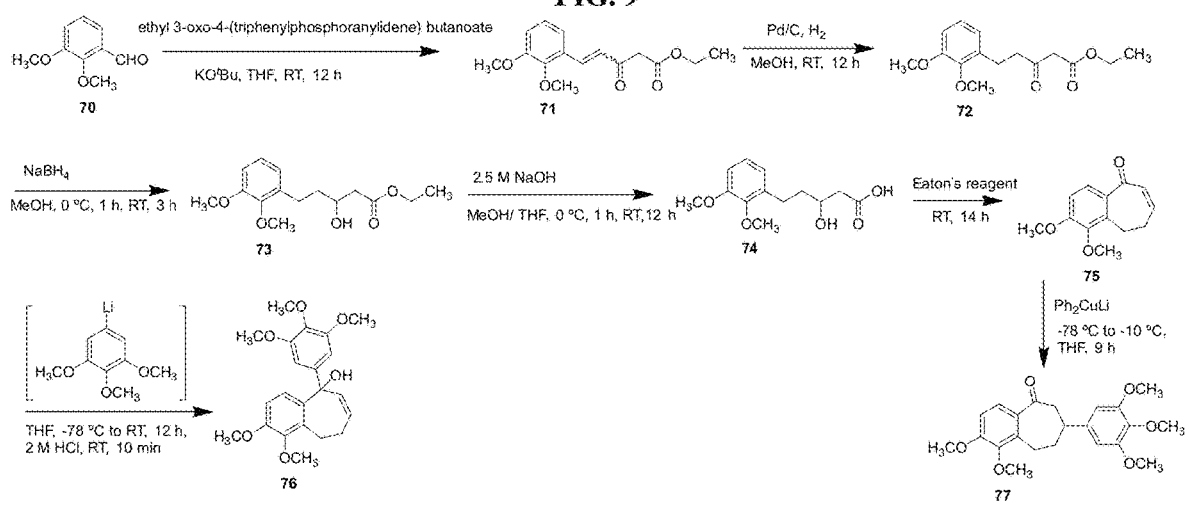
FIG. 9 shows synthetic Scheme 7 for the synthesis of representative compounds described herein.

FIG. 9 shows Scheme 7, synthesis of compounds 76 and 77. Translocation of the trimethoxyphenyl group was achieved by initial cyclization (Eaton's reagent) of carboxylic acid 74 with concomitant elimination to afford α,β-unsaturated ketone 75. With the α,β-unsaturated ketone in hand, 1,2- and 1,4-addition reactions were conducted using the appropriate aryl-lithium and Gilman reagents to provide tertiary alcohol analogue 76 (with unsaturated 7-membered ring to maintain rigidity), and separately the Michael adduct, trimethoxy pendant phenyl ring shifted analogue 77 (Scheme 7).

Ethyl 5-(2,3-dimethoxyphenyl)-3-oxopentanoate (72)

To a solution of 2, 3-dimethoxybenzaldehyde 70 (1.06 g, 6.38 mmol) in THF (50 mL) were added ethyl 3-oxo-4-(triphenylphosphoranylidene) butyrate (3.00 g, 7.65 mmol) and potassium t-butoxide (1.73 g, 15.3 mmol) at room temperature, and the reaction mixture was stirred for 12 h. The THF was removed under reduced pressure, and the resulting material was quenched with 2 M HCl (20 mL) and extracted with EtOAc (3×50 mL). The combined organic layers were evaporated under reduced pressure, and the crude product (71) was dissolved in CH$_3$OH (40 mL). To this solution was added 10% palladium on carbon (0.24 g) and balloons with hydrogen gas. The reaction mixture was stirred at room temperature for 12 h and filtered through Celite®, and the Celite® was washed with EtOAc (3×30 mL). The combined organic phase (CH$_3$OH and EtOAc) was evaporated under reduced pressure. The resulting organic material was purified by flash chromatography using a pre-packed 100 g silica column [solvent A: EtOAc; solvent B: hexanes; gradient: 7% A/93% B (1 CV), 7% A/93% B→40% A/60% B (10 CV), 40% A/60% B (2 CV); flow rate: 100 mL/min; monitored at 254 and 280 nm] to afford saturated ester 72 (1.45 g, 5.17 mmol, 81%) as a colorless oil. $^1$H NMR (600 MHz, CDCl$_3$) δ 6.97 (1H, t, J=7.8 Hz), 6.78 (1H, d, J=9 Hz), 6.75 (1H, d, J=7.8 Hz), 4.17, (2H, q, J=7.2 Hz), 3.85 (3H, s), 3.82 (3H, s), 3.43 (2H, s), 2.90 (2H, m), 2.84 (2H, m), 1.26 (3H, t, J=6.6 Hz). $^{13}$C NMR (150 MHz, CDCl$_3$) δ 202.4, 167.3, 152.9, 147.2, 134.5, 124.1, 122.0, 110.8, 61.5, 60.7, 55.8, 49.5, 43.8, 24.5, 14.2.

Ethyl 5-(2,3-dimethoxyphenyl)-3-hydroxypentanoate (73)

To a solution of ketone 72 (1.45 g, 5.17 mmol) in CH$_3$OH (20 mL) at 0° C. was added NaBH$_4$ (110 mg, 2.91 mmol), and the reaction mixture was stirred for 1 h at 0° C., then stirred for 3 h at ambient temperature. The CH$_3$OH was removed under reduced pressure, and the resulting material was washed with water and extracted with EtOAc (3×30 mL). The combined organic phase was concentrated under reduced pressure to afford crude alcohol product 73 (1.20 g, 4.25 mmol, 82%) as a colorless oil. $^1$H NMR (600 MHz, CDCl$_3$) δ 6.98 (1H, t, J=7.8 Hz), 6.78 (2H, m), 4.15 (2H, m), 3.97 (1H, m), 3.85 (3H, s), 3.83 (3H, s), 2.76 (2H, m), 2.47 (2H, m), 1.80 (1H, m), 1.72 (1H, m), 1.25 (3H, t, J=7.2 Hz). $^{13}$C NMR (150 MHz, CDCl$_3$) δ 173.0, 152.8, 147.2, 135.5, 124.2, 122.1, 110.4, 67.3, 60.8, 55.8, 41.5, 37.6, 25.9, 14.3.

5-(2,3-Dimethoxyphenyl)-3-hydroxypentanoic acid (74)

To a solution of ester 73 in CH$_3$OH/THF (8 mL/4 mL) was added a 2.5 M NaOH aqueous solution (6 mL) at 0° C., and the reaction mixture was stirred for 1 h at 0° C., then warmed to room temperature over 12 h. The CH$_3$OH and THF were removed under reduced pressure, and the resulting material was washed with water and extracted with EtOAc (3×30 mL). The combined organic extract was dried over Na$_2$SO$_4$, filtered and concentrated under pressure to afford carboxylic acid 74 (0.88 g, 3.3 mmol, 77%) as an orange oil (no further purification was needed). $^1$H NMR (600 MHz, CDCl$_3$) δ 7.00 (1H, t, J=8.4 Hz), 6.78 (1H, dd, J=6.6 Hz, 6.6 Hz), 3.92 (1H, m), 3.86 (3H, s), 3.84 (3H, s), 2.76 (2H, m), 2.51 (2H, m), 1.82 (1H, m), 1.73 (1H, m). $^{13}$C NMR (150 MHz, CDCl$_3$) δ 176.8, 152.7, 146.9, 134.9, 124.5, 122.2, 110.6, 66.9, 61.0, 55.8, 41.2, 37.6, 25.6.

1,2-Dimethoxy-8,9-dihydro-5H-benzo[7]annulen-5-one (75)

To carboxylic acid 74 (0.88 g, 3.3 mmol) was added Eaton's reagent (15.7 mL), and the mixture was stirred at room temperature for 14 h. The mixture was then poured over ice and neutralized with sodium carbonate. The aqueous layer was extracted with EtOAc (3×40 mL). The combined organic phase was dried over sodium sulfate, evaporated under reduced pressure, and purified by flash chromatography using a pre-packed 100 g silica column [solvent A: EtOAc; solvent B: hexanes; gradient: 7% A/93% B (1 CV), 7% A/93% B→30% A/70% B (10 CV), 30% A/70% B (2 CV); flow rate: 50 mL/min; monitored at 254 and 280 nm] to afford unsaturated cyclized ketone 75 (0.360 g, 1.65 mmol, 50%) as a yellow crystalline solid. $^1$H NMR (600 MHz, CDCl$_3$) δ 7.55 (1H, d, J=9 Hz), 6.83 (1H, d, J=9 Hz), 6.71 (1H, td, J=4.8 Hz, 12 Hz), 6.23 (1H, td, J=1.8 Hz, 12 Hz), 3.91 (3H, s), 3.78 (3H, s), 3.16 (2H, m), 2.55 (2H, m). $^{13}$C NMR (150 MHz, CDCl$_3$) δ 193.9, 156.2, 147.0, 145.2, 134.4, 134.3, 132.7, 126.7, 110.0, 61.2, 55.9, 29.6, 25.1.

1,2-Dimethoxy-5-(3,4,5-trimethoxyphenyl)-8,9-dihydro-5H-benzo[7]annulen-5-ol (76)

To an oven-dried flask, THF (30 mL) and 3,4,5-trimethoxyphenyl bromide (0.87 g, 3.5 mmol) were added, and the solution was cooled to −78° C. n-BuLi (1.41 mL, 2.5 M, 3.52 mmol) was slowly added to the reaction mixture, which was then stirred at −78° C. for 30 min. Unsaturated cyclized ketone 75 (0.35 g, 1.6 mmol) in THF (5 mL) was then added dropwise to the flask, and the reaction mixture was stirred while warming from −78° C. to room temperature over 12 h. The reaction mixture was washed with 2 M HCl (10 mL) and extracted with EtOAc (3×30 mL). The combined organic phase was dried over sodium sulfate and evaporated under reduced pressure. The crude reaction product was purified by flash chromatography using a pre-packed 50 g silica column [solvent A: EtOAc; solvent B: hexanes; gradient: 12% A/88% B (1 CV), 12% A/88% B→60% A/40% B (10 CV), 60% A/40% B (5 CV); flow rate: 100 mL/min; monitored at 254 and 280 nm] to afford tertiary alcohol 76 (0.457 g, 1.18 mmol, 74%) as a white solid. $^1$H NMR (600 MHz, CDCl$_3$) δ 7.54 (1H, d, J=9 Hz), 6.82 (1H, d, J=8.4 Hz), 6.59 (2H, s), 6.07 (1H, d, J=12 Hz), 5.77 (1H, td, J=1.2 Hz, 12 Hz), 3.90 (3H, s), 3.82 (3H, s), 3.78 (6H, s), 3.75 (3H, s), 3.05 (1H, m), 2.48 (1H, m), 2.43 (1H, m), 2.15 (1H, m). $^{13}$C NMR (150 MHz, CD$_3$OD) δ 153.9, 153.2, 147.5, 145.1, 141.7, 138.3, 137.2, 134.1, 130.8, 121.6, 109.9, 106.0, 78.6, 61.4, 61.1, 56.5, 56.1, 30.0, 23.4. HRMS: Obsvd 409.1622 [M+Na$^+$], Calcd for C$_{22}$H$_{26}$O$_6$Na: 409.1622. HPLC: 17.36 min.

1,2-Dimethoxy-7-(3,4,5-trimethoxyphenyl)-6,7,8,9-tetrahydro-5H-benzo[7]annulen-5-one (77)

To an oven-dried flask, THF (30 mL) and 3,4,5-trimethoxyphenyl bromide (0.47 g, 1.9 mmol) were added, and the solution was cooled to −78° C. n-BuLi (0.76 mL, 2.5 M, 1.9 mmol) was slowly added to the reaction mixture, which was stirred at −78° C. for 45 min then moved to a −10° C. bath. CuI (0.181 g, 0.95 mmol) was added in one aliquot to the flask, and the reaction mixture was stirred at −10° C. for 1 h. Unsaturated ketone 75 (0.104 g, 0.47 mmol) in THF (10 mL) was then added dropwise to the flask, and the reaction mixture was stirred while warming from −78° C. to room temperature over 7 h. A saturated NH$_4$Cl solution and ammonium hydroxide (20 mL/20 mL), were added followed by stirring for 30 min at room temperature and subsequent extraction with EtOAc (3×50 mL). The combined organic phase was dried over sodium sulfate and evaporated under reduced pressure. The crude reaction was purified by flash chromatography using a pre-packed 50 g silica column [solvent A: EtOAc; solvent B: hexanes; gradient: 5% A/95% B (1 CV), 5% A/95% B→60% A/40% B (10 CV), 60% A/40% B (2 CV); flow rate: 110 mL/min; monitored at 254 and 280 nm] to afford Michael addition ketone 77 (81.7 mg, 0.21 mmol, 44%) as a light white solid. $^1$H NMR (600 MHz, CDCl$_3$) δ 7.56 (1H, d, J=8.4 Hz), 6.88 (1H, d, J=9 Hz), 6.41 (2H, s), 3.93 (3H, s), 3.83 (6H, s), 3.824 (3H, s), 3.819 (3H, s), 3.34 (1H, td, J=4.8 Hz, 15 Hz), 3.09 (1H, m), 3.04 (1H, m), 2.94 (2H, m), 2.16 (1H, m), 1.97 (1H, m). $^{13}$C NMR (150 MHz, CDCl$_3$) δ 203.0, 156.4, 153.4, 146.1, 141.4, 136.6, 135.5, 132.5, 125.7, 110.1, 104.0, 61.3, 61.0, 56.2, 56.0, 47.9, 39.9, 34.6, 23.4. HRMS: Obsvd 409.1624 [M+Na$^+$], Calcd for C$_{22}$H$_{26}$O$_6$Na: 409.1622. HPLC: 18.77 min.

Figure 10:
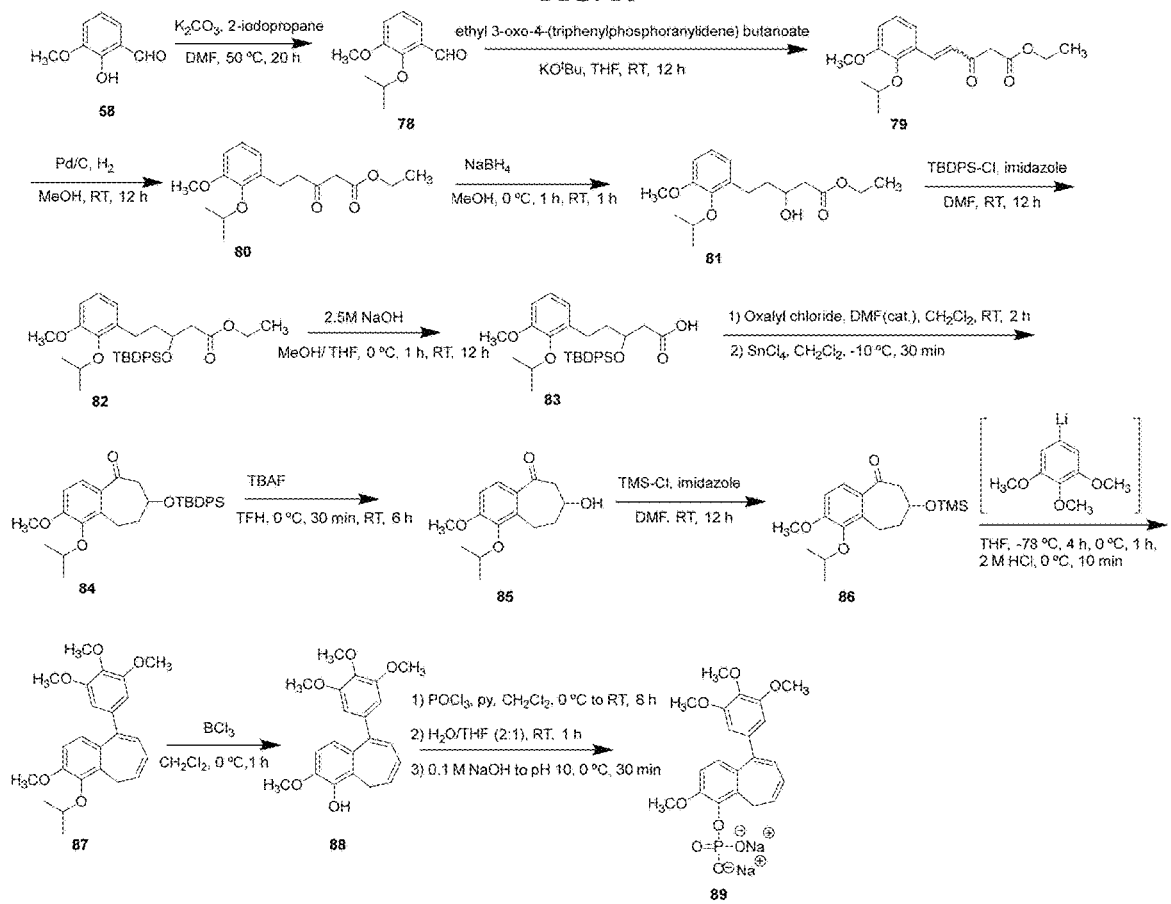
FIG. 10 shows synthetic Scheme 8 for the synthesis of representative compounds described herein.

FIG. 10 shows Scheme 8, synthesis of compounds 88 and 89. During the course of an investigation centered on variability in phenolic moiety protecting groups for a subset of benzosuberene analogues, the formation of diene 87 occurred, obtained upon 1,2-addition of trimethoxyphenyl-lithium to ketone 86, followed by reaction work-up. In this case, the secondary alcohol demonstrated a propensity to undergo elimination even under mild acidic or basic conditions such as TBAF deprotection or BCl$_3$ cleavage at lowered temperature. Various combinations of 4-position (phenolic moiety on the fused aryl ring) and allylic alcohol protecting group strategies were attempted, which eventually led to the unanticipated formation of diene 88. It is important to note that this diene (88) was previously obtained. Having this compound in hand, and noting its exceptional biological activity (inhibition of tubulin polymerization and cytotoxicity against human cancer cell lines, Table 1), motivated the preparation of the corresponding water-soluble phosphate prodrug disodium salt 89 to facilitate in vivo studies in a mouse model of prostate cancer to evaluate the efficacy of this compound as a VDA, as evidenced by bioluminescence imaging (BLI).

2-Isopropoxy-3-methoxybenzaldehyde (78)

To a solution of 2-hydroxy-3-methoxybenzaldehyde 58 (5.00 g, 32.9 mmol) in DMF (100 mL) were added K$_2$CO$_3$ (14.97 g, 98.58 mmol) and 2-iodopropane (6.54 mL, 65.7 mmol), and the reaction mixture was stirred at 50° C. for 20 h. The DMF was removed under reduced pressure, and the resulting material was washed with water (100 mL) to remove the excess salt and extracted with EtOAc (3×100 mL). The combined organic phase was dried over sodium sulfate and concentrated to afford protected aldehyde 78 (6.12 g, 31.6 mmol, 96%) as a colorless oil without further purification. $^1$H NMR (600 MHz, CDCl$_3$) δ 10.44 (1H, s), 7.41 (1H, d, J=7.8 Hz), 7.10 (2H, m), 4.62 (1H, m), 3.86 (3H, s), 1.31 (6H, d, J=6 Hz). $^{13}$C NMR (150 MHz, CDCl$_3$) δ 191.0, 153.4, 150.7, 131.0, 123.7, 119.0, 118.0, 76.3, 56.1, 22.4.

Ethyl 5-(2-isopropoxy-3-methoxyphenyl)-3-oxopent-4-enoate (79)

To dissolved ethyl 3-oxo-4-(tripheneylphosphoranylidene) butanoate (0.85 g, 2.2 mmol) in THF (50 mL) were added potassium tert-butoxide (0.50 g, 4.4 mmol) and aldehyde 78 (0.35 g, 1.8 mmol), and the resultant reaction mixture was stirred at room temperature for 12 h. The THF was removed under reduced pressure, and the resulting material was neutralized with 2 M HCl (10 mL) and extracted with EtOAc (3×20 mL). The combined organic layers were evaporated under reduced pressure, and the crude reaction product was purified by flash chromatography using a pre-packed 50 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford unsaturated ester 79 (0.40 g, 1.3 mmol, 72%) as a yellow oil. NMR characterization was conducted after the next step.

Ethyl 5-(2-isopropoxy-3-methoxyphenyl)-3-oxopentanoate (80)

To dissolved unsaturated ester 79 (0.39 g, 1.3 mmol) in $CH_3OH$ (20 mL) was added 10% palladium on carbon (0.2 g) and balloons with hydrogen gas. The reaction mixture was stirred at room temperature for 12 h, followed by filtration through Celite®, and the Celite® was washed with EtOAc (3×20 mL). The combined organic phase ($CH_3OH$ and EtOAc) was evaporated under reduced pressure to afford saturated ester 80 (0.23 g, 0.73 mmol, 57%) as a colorless oil. $^1H$ NMR (600 MHz, $CDCl_3$) δ 6.93 (1H, t, J=7.8 Hz), 6.75 (2H, m), 4.51 (1H, sept, J=6 Hz), 4.17 (2H, q, J=7.2 Hz), 3.81 (3H, s), 3.41 (2H, s), 2.92 (2H, t, J=7.8 Hz), 2.83 (2H, t, J=8.4 Hz), 1.25 (6H, d, J=6 Hz), 1.25 (3H, t, 7.2 Hz). $^{13}C$ NMR (150 MHz, $CDCl_3$) δ 202.5, 167.2, 152.9, 144.9, 135.0, 123.5, 121.9, 110.7, 74.6, 61.4, 55.7, 49.4, 43.6, 25.0, 22.7, 14.2.

Ethyl 3-hydroxy-5-(2-isopropoxy-3-methoxyphenyl)pentanoate (81)

To dissolved ketone 80 (2.32 g, 7.52 mmol) in $CH_3OH$ (30 mL) was added $NaBH_4$ (96 mg, 2.5 mmol) at 0° C. The reaction was stirred for 1 h and then returned to room temperature for an additional 1 h. The $CH_3OH$ was removed under reduced pressure, and the residue was washed with water and extracted with EtOAc (3×30 mL). The combined organic phase was evaporated under reduced pressure, and the crude reaction product was purified by flash chromatography using a pre-packed 50 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford alcohol 81 (1.80 g, 5.80 mmol, 77%) as a colorless oil. $^1H$ NMR (600 MHz, $CDCl_3$) δ 6.96 (1H, t, J=8.4 Hz), 6.77 (1H, d, J=6.6 Hz), 6.75 (1H, d, J=7.8 Hz), 4.52 (1H, sept, J=6.6 Hz), 4.13 (2H, q, J=7.2 Hz), 3.91 (1H, m), 3.82 (3H, s), 2.82 (1H, m), 2.74 (1H, m), 2.45 (1H, m), 2.44 (1H, m), 1.78 (1H, m), 1.71 (1H, m), 1.28 (3H, t, J=6.6 Hz), 1.26 (3H, t, J=6.6 Hz), 1.25 (3H, t, J=7.2 Hz). $^{13}C$ NMR (150 MHz, $CDCl_3$) δ 172.8, 152.9, 144.8, 136.0, 123.7, 122.1, 110.3, 74.9, 67.1, 60.7, 55.7, 41.6, 37.5, 41.6, 37.5, 26.3, 22.9, 22.6, 14.3.

Ethyl 3-((tert-butyldiphenylsilyl)oxy)-5-(2-isopropoxy-3-methoxyphenyl)pentanoate (82)

To dissolved alcohol 81 (0.77 g, 2.5 mmol) in DMF (10 mL) were added tert-butyl(chloro)diphenylsilane (TBDPSCl) (0.96 mL, 3.7 mmol) and imidazole (0.280 g, 3.98 mmol) at room temperature, and the solution was stirred for 12 h at room temperature. The DMF was removed under reduced pressure, and the resulting material was washed with brine (50 mL) and extracted with diethyl ether (3×30 mL). The combined organic phase was dried over sodium sulfate and evaporated under reduced pressure. The crude product was purified by flash chromatography using a pre-packed 50 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford protected alcohol 82 (0.960 g, 1.75 mmol, 71%) as a colorless oil. $^1H$ NMR (600 MHz, $CDCl_3$) δ 7.70 (4H, m), 7.39 (6H, m), 6.87 (1H, t, J=7.8 Hz), 6.70 (1H, d, J=8.4 Hz), 6.52 (1H, d, J=7.8 Hz), 4.41 (1H, m), 4.29 (1H, m), 4.00 (2H, m), 3.80 (3H, s), 2.55 (4H, m), 1.76 (2H, m), 1.19 (6H, m), 1.18 (3H, t, J=7.2 Hz), 1.08 (9H, s). $^{13}C$ NMR (150 MHz, $CDCl_3$) δ 171.6, 152.9, 144.9, 136.5, 136.1, 135.3, 135.0, 134.3, 129.8, 129.7, 127.9, 127.6, 123.3, 121.6, 110.1, 74.4, 70.6, 60.4, 55.8, 42.1, 37.8, 26.7, 25.6, 22.7, 19.5, 19.2, 14.2.

3-((Tert-butyldiphenylsilyl)oxy)-5-(2-isopropoxy-3-methoxyphenyl)pentanoic acid (83)

To dissolved protected alcohol 82 (7.80 g, 14.2 mmol) in $CH_3OH$/THF (60 mL/30 mL) was added 2.5 M NaOH (20 mL) at 0° C., and the solution was stirred for 1 h and then room temperature for 13 h. The organic solvents ($CH_3OH$ and THF) were removed under reduced pressure, and water (30 mL) was added to the resulting suspension, followed by extraction with diethyl ether (3×50 mL). The combined organic phase was dried over sodium sulfate and evaporated under reduced pressure. The crude product was purified by flash chromatography using a pre-packed 100 g silica column [solvent A: EtOAc; solvent B: hexanes; gradient: 10% A/90% B (1 CV), 10% A/90% B→60% A/40% B (15 CV), 60% A/40% B (2 CV); flow rate: 100 mL/min; monitored at 254 and 280 nm] to afford carboxylic acid 83 (3.49 g, 6.70 mmol, 46%) as a colorless oil. $^1H$ NMR (600 MHz, $CDCl_3$) δ 7.67 (4H, m), 7.39 (6H, m), 6.86 (1H, t, J=7.8 Hz), 6.70 (1H, d, J=8.4 Hz), 6.50 (1H, d, J=7.2 Hz), 4.41 (1H, m), 4.20 (1H, m), 3.79 (3H, s), 2.56 (4H, m), 1.82 (2H, m), 1.19 (6H, t, J=6 Hz), 1.06 (9H, s). $^{13}C$ NMR (150 MHz, $CDCl_3$) δ 175.5, 152.9, 144.8, 136.0, 133.7, 133.6, 129.9, 127.8, 123.4, 121.6, 110.2, 74.5, 70.5, 55.8, 41.2, 37.5, 27.1, 25.7, 22.7, 19.4.

7-((Tert-butyldiphenylsilyl)oxy)-1-isopropoxy-2-methoxy-6,7,8,9-tetrahydro-5H-benzo[7]annulen-5-one (84)

To dissolved carboxylic acid 83 (3.49 g, 6.70 mmol) in dichloromethane (30 mL) were added oxalyl chloride (2.77 mL, 31.8 mmol) and DMF (0.1 mL) as catalyst at room temperature, and the solution was stirred for 2 h at room temperature. The solvent and unreacted oxalyl chloride were removed under reduced pressure. The yellow acyl chloride was then dissolved in dichloromethane (40 mL) and cooled to −10° C. To this solution, 1 M $SnCl_4$ in a dichloromethane solution (7.4 mL, 7.4 mmol) was added, and the reaction mixture was stirred for 40 min at −10° C. The reaction was quenched by the addition of water, followed by extraction with dichloromethane (3×40 mL). The combined organic phase was dried over sodium sulfate and concentrated. The crude product was purified by flash chromatography using a pre-packed 100 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford ketone 84 (2.19 g, 4.50 mmol, 67%) as a pale-yellow gel. $^1H$ NMR (600 MHz, $CDCl_3$) δ 7.66 (4H, m), 7.54 (1H, d, J=9.6 Hz), 7.38 (6H, m), 6.79 (1H, d, J=9 Hz), 4.36 (1H, m), 4.28 (1H, m), 3.86 (3H, s), 3.14 (1H, m), 3.03 (2H, m), 2.88 (1H, m), 1.94 (2H, m), 1.27 (6H, m), 1.03 (9H, s). $^{13}C$ NMR (150 MHz, $CDCl_3$) δ 199.7, 156.0, 144.1, 138.5, 136.1, 136.0, 135.9, 134.2, 133.9, 133.1, 129.9, 129.8, 127.9, 127.8, 127.7, 125.3, 109.5, 75.2, 68.4, 55.9, 50.4, 36.1, 27.0, 22.7, 22.6, 22.0, 19.3.

7-Hydroxy-1-isopropoxy-2-methoxy-6,7,8,9-tetrahydro-5H-benzo[7]annulen-5-one (85)

Ketone 84 (2.19 g, 4.50 mmol) was dissolved in THF (20 mL), TBAF (9.00 mL, 9.00 mmol) was added at 0° C., and the reaction mixture was stirred for 30 min, followed by additional stirring at room temperature for 6 h. Brine (30 mL) was added, and the resultant solution was extracted with EtOAc (3×30 mL). The combined organic phase was dried over sodium sulfate and evaporated under reduced pressure. The crude product was purified by flash chromatography using a pre-packed 100 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford alcohol 85 (0.41 g, 1.7 mmol, 37%) as a yellow oil. $^1$H NMR (600 MHz, CDCl$_3$) δ 7.57 (1H, d, J=8.4 Hz), 6.8 (1H, d, J=8.4 Hz), 4.41 (1H, m), 4.31 (1H, m), 3.88 (3H, s), 3.11 (2H, m), 3.06 (1H, m), 2.99 (1H, m), 2.15 (1H, m), 1.87 (1H, m), 1.29 (6H, m). $^{13}$C NMR (150 MHz, CDCl$_3$) δ199.6, 156.3, 144.2, 138.4, 132.6, 125.4, 109.7, 75.3, 67.3, 55.9, 50.3, 35.8, 22.7, 22.6, 22.1.

1-Isopropoxy-2-methoxy-7-((trimethylsilyl)oxy)-6,7, 8,9-tetrahydro-5H-benzo[7]annulen-5-one (86)

To a solution of alcohol 85 (0.35 g, 1.33 mmol) in DMF (20 mL) were added imidazole (0.27 g, 6.4 mmol) and TMSCl (4.26 mmol) at room temperature, and the reaction mixture was stirred for 12 h. The solvent was removed under reduced pressure, and brine (20 mL) was added, followed by extraction with EtOAc (3×30 mL). The organic extract was dried over sodium sulfate, filtered, and concentrated under reduced pressure, and the residue was purified by flash chromatography using a pre-packed 50 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford TMS protected ketone 86 (0.19 g, 0.56 mmol, 43%) as a yellow oil. $^1$H NMR (500 MHz, CDCl$_3$) δ 7.54 (1H, d, J=10.2 Hz), 6.79 (1H, d, J=10.8 Hz), 4.39 (1H, m), 4.19 (1H, m), 3.86 (3H, s), 3.22 (1H, m), 2.99 (2H, m), 2.90 (1H, m), 1.91 (2H, m), 1.27 (6H, d, J=9 Hz), 0.11 (9H, s). $^{13}$C NMR (125 MHz, CDCl$_3$) δ 199.7, 156.1, 144.0, 138.6, 132.6, 125.3, 109.5, 75.1, 67.3, 55.8, 51.0, 36.4, 22.6, 22.5, 21.7.

4-Isopropoxy-3-methoxy-9-(3,4,5-trimethoxyphenyl)-5H-benzo[7]annulene (87)

To an oven-dried flask, THF (20 mL) and 3,4,5-trimethoxyphenyl bromide (0.21 g, 0.85 mmol) were added, and the solution was cooled to −78° C. n-BuLi (0.34 mL, 2.5 M, 0.85 mmol) was slowly added to the reaction mixture, which was then stirred at −78° C. for 45 min. Ketone 86 (0.19 g, 0.56 mmol) was then added dropwise to the flask, and the reaction mixture was stirred (−78° C. to 0° C.) over 4 h, and at 0° C. for an additional 1 h. 2 M HCl (20 mL) was added at ° C. followed by stirring for 10 min and extraction with EtOAc (3×30 mL). The combined organic phase was dried over sodium sulfate and evaporated under reduced pressure. The crude product was purified by flash chromatography using a pre-packed 50 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford diene 87 (60 mg, 0.15 mmol, 27%) as a colorless oil. $^1$H NMR (600 MHz, CDCl$_3$) δ 6.81 (1H, d, J=8.4 Hz), 6.71 (1H, d, J=9 Hz), 6.61 (2H, s), 6.60 (1H, d, J=5.4 Hz), 6.17 (1H, m), 5.87 (1H, m), 4.48 (1H, p, J=6.6 Hz), 3.91 (3H, s), 3.86 (6H, s), 3.85 (3H, s), 3.26 (2H, m, b), 1.38 (6H, d, J=6 Hz). $^{13}$C NMR (150 MHz, CDCl$_3$) δ 153.8, 153.0, 145.6, 142.0, 140.4, 137.5, 134.5, 131.7, 128.5, 126.9, 125.9, 124.8, 109.1, 106.7, 75.0, 61.0, 56.3, 55.8, 26.7, 22.8.

3-Methoxy-9-(3,4,5-trimethoxyphenyl)-5H-benzo[7]annulen-4-ol (88)

Isopropyl protected phenol 87 (60 mg, 0.15 mmol) was dissolved in CH$_2$Cl$_2$ (10 mL), to which BCl$_3$ (0.17 mL, 1 M, 0.17 mmol) was added, and the reaction mixture was stirred at 0° C. for 1 h. The solution was washed with water and 2 M HCl and extracted with EtOAc (3×20 mL). The combined organic phase was dried over sodium sulfate and evaporated under reduced pressure. The crude reaction was purified by flash chromatography using a pre-packed 50 g silica column [solvent A: EtOAc; solvent B: hexanes; gradient: 5% A/95% B (1 CV), 5% A/95% B→60% A/40% B (10 CV), 60% A/40% B (2 CV); flow rate: 100 mL/min; monitored at 254 and 280 nm] to afford phenol 88 (40 mg, 0.11 mmol, 75%) as a white solid. $^1$H NMR (600 MHz, CDCl$_3$) δ 6.67 (1H, d, J=8.4 Hz), 6.62 (1H, d, J=9 Hz), 6.60 (2H, s), 6.59 (1H, d, J=5.4 Hz), 6.15 (1H, m), 5.94 (1H, m), 3.89 (6H, s), 3.84 (6H, s), 3.23 (2H, m, b). $^{13}$C NMR (150 MHz, CDCl$_3$) δ 153.0, 147.1, 145.5, 140.6, 140.3, 137.5, 132.2, 128.3, 127.0, 126.2, 126.0, 120.1, 107.6, 106.7, 61.1, 56.3, 56.2, 25.7. HRMS: Obsvd 377.1361 [M+Na$^+$], Calcd for C$_{21}$H$_{22}$O$_5$Na: 377.1359. HPLC: 19.52 min.

Sodium 3-methoxy-9-(3,4,5-trimethoxyphenyl)-5H-benzo[7]annulen-4-yl phosphate (89)

To phenol 88 (95 mg, 0.27 mmol) dissolved in CH$_2$Cl$_2$ (25 mL) was added POCl$_3$ (0.11 mL, 1.1 mmol) and pyridine (0.078 mL, 0.97 mmol), and the reaction mixture was stirred from 0° C. to room temperature for 8 h. The CH$_2$Cl$_2$ was removed under reduced pressure, the residue was dissolved in H$_2$O/THF (10 mL/5 mL) at room temperature, and the solution was stirred for 1 h. A NaOH solution (0.1 M) was added to the reaction mixture to adjust to pH=10 at 0° C., and the solution was stirred at 0° C. for 30 min. Water was removed under reduced pressure. The crude product was purified by flash chromatography using a pre-packed 12 g C-18 column [solvent A: acetonitrile; solvent B: water; gradient: 0% A/100% B (1 CV), 0% A/100% B→10% A/90% B (10 CV), 10% A/90% B (2 CV); flow rate: 12 mL/min; monitored at 254 and 280 nm] to afford phosphate salt 89 (65.8 mg, 0.14 mmol, 51%) as a yellow solid. $^1$H NMR (500 MHz, D$_2$O) δ 6.65 (2H, s), 6.60 (2H, m), 6.53 (1H, d, J=6 Hz), 6.10 (1H, m), 5.98 (1H, m), 3.78 (3H, s), 3.72 (3H, s), 3.70 (6H, s), 3.29 (2H, b). $^{13}$C NMR (125 MHz, D$_2$O) δ 153.0, 152.1, 144.5, 140.8, 138.4, 136.0, 134.5, 131.1, 129.8, 126.2, 126.1, 124.2, 109.1, 106.7, 60.9, 55.9, 55.7, 26.9. $^{31}$P NMR (200 MHz, D$_2$O) δ 0.81. HRMS: Obsvd 479.0841 [M+H$^+$], Calcd for C$_{21}$H$_{22}$O$_8$Na$_2$P$^+$: 479.0842. HPLC: 14.22 min.

Figure 11:
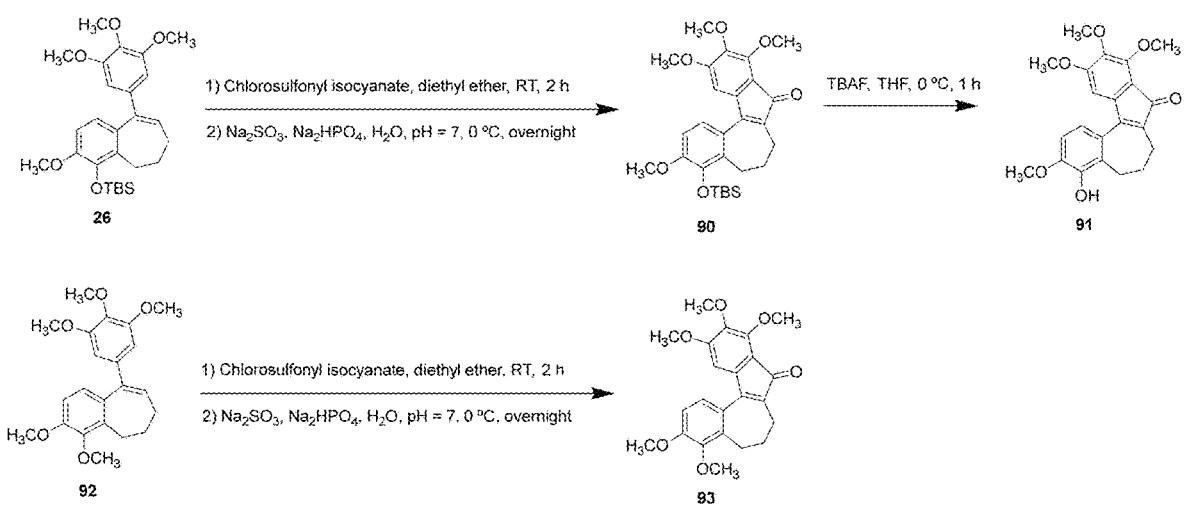
FIG. 11 shows synthetic Scheme 9 for the synthesis of representative compounds described herein.

FIG. 11 shows Scheme 9, synthesis of compounds 91 and 93. For this synthesis, tetrahydrofuran (THF), carbon tetrachloride, dichloromethane, methanol, dimethylformamide (DMF), and acetonitrile were used in their anhydrous forms. Reactions were performed under nitrogen gas, unless otherwise specified. Thin-layer chromatography (TLC) plates (precoated glass plates with silica gel 60 F254, 0.25 mm thickness) were used to monitor reactions. Purification of intermediates and products was carried out with a Biotage Isolera flash purification system using silica gel (200-400 mesh, 60 Å) or RP-18 pre-packed columns or manually in glass columns. Intermediates and products synthesized were characterized on the basis of their $^1$H NMR (500 or 600

MHz), $^{13}$C NMR (125 or 150 MHz) spectroscopic data using a Varian VNMRS 500 MHz or Bruker DPX 600 MHz instrument. Spectra were recorded in $CDCl_3$, $D_2O$, $(CD_3)_2CO$, or $CD_3OD$. All chemicals shifts are expressed in ppm (δ), and peak patterns are reported as broad (br), singlet (s), doublet (d), triplet (t), quartet (q), pentet (p), sextet (sext), septet (sept), double doublet (dd), double double doublet (ddd), and multiplet (m).

Purity of the final compounds was further analyzed at 25° C. using an Agilent 1200 HPLC system with a diode-array detector (λ=190-400 nm), a Zorbax XDB-C18 HPLC column (4.6 mm Å~150 mm, 5 m), and a Zorbax reliance cartridge guard-column; Method: solvent A, acetonitrile, solvent B, $H_2O$; gradient, 10% A/90% B to 100% A/0% B over 0 to 40 min; post-time 10 min; flow rate 1.0 mL/min; injection volume 20 μL; monitored at wavelengths of 210, 230, 254, 280, and 320 nm. Mass spectrometry was carried out under positive or negative ESI (electrospray ionization) using a Thermo Scientific LTQ OrbitrapDiscovery instrument.

Compound 90: 4-((Tert-butyldimethylsilyl)oxy)-3,9,10,11-tetramethoxy-6,7-dihydrodibenzo[a,h]azulen-8(5H)-one. To TBS-protected benzosuberen analogue 26 (0.67 g, 1.7 mmol) dissolved in $Et_2O$ (10 mL) was added chlorosulfonyl isocyanate (0.15 mL, 1.7 mmol) at room temperature, then the reaction mixture was stirred at room temperature for 2 h. $Na_2CO_3$ and $Na_2HPO_4$ buffer (pH=7) solution was added at 0° C., then reaction mixture was stirred for overnight to room temperature. The reaction mixture was then extracted with $Et_2O$ (3×20 mL), The combined organic phase was evaporated under reduced pressure and the crude reaction product was purified by flash chromatography using pre-packed 50 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford product 90 (0.19 g, 0.45 mmol, 26%) as an orange oil. $^1$H NMR ($CDCl_3$, 500 Hz) δ 7.17 (1H, d, J=12 Hz), 6.85 (1H, d, J=12 Hz), 6.65 (1H, s), 4.14 (3H, s), 3.89 (3H, s), 3.86 (3H, s), 3.83 (3H, s), 2.77 (2H, m), 2.30 (2H, m), 2.11 (2H, m), 1.02 (9H, s), 0.21 (6H, s). $^{13}$C NMR ($CDCl_3$, 150 MHz) δ 193.9, 156.7, 152.9, 152.2, 150.8, 143.1, 142.4, 141.1, 135.3, 134.7, 126.7, 120.3, 108.7, 107.7, 102.8, 62.4, 61.5, 56.6, 54.9, 31.2, 26.2, 24.9, 20.6, 19.1, −3.7.

Compound 91: 4-Hydroxy-3,9,10,11-tetramethoxy-6,7-dihydrodibenzo[a,h]azulen-8(5H)-one. TBS-protected cyclized ketone 90 (0.39 g, 0.79 mmol) was dissolved in THF (6 mL), TBAF (0.87 mL, 0.87 mmol) was added, and the reaction mixture was stirred at 0° C. for 1 h. The solution was washed with water and extracted with EtOAc (3×20 mL). The combined organic phase was dried over sodium sulfate and evaporated under reduced pressure. The crude reaction product was purified by flash chromatography using a pre-packed 25 g silica column [solvent A: EtOAc; solvent B: hexanes; gradient: 7% A/93% B (1 CV), 7% A/93% B→60% A/40% B (10 CV), 60% A/40% B (2 CV); flow rate: 100 mL/min; monitored at 254 and 280 nm] to afford phenol (0.27 g, 0.71 mmol, 90%) as an orange solid. $^1$H NMR (600 MHz, $CDCl_3$) δ 7.11 (1H, d, J=6 Hz), 6.86 (1H, d, J=6 Hz), 6.65 (1H, s), 5.82 (1H), 4.14 (3H, s), 3.97 (3H, s), 3.89 (3H, s), 3.84 (3H, s), 2.77 (2H, m), 2.31 (2H, m), 2.14 (2H, m). $^{13}$C NMR (150 MHz, $CDCl_3$) δ 193.8, 156.8, 152.8, 151.9, 147.0, 143.8, 142.3, 141.1, 135.6, 125.0, 127.2, 118.8, 107.1, 107.7, 102.7, 62.4, 61.5, 56.6, 56.2, 31.0, 24.2, 20.4. HRMS: Obsvd 405.1315 [M+Na$^+$], Calcd for $C_{22}H_{22}O_6Na$: 405.1309. HPLC: 18.97 min.

Compound 93: 3,4,9,10,11-Pentamethoxy-6,7-dihydrodibenzo[a,h]azulen-8(5H)-one. To dimethoxy benzosuberene analogue 92 (50 mg, 0.13 mmol) dissolved in $Et_2O$ (10 mL) was added chlorosulfonyl isocyanate (0.058 mL, 0.13 mmol) at room temperature, then the reaction mixture was stirred at room temperature for 2 h. $Na_2CO_3$ and $Na_2HPO_4$ buffer (pH=7) solution was added at 0° C., then reaction mixture was stirred overnight to room temperature. The reaction mixture was then extracted with $Et_2O$ (3×20 mL), The combined organic phase was evaporated under reduced pressure and the crude reaction product was purified by flash chromatography using pre-packed 25 g silica column [solvent A: EtOAc; solvent B: hexanes; gradient: 10% A/90% B (1 CV), 10% A/90% B→40% A/60% B (10 CV), 40% A/60% B (2 CV); flow rate: 100 mL/min; monitored at 254 and 280 nm] to afford product 93 (16 mg, 0.04 mmol, 30%) as an orange solid. $^1$H NMR ($CDCl_3$, 600 MHz) δ 7.22 (1H, d, J=6 Hz), 6.94 (1H, d, J=6 Hz), 6.76 (1H, s), 4.21 (3H, s), 3.94 (3H, s), 3.89 (3H, s), 3.87 (3H, s), 3.85 (3H, s), 2.32 (6H, m, b). $^{13}$C NMR ($CDCl_3$, 150 MHz) δ157.7, 153.5, 150.6, 147.5, 142.0, 138.7, 136.5, 136.2, 129.1, 124.3, 123.9, 120.8, 109.9, 120.3, 62.0, 61.3, 61.28, 61.24, 56.5, 55.8, 33.0, 23.8, 19.6. HRMS: Obsvd 419.1467 [M+Na$^+$], Calcd for $C_{23}H_{24}O_6Na^+$: 419.1465. HPLC: 21.10 min.

Example 2. Biological Evaluation

Cell Lines and Sulforhodamine B (SRB) Assay.

The sulforhodamine B (SRB) assay was used to assess growth inhibition of human cancer cells, as previously described. DU-145, SK-OV-3, and NCI-H460 cancer cell lines (obtained from ATCC) were maintained in T75 flasks (Corning) using high glucose DMEM supplemented with 10% fetal bovine serum (Gibco)/1% gentamicin sulfate for a maximum of 15 passages. For these experiments, cells were trypsinized, counted, and plated at 7000-8000 cells/well into 96-well plates (Corning) and incubated for 24 h at 37° C. in a humidified incubator in a 5% $CO_2$ atmosphere. Compounds to be tested were dissolved in DMSO to generate a 10 mg/mL stock solution, and serial dilutions added in media to the plates. Doxorubicin (Sigma-Aldrich) and paclitaxel (Tokyo Chemical) were used as positive controls. After a 48 h treatment, the cells were fixed with trichloroacetic acid (10% final concentration), washed, dried, stained with SRB dye, washed to remove excess dye, and dried. SRB dye was solubilized, and absorbances were measured at wavelength 540 nm and normalized to values at wavelength 630 nm using an automated Biotek plate reader. A growth inhibition of 50% ($GI_{50}$ or the drug concentration causing 50% reduction in the net protein increase) was calculated from the absorbance data.

Colchicine Binding Assay.

Inhibition of [$^3$H]colchicine binding to tubulin was measured in 0.1 mL reaction mixtures, each containing 1.0 μM tubulin, 5.0 μM [$^3$H]colchicine (Perkin-Elmer), 5% (v/v) dimethyl sulfoxide, compounds at 1.0 or 5.0 μM, as indicated, and components that stabilize the colchicine binding activity of tubulin (1.0 M monosodium glutamate [adjusted to pH 6.6 with HCl in a 2.0 M stock solution], 0.5 mg/mL bovine serum albumin, 0.1 M glucose-1-phosphate, 1.0 mM $MgCl_2$, and 1.0 mM GTP). Incubation was for 10 min at 37° C., when in control reaction mixtures colchicine binding is 40-60% complete. Reactions were stopped with 2.0 mL of ice-cold water, with the reaction mixtures being placed on ice. Each diluted sample was poured onto a stack of two DEAE-cellulose filters (GE Biomedical), followed by 3 successive 2 mL aliquots of ice-cold water. A reduced vacuum was used to remove excess water from the filters, which were washed three times with 2 mL water and placed into vials containing 5 mL of Biosafe II scintillation cocktail. Samples were counted 18 h later in a Beckman scintillation counter. Samples with inhibitors were compared to samples with no inhibitor, and percent inhibition was determined, correcting all values for the amount of radiolabel bound to the filters in the absence of tubulin.

Inhibition of Tubulin Polymerization.

Tubulin polymerization was evaluated in 0.25 mL reaction mixtures (final volume) containing 1 mg/mL (10 µM) purified bovine brain tubulin, 0.8 M monosodium glutamate (pH 6.6), 4% (v/v) dimethyl sulfoxide, 0.4 mM GTP, and different compound concentrations. All components except GTP were preincubated for 15 min at 30° C. in 0.24 mL. The assay mixtures were cooled to 0° C., and 10 µL of 0.01 M GTP was added to each sample. Reaction mixtures were transferred to cuvettes held at 0° C. in Beckman DU-7400 and DU-7500 spectrophotometers equipped with electronic temperature controllers. The temperature was increased to 30° C., over about 30 s, and polymerization was followed turbidimetrically at 350 nm for 20 min. The $IC_{50}$ was defined as the compound concentration inhibiting extent of polymerization by 50% after 20 min.

In Vivo Vascular Disruption.

The human prostate cancer cell line (PC3) was modified by knock down of a tumor suppressor protein PC3-DAB2IP and further modified by transfection with a firefly luciferase reporter, as described in detail previously. Male Copenhagen rats (originally from Charles River and bred at UT Southwestern) were inoculated subcutaneously with $5\times10^5$ PC3-DAB2IP-luc cells mixed with 30% Matrigel® in the right thigh. These rats were approximately 6 weeks old and weighed between 100-120 g on date of implantation. Tumors were allowed to grow to a diameter of at least 1 cm before treatment commenced. Three rats were treated with VDA prodrug 89 (25 mg/mL in saline) administered IP. Rat 1 received 10 mg/kg followed by 40 mg/kg 24 h later and CA4P (30 mg/kg at 20 mg/mL in saline) was administered IP as a control 4 days later. Rat 2 received a single dose of 40 mg/kg of VDA prodrug 89, and rat 3 received 80 mg/kg of 89. Bioluminescence imaging (BLI) was performed before treatment (baseline), and at 4 and 24 h after treatment using an IVIS Spectrum® (Perkin-Elmer). Briefly, anesthetized rats (breathing oxygen with 3% isoflurane, Henry Schein Inc.) were injected subcutaneously in the foreback neck region with 120 mg/kg D-luciferin sodium salt (Gold Biotechnology, St. Louis, Mo.) and imaged over a time course of about 30 min. Fresh luciferin was administered at each time point. The resulting light intensity time curves were analyzed using Living Image® Software and light emission measured for a region of interest encompassing the tumor. All animal procedures were carried out in accordance with the Guide for the Care and Use of Laboratory Animals as adopted and promulgated by the U.S. National Institutes of Health as well as the Institutional Animal Care and Use Committee approved protocols (APN 2017-102168) at the University of Texas Southwestern Medical Center.

Each of the compounds in FIG. 2 was evaluated for its cytotoxicity against human cancer cell lines [SK-OV-3 (ovarian), NCI-H460 (lung), DU-145 (prostate)] and for the ability to inhibit tubulin polymerization. The results are shown below in Table 1 and in Table 2.

TABLE 1

| Compound | Inhibition of tubulin polymerization $IC_{50}$ (µM) ± SD | % Inhibition of colchicine binding ± SD | $GI_{50}$ (µM) SRB assay[a] | | |
|---|---|---|---|---|---|
| | | | SK-OV-3 | NCI-H460 | DU-145 |
| CA4 | 1.0 | 84 ± 3 (1 µM), 98 ± 0.007 (5 µM) | 0.00455 | 0.00223 | 0.00327 |
| CA4P | >40 | ND | 0.00119 | 0.00194 | 0.00323 |
| KGP18 | 0.85 ± 0.02 | 73 ± 5 (1 µM), 95 ± 0.5 (5 µM) | 0.0000543 | 0.0000418 | 0.0000249 |
| KGP03 | 0.5 | 90 ± 2 (1 µM), 98 ± 0.3 (5 µM) | 0.0029 | 0.0032 | 0.000040 |
| Doxorubicin | ND | ND | 0.0789 | 0.123 | 0.134 |
| Paclitaxel | NR | NR | 0.00134 | 0.00176 | 0.00147 |
| 9 | 1.6 ± 0.2 | 65 ± 0.6 (5 µM) | 0.330 | 0.422 | 0.644 |
| 20 | >20 | ND | 11.5 | 16.1 | 12.2 |
| 23 | >20 | ND | 0.394 | 0.173 | 0.0330 |
| 24 | 1.2 ± 0.1 | 72 ± 2 (5 µM) | 0.0314 | 0.0476 | 0.141 |
| 28 | >20 | ND | 6.52 | 1.90 | 5.66 |
| 31 | >20 | ND | 3.22 | 0.855 | 3.76 |
| 33 | 0.39 ± 0.06 | 88 ± 1 (5 µM) | 0.0221 | 0.0353 | 0.0362 |
| 34 | 4.9 ± 0.1 | 35 ± 5 (1 µM) | 0.312 | 0.449 | 0.423 |
| 35 | >20 | 0 (5 µM) | 3.03 | 3.86 | 4.04 |
| 38 | 1.1 ± 0.1 | 62 ± 0.7 (5 µM) | 0.0648 | 0.434 | 0.860 |
| 39 | 0.37 ± 0.08 | 73 ± 0.6 (5 µM) | 0.0384 | 0.0605 | ND |
| 40 | 3.2 ± 0.08 | 61 ± 3 (5 µM) | 0.0572 | 0.0847 | 0.0402 |
| 47 | 1.0 ± 0.07 | 47 ± 1 (5 µM) | 0.299 | 0.353 | 0.631 |
| 48 | 0.63 ± 0.03 | 76 ± 2 (5 µM) | 0.0403 | 0.0628 | ND |
| 57 | 3.8 ± 0.5 | 28 ± 4 (5 µM) | 0.263 | 0.432 | 0.439 |
| 69 | >20 | 0.4 ± 0.6 (5 µM) | ND | 0.334 | 1.20[b] |
| 76 | >20 | 0 (5 µM) | 27.2 | 70.5 | 26.0 |
| 77 | >20 | 0 (5 µM) | 5.77 | 2.00 | 4.45 |
| 88 | 0.48 ± 0.08 | 68 ± 1 (0.5 µM), 95 ± 0.8 (5 µM) | 0.00690 | 0.0581 | 0.0976 |
| 89 | 16 ± 0.7 | 45 ± 2 (5 µM) | 0.0153 | 0.0291 | 0.0239 |

[a]Average of n ≥ 3 independent determinations (unless otherwise noted)
[b]Average of n = 2 independent determinations (of duplicates)
ND = Not Determined
NR = Not Relevant (paclitaxel enhances microtubule assembly)

TABLE 2

| Compound | Inhibition of tubulin polymerization $IC_{50}$ (µM) ± SD | % Inhibition of colchicine binding ± SD | $GI_{50}$ (µM) SRB assay[a] | | |
|---|---|---|---|---|---|
| | | | SK-OV-3 | NCI-H460 | DU-145 |
| 91 | 4.2 ± 0.2 | 45 ± 4 (5 µM) | 0.0399 | 0.105 | 0.0321 |
| 93 | >20 | ND | 3.35 | 0.650 | 3.26 |

[a]Average of n ≥ 3 independent determinations (unless otherwise noted)
ND = Not Determined Ten of the evaluated molecules were identified as strong inhibitors of tubulin assembly ($IC_{50}$<5 µM, cell-free assay), while seven of the ten were highly active ($IC_{50}$≤1.2 µM). CA4 ($IC_{50}$≈1 µM) and KGP18 (compound 27, $IC_{50}$≈0.85 µM) were utilized as comparative compounds. Three of the benzosuberene and dihydronaphthalene analogues (compounds 33, 39), along with an additional compound (88), were more potent against tubulin in comparison to our dihydronaphthalene lead compound KGP03 ($IC_{50}$≤0.5 µM). Excellent $IC_{50}$ values for inhibition of tubulin polymerization were retained upon alteration of the 4-position phenolic moiety into nitrile, ethyl ester, $CH_2OH$ groups (38, 39, 47, 48), along with modifications to the double bond on seven-member ring that included replacement with ketone and tertiary alcohol groups, substitution with a bromine group, and increased unsaturation (24, 33, 88). Extension of the alkyl chain (at position 4) through an ether linkage that terminated with a polar alcohol group (compound 31) and separately a methoxy moiety (compound 28) resulted in loss of inhibitory activity. Incorporation of a hydrogen bond donor at the allylic position on the seven-member ring (compounds 57 and 69) and substituted saturation of the double bond (compounds 23 and 35) both reduced inhibition of tubulin polymerization. The lack of tubulin activity observed with compound 76 was unanticipated, since semi-rigidity of the seven-membered ring was maintained through a double bond one carbon removed from the stereogenic center, and its parent benzosuberene analogue (dimethoxy group on the fused aryl ring) demonstrated a moderate degree of inhibition of tubulin polymerization ($IC_{50}$=3.1 µM) reported in our previous study. The lack of activity of compound 77 in regard to inhibition of tubulin polymerization suggested that the trimethoxy pendant aryl ring situated at the benzylic position on the fused-ring system was closely correlated to biological efficacy (at least in regard to inhibition of tubulin polymerization). This β-position substitution with a trimethoxy aryl ring has not been previously investigated.

Among the benzosuberene and dihydronaphthalene analogues investigated, the most cytotoxic agents were compounds 24, 33, 38, 39, 48, 88 ($GI_{50}$=0.0314, 0.0221, 0.0648, 0.0384, 0.0403 µM, and 0.00690 µM, respectively, against the SK-OV-3 ovarian cancer cell line, for example). Judiciously selected structural modifications to the 4, 8, and 9-positions in the parent benzosuberene scaffold accounted for the majority of the highly potent analogues evaluated in this study. While the strong cytotoxicity of this sub-set of molecules is encouraging, it is noteworthy that all molecules proved less cytotoxic than the lead benzosuberene KGP18 and less cytotoxic (with the partial exception of compound 88) than the natural product CA4, despite demonstrating similar inhibition of tubulin polymerization (cell free assay). These observations provided an important extension to the known SAR considerations regarding structural modifications to KGP18. As anticipated (and similarly observed for combretastatin A-4 phosphate), the benzosuberene phosphate prodrug salt 89 was inactive as an inhibitor of tubulin polymerization in this cell-free assay, presumably due to the lack of phosphatase enzymes necessary to cleave the prodrug to its parent phenolic (biologically active) agent. Prodrug 89 was an active cytotoxic agent since non-specific phosphatase activity is present in these cancer cell-based cytotoxicity assays.

Example 3. Assessment of Vascular Damage

Ultimately, VDAs will be used in vivo, and thus it is crucial to understand both efficacy of vascular disruption and potential off target toxicity in vivo. As a preliminary investigation, the extent of vascular damage was assessed in a human prostate tumor line in rats treated with the water-soluble prodrug salt 89 compared to CA4P as control. Many imaging methods have been developed to assess vascular disruption non-invasively in vivo. Dynamic bioluminescence imaging (BLI) was favored for initial validation of VDA activity since it provides a fast, non-invasive and easy method and allows comparison of repeat or sequential investigations. BLI does require the use of cells transfected to express luciferase (luc), but these are commonly available and we have used this approach extensively as have others. The human prostate cancer PC3 line was used, in which the tumor suppressor protein DAB2IP had been knocked down and luciferase introduced. BLI requires administration of luciferin substrate, which readily crosses membranes and is carried throughout the vasculature. The measurement of light emission dynamics is related to vascular delivery of the luciferin substrate, and thus it provides a measure of vascular patency. Disruption of tumor vasculature blocks delivery of the substrate and consequently results in a quantifiable decrease in bioluminescent signal. The extent of vascular shutdown was evaluated using IP doses of 10 and 40 or 80 mg/kg of 89 and compared to a dose of 30 mg/kg of CA4P, which had been shown previously to cause extensive vascular shutdown in rats at this dose. It should also be noted that the lead benzosuberene KGP18 and the dihydronaphthalene KGP03 (both as their corresponding water-soluble phosphate prodrug salts (KGP265 and KGP04, respectively), along with other structurally modified benzosuberene analogues, demonstrated vascular shutdown (as evidenced by similar BLI imaging studies or color Doppler ultrasound).

Figure 12:
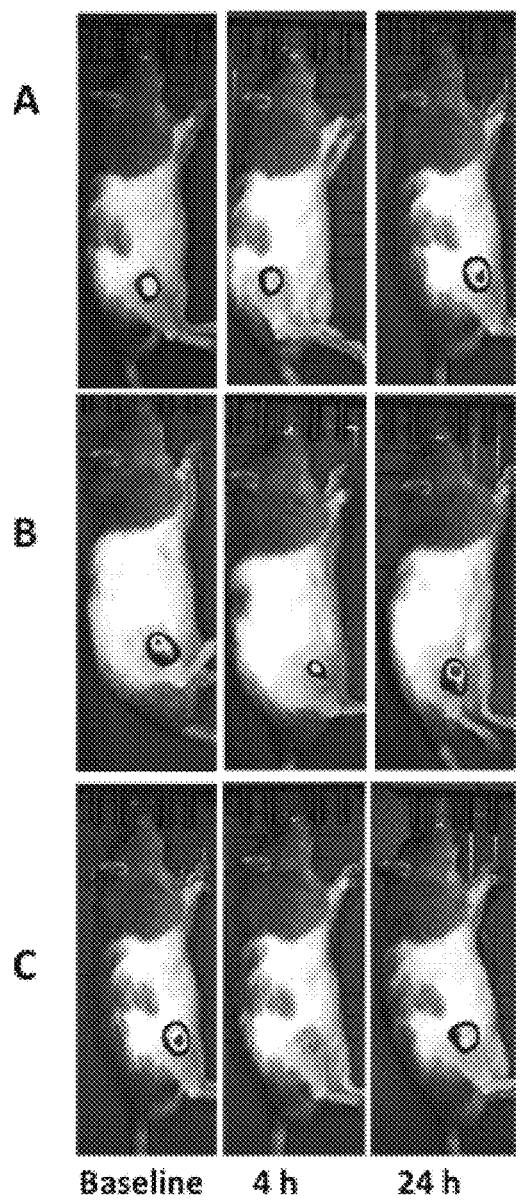
FIG. 12 shows results of a BLI assessment of vascular response to exemplary vascular disrupting agents (VDAs) in rats.
Figure 12:
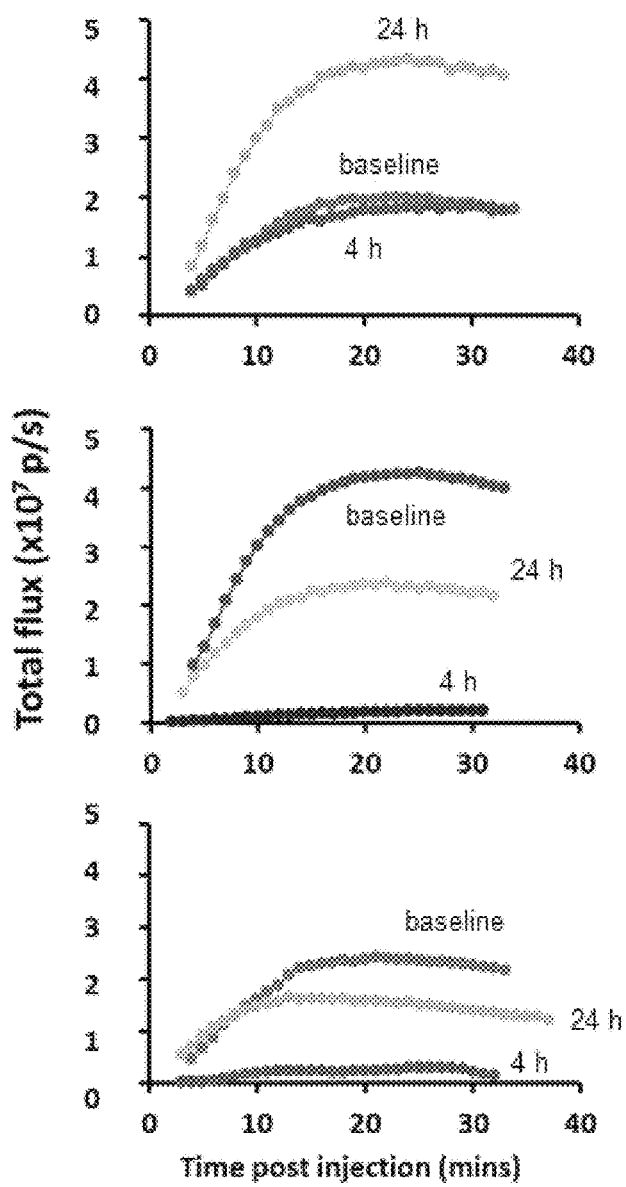

FIG. 12 shows a BLI assessment of vascular response to VDA. On the left, heat maps are overlaid on photographs of male Copenhagen rat with subcutaneous PC3-DAB2IP-luc human prostate tumor xenograft showing light emission about 20 min after administration of D-luciferin (120 mg/kg) at various times with respect to VDA administration IP. On the right, corresponding dynamic light emission curves acquired over about 30 min following luciferin administration, at baseline, about 4 h after VDA, and at 24 h after VDA. A shows results for 10 mg/kg compound 89 indicating no vascular perturbation, but increased signal at 24 h consistent with rapid tumor growth. B shows 6 h later 40 mg/kg compound 89 was administered to the same rat generating about 95% reduced signal at 4 h, consistent with substantial vascular shutdown and showing substantial recovery by 24 h. C shows four days later 30 mg/kg CA4P was administered to this rat eliciting BLI response similar to the BLI response shown in B.

Prodrug 89 administered at 10 mg/kg resulted in minimal change in light emission. A subsequent dose of 40 mg/kg 89 resulted in substantially diminished light emission (signal reduction 95%), but with substantial recovery by 24 h. When CA4P (30 mg/kg) was administered 4 days later it caused a very similar effect in terms of extent and longevity of diminished BLI signal as a surrogate for vascular shutdown. Similar activity was observed when a treatment naïve rat was given 40 mg/kg 89 with substantial recovery at 24 h.

Figure 13:
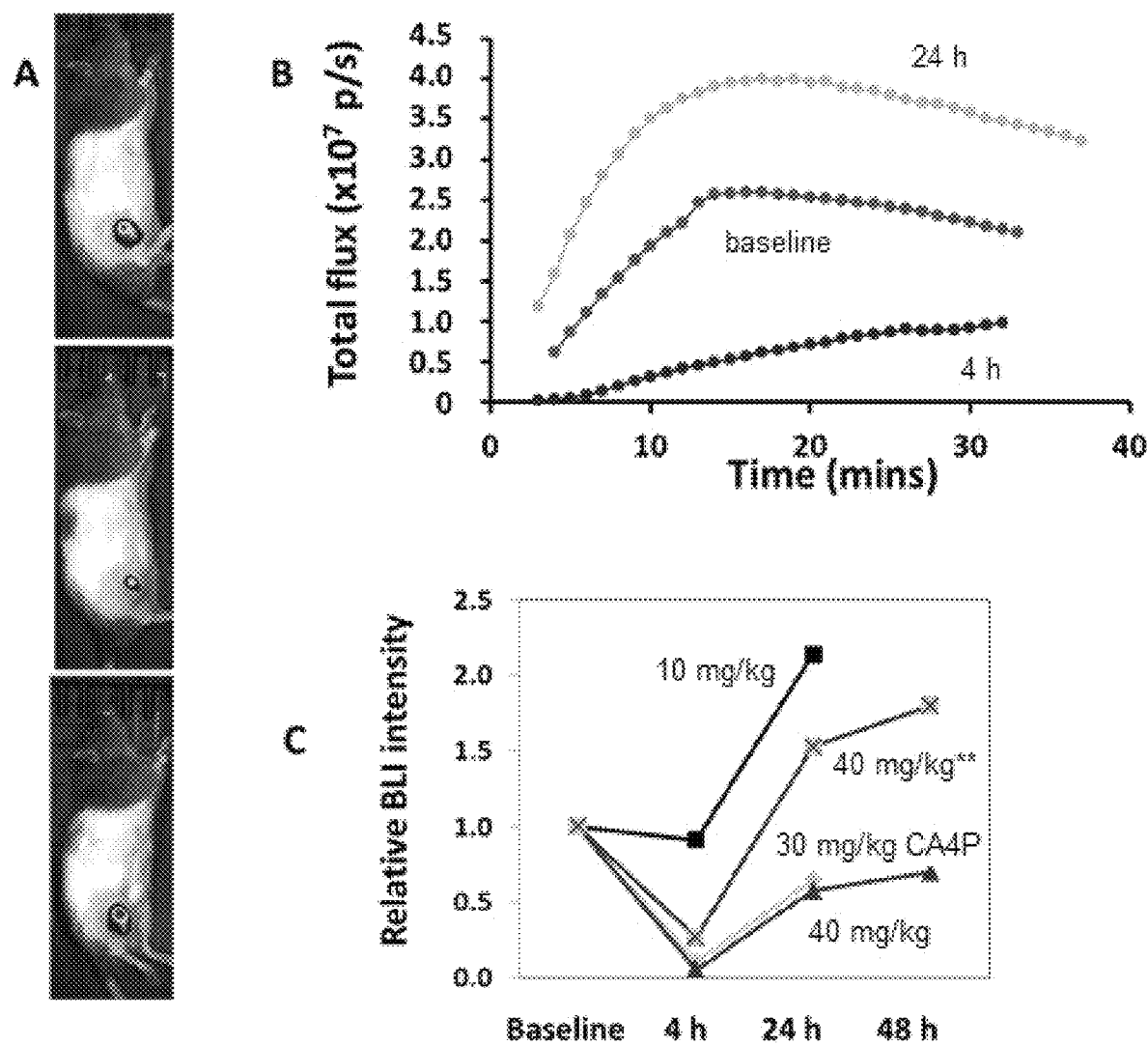
FIG. 13 shows relative light emission following administration of VDAs in rats.

FIG. 13 shows relative light emission following administration of VDAs. A shows relative signal intensity is shown about 20 min after administration of D-luciferin subcutaneously in the foreback neck region of a rat with a subcutaneous PC3-DAB2IP-luc prostate tumor xenograft in the thigh. Top was baseline (no prior drug), center was 4 h after 40 mg/kg 89, and bottom was 24 h after 89. B shows corresponding light emission dynamic curve at baseline, 4 h after 89 and 24 h after 69. C shows normalized BLI signal at various times for the rat in FIG. 12 receiving 69 sequentially at 10 mg/kg, 40 mg/kg and 30 mg/kg CA4P, together with the treatment naive rat in A, B receiving 40 mg/kg 89 (**). At 48 h the rats appeared healthy and the signal increased marginally. A dose of 80 mg/kg was also well tolerated, but this higher dose did not show additional vascular disruption.

Results in these examples demonstrate the impact of structural modifications to lead benzosuberene and dihydronaphthalene analogues on inhibition of tubulin polymerization and cytotoxicity against human cancer cell lines. Amongst this group of new molecules [along with compound (88), accessed through separate synthesis], emerged several promising analogues (compounds 24, 33, 38, 39, 48, 88) that elicited inhibition ($IC_{50}$) of tubulin assembly (cell free assay) greater than or comparable to that of the lead natural product CA4 and our lead benzosuberene analogues KGP18 and KGP156. These compounds demonstrated potent cytotoxicity ($GI_{50}$) against SK-OV-3 (ovarian), NCI-H460 (lung), and DU-145 (prostate) cells typically in the low to mid nM range. Preliminary investigation of water-soluble benzosuberene phosphate prodrug salt 89 at 40 mg/kg in vivo revealed vascular disruption in a PC3-DAB2IP-luc human prostate tumor xenograft based on BLI (shown in FIGS. 12 and 13) which was similar to that obtained with CA4P.

REFERENCES

The following patents and publications are hereby incorporated by reference.

Haichan Niu, et al., Structure Guided Design, Synthesis, and Biological Evaluation of Novel Benzosuberene Analogues as Inhibitors of Tubulin Polymerization, *J. Med. Chem.* 2019, 2019, 62, 5594-5615.

(1) Salmon, B. A.; Siemann, D. W. Characterizing the Tumor Response to Treatment with Combretastatin A4 Phosphate. *Int. J. Radiat. Oncol. Biol. Phys.* 2007, 68 (1), 211-217. https://doi.org/10.1016/j.ijrobp.2006.12.051.

(2) Hanahan, D.; Weinberg, R. A. Hallmarks of Cancer: The Next Generation. Cell 2011, 144 (5), 646-674. https://doi.org/10.1016/j.cell.2011.02.013.

(3) Siemann, D. W. The Unique Characteristics of Tumor Vasculature and Preclinical Evidence for Its Selective Disruption by Tumor-Vascular Disrupting Agents. *Cancer Treat. Rev.* 2011, 37 (1), 63-74. https://doi.org/10.1016/j.ctrv.2010.05.001.

(4) Tozer, G. M.; Kanthou, C.; Baguley, B. C. Disrupting Tumour Blood Vessels. *Nat. Rev. Cancer* 2005, 5 (6), 423-435. https://doi.org/10.1038/nrc1628.

(5) Kanthou, C.; Tozer, G. M. Tumour Targeting by Microtubule-Depolymerizing Vascular Disrupting Agents. *Expert Opin. Ther. Targets* 2007, 11 (11), 1443-1457. https://doi.org/10.1517/14728222.11.11.1443.

(6) Denekamp, J. Endothelial Cell Proliferation as a Novel Approach to Targeting Tumour Therapy. *Br. J. Cancer* 1982, 45 (1), 136-139.

(7) Denekamp, J. Review Article: Angiogenesis, Neovascular Proliferation and Vascular Pathophysiology as Targets for Cancer Therapy. *Br. J. Radiol.* 1993, 66 (783), 181-196. https://doi.org/10.1259/0007-1285-66-783-181.

(8) Sriram, M.; Hall, J. J.; Grohmann, N. C.; Strecker, T. E.; Wootton, T.; Franken, A.; Trawick, M. L.; Pinney, K. G. Design, Synthesis and Biological Evaluation of Dihydronaphthalene and Benzosuberene Analogs of the Combretastatins as Inhibitors of Tubulin Polymerization in Cancer Chemotherapy. *Bioorg. Med. Chem.* 2008, 16 (17), 8161-8171. https://doi.org/10.1016/j.bmc.2008.07.050.

(9) Horsman, M. R.; Bohn, A. B.; Busk, M. Vascular Targeting Therapy: Potential Benefit Depends on Tumor and Host Related Effects. *Exp. Oncol.* 2010, 32 (3), 143-148.

(10) Siemann, D. W.; Bibby, M. C.; Dark, G. G.; Dicker, A. P.; Eskens, F. A. L. M.; Horsman, M. R.; Marmé, D.; LoRusso, P. M. Differentiation and Definition of Vascular-Targeted Therapies. *Clin. Cancer Res.* 2005, 11 (2 I), 416-420.

(11) Mason, R. P.; Zhao, D.; Liu, L.; Trawick, M. L.; Pinney, K. G. A Perspective on Vascular Disrupting Agents That Interact with Tubulin: Preclinical Tumor Imaging and Biological Assessment. *Integr. Biol.* 2011, 3 (4), 375-387. https://doi.org/10.1039/COIB00135J.

(12) Dougherty, G. J.; Chaplin, D. J. Development of Vascular Disrupting Agents. In *Vascular Disruptive Agents for the Treatment of Cancer*; Springer, New York, N.Y., 2010; pp 1-27. https://doi.org/10.1007/978-1-4419-6609-4_1.

(13) Siemann, D. W. Tumor Vasculature: A Target for Anticancer Therapies. In *Vascular-Targeted Therapies in Oncology*; Siemann, D. W., Ed.; Chichester, 2006; pp 1-8.

(14) Monk, K. A.; Siles, R.; Hadimani, M. B.; Mugabe, B. E.; Ackley, J. F.; Studerus, S. W.; Edvardsen, K.; Trawick, M. L.; Garner, C. M.; Rhodes, M. R.; Pettit, G. R.; Pinney, K. G. Design, Synthesis, and Biological Evaluation of Combretastatin Nitrogen-Containing Derivatives as Inhibitors of Tubulin Assembly and Vascular Disrupting Agents. *Bioorg. Med. Chem.* 2006, 14 (9), 3231-3244. https://doi.org/10.1016/j.bmc.2005.12.033.

(15) Pettit, G. R.; Singh, S. B.; Boyd, M. R.; Hamel, E.; Pettit, R. K.; Schmidt, J. M.; Hogan, F. Antineoplastic Agents. 291. Isolation and Synthesis of Combretastatins A-4, A-5, and A-6. *J. Med. Chem.* 1995, 38 (10), 1666-1672. https://doi.org/10.1021/jm00010a011.

(16) McGown, A. T.; Fox, B. W. Differential Cytotoxicity of Combretastatins A1 and A4 in Two Daunorubicin-Resistant P388 Cell Lines. *Cancer Chemother. Pharmacol.* 1990, 26 (1), 79-81.

(17) Pettit, G. R.; Moser, B. R.; Boyd, M. R.; Schmidt, J. M.; Pettit, R. K.; Chapuis, J.-C. Antineoplastic Agents 460. Synthesis of Combretastatin A-2 Prodrugs. *Anticancer. Drug Des.* 2001, 16 (4-5), 185-193.

(18) Pettit, G. R.; Singh, S. B.; Hamel, E.; Lin, C. M.; Alberts, D. S.; Garcia-Kendal, D. Isolation and Structure of the Strong Cell Growth and Tubulin Inhibitor Combretastatin A-4. *Experientia* 1989, 45 (2), 209-211. https://doi.org/10.1007/BF01954881.

(19) Dark, G. G.; Hill, S. A.; Prise, V. E.; Tozer, G. M.; Pettit, G. R.; Chaplin, D. J. Combretastatin A-4, an Agent That Displays Potent and Selective Toxicity Toward Tumor Vasculature. *Cancer Res.* 1997, 57 (10), 1829-1834.

(20) Pettit, G. R.; Toki, B.; Herald, D. L.; Verdier-Pinard, P.; Boyd, M. R.; Hamel, E.; Pettit, R. K. Antineoplastic Agents. 379. Synthesis of Phenstatin Phosphate. *J. Med. Chem.* 1998, 41 (10), 1688-1695. https://doi.org/10.1021/jm970644q.

(21) Boyland, E.; Boyland, M. E. Studies in Tissue Metabolism: The Action of Colchicine and B. Typhosus Extract. *Biochem. J.* 1937, 31 (3), 454-460.

(22) Woods, J. A.; Hadfield, J. A.; Pettit, G. R.; Fox, B. W.; McGown, A. T. The Interaction with Tubulin of a Series of Stilbenes Based on Combretastatin A-4. *Br. J. Cancer* 1995, 71 (4), 705-711.

(23) Pettit, G. R.; Singh, S. B.; Niven, M. L.; Hamel, E.; Schmidt, J. M. Isolation, Structure, and Synthesis of Combretastatins A-1 and B-1, Potent New Inhibitors of Microtubule Assembly, Derived from Combretum Caffrum. *J. Nat. Prod.* 1987, 50 (1), 119-131. https://doi.org/10.1021/np50049a016.

(24) Pettit, G. R.; Grealish, M. P.; Herald, D. L.; Boyd, M. R.; Hamel, E.; Pettit, R. K. Antineoplastic Agents. 443. Synthesis of the Cancer Cell Growth Inhibitor Hydroxyphenstatin and Its Sodium Diphosphate Prodrug. *J. Med. Chem.* 2000, 43 (14), 2731-2737. https://doi.org/10.1021/jm000045a.

(25) Herdman, C. A.; Devkota, L.; Lin, C.-M.; Niu, H.; Strecker, T. E.; Lopez, R.; Liu, L.; George, C. S.; Tanpure, R. P.; Hamel, E.; Chaplin, D. J.; Mason, R. P.; Trawick, M. L.; Pinney, K. G. Structural Interrogation of Benzosuberene-Based Inhibitors of Tubulin Polymerization. *Bioorg. Med. Chem.* 2015, 23 (24), 7497-7520. https://doi.org/10.1016/j.bmc.2015.10.012.

(26) Tanpure, R. P.; Harkrider, A. R.; Strecker, T. E.; Hamel, E.; Trawick, M. L.; Pinney, K. G. Application of the McMurry Coupling Reaction in the Synthesis of Tri- and Tetra-Arylethylene Analogues as Potential Cancer Chemotherapeutic Agents. *Bioorg. Med. Chem.* 2009, 17 (19), 6993-7001. https://doi.org/10.1016/j.bmc.2009.08.011.

(27) Pinney, K. G.; Pettit, G. R.; Trawick, M. L.; Jelinek, C.; Chaplin, D. J. The Discovery and Development of the Combretastatins. *Anticancer Agents Nat. Prod.* 2012, 27-63.

(28) Pinney, K. G. Molecular Recognition of the Colchicine Binding Site as a Design Paradigm for the Discovery and Development of Vascular Disrupting Agents. In *Vascular-Targeted Therapies in Oncology*; Siemann, D. W., Ed.; Chichester, 2006; pp 95-121.

(29) Siles, R.; Ackley, J. F.; Hadimani, M. B.; Hall, J. J.; Mugabe, B. E.; Guddneppanavar, R.; Monk, K. A.; Chapuis, J.-C.; Pettit, G. R.; Chaplin, D. J.; Edvardsen, K.; Trawick, M. L.; Garner, G. M.; Pinney, K. G. Combretastatin Dinitrogen-Substituted Stilbene Analogues as Tubulin-Binding and Vascular-Disrupting Agents. *J. Nat. Prod.* 2008, 71 (3), 313-320. https://doi.org/10.1021/np070377j.

(30) Shirali, A.; Sriram, M.; Hall, J. J.; Nguyen, B. L.; Guddneppanavar, R.; Hadimani, M. B.; Ackley, J. F.; Siles, R.; Jelinek, C. J.; Arthasery, P.; Brown, R. C.; Murrell, V. L.; McMordie, A.; Sharma, S.; Chaplin, D. J.; Pinney, K. G. Development of Synthetic Methodology Suitable for the Radiosynthesis of Combretastatin A-1 (CA1) and Its Corresponding Prodrug CA1P. *J. Nat. Prod.* 2009, 72 (3), 414-421. https://doi.org/10.1021/np800661r.

(31) Chaplin, D. J.; III, C. M. G.; Kane, R. R.; Pinney, K. G.; Prezioso, J. A.; Edvardsen, K. Functionalized Stilbene Derivatives as Improved Vascular Targeting Agents. U.S. Pat. No. 7,384,925B2, Jun. 10, 2008.

(32) Chen, Z.; Mocharla, V. P.; Farmer, J. M.; Pettit, G. R.; Hamel, E.; Pinney, K. G. Preparation of New Anti-Tubulin Ligands Through a Dual-Mode, Addition-Elimination Reaction to a Bromo-Substituted α,β-Unsaturated Sulfoxide. *J. Org. Chem.* 2000, 65 (25), 8811-8815. https://doi.org/10.1021/jo0004761.

(33) Pinney, K. G.; Bounds, A. D.; Dingeman, K. M.; Mocharla, V. P.; Pettit, G. R.; Bai, R.; Hamel, E. A New Anti-Tubulin Agent Containing the Benzo[b]Thiophene Ring System. *Bioorg. Med. Chem. Lett.* 1999, 9 (8), 1081-1086. https://doi.org/10.1016/S0960-894X(99)00143-2.

(34) Pinney, K.; Pettit, G.; Mocharla, V.; Mejia, M. del P.; Shirali, A. Anti-Mitotic Agents Which Inhibit Tubulin Polymerization. WO/1998/039323, Sep. 12, 1998.

(35) Pinney, K.; Sriram, M.; George, C.; Tanpure, R. Efficient Method for Preparing Functionalized Benzosuberenes. WO/2012/068284, May 25, 2012.

(36) Pinney, K.; Mocharla, V.; Chen, Z.; Garner, C.; Ghatak, A.; Hadimani, M.; Kessler, J.; Dorsey, J.; Edvardsen, K.; Chaplin, D.; Prezioso, J.; Ghatak, U. Tubulin Binding Agents and Corresponding Prodrug Constructs. US20040043969A1, Mar. 4, 2004.

(37) Tanpure, R. P.; George, C. S.; Strecker, T. E.; Devkota, L.; Tidmore, J. K.; Lin, C.-M.; Herdman, C. A.; MacDonough, M. T.; Sriram, M.; Chaplin, D. J.; Trawick, M. L.; Pinney, K. G. Synthesis of Structurally Diverse Benzosuberene Analogues and Their Biological Evaluation as Anti-Cancer Agents. *Bioorg. Med. Chem.* 2013, 21 (24), 8019-8032. https://doi.org/10.1016/j.bmc.2013.08.035.

(38) Tanpure, R. P.; George, C. S.; Sriram, M.; Strecker, T. E.; Tidmore, J. K.; Hamel, E.; Charlton-Sevcik, A. K.; Chaplin, D. J.; Trawick, M. L.; Pinney, K. G. An Amino-Benzosuberene Analogue That Inhibits Tubulin Assembly and Demonstrates Remarkable Cytotoxicity. *MedChemComm* 2012, 3 (6), 720-724. https://doi.org/10.1039/C2MD00318J.

(39) Hadimani, M. B.; MacDonough, M. T.; Ghatak, A.; Strecker, T. E.; Lopez, R.; Sriram, M.; Nguyen, B. L.; Hall, J. J.; Kessler, R. J.; Shirali, A. R.; Liu, L.; Garner, C. M.; Pettit, G. R.; Hamel, E.; Chaplin, D. J.; Mason, R. P.; Trawick, M. L.; Pinney, K. G. Synthesis of a 2-Aryl-3-Aroyl Indole Salt (OXi8007) Resembling Combretastatin A-4 with Application as a Vascular Disrupting Agent. *J. Nat. Prod.* 2013, 76 (9), 1668-1678. https://doi.org/10.1021/np400374w.

(40) Hamel, E. Antimitotic Natural Products and Their Interactions with Tubulin. *Med. Res. Rev.* 1996, 16 (2), 207-231. https://doi.org/10.1002/(SICI)1098-1128(199603)16:2<207::AID-MED4>3.0.CO;2-4.

(41) Wu, X.; Wang, Q.; Li, W. Recent Advances in Heterocyclic Tubulin Inhibitors Targeting the Colchicine Binding Site. *Anticancer Agents Med. Chem.* 2016, 16 (10), 1325-1338. https://doi.org/10.2174/1871520616666160219161921.

(42) Lee, R. M.; Gewirtz, D. A. Colchicine Site Inhibitors of Microtubule Integrity as Vascular Disrupting Agents. *Drug Dev. Res.* 2008, 69 (6), 352-358. https://doi.org/10.1002/ddr.20267.

(43) Gigant, B.; Cormier, A.; Dorléans, A.; Ravelli, R. B. G.; Knossow, M. Microtubule-Destabilizing Agents: Structural and Mechanistic Insights from the Interaction of Colchicine and Vinblastine with Tubulin. In *Tubulin-*

*Binding Agents: Synthetic, Structural and Mechanistic Insights*; Carlomagno, T., Ed.; Topics in Current Chemistry; Springer Berlin Heidelberg: Berlin, Heidelberg, 2009; pp 259-278. https://doi.org/10.1007/128_2008_11.

(44) Sackett, D. L. Podophyllotoxin, Steganacin and Combretastatin: Natural Products That Bind at the Colchicine Site of Tubulin. *Pharmacol. Ther.* 1993, 59 (2), 163-228. https://doi.org/10.1016/0163-7258(93)90044-E.

(45) Wang, Y.; Zhang, H.; Gigant, B.; Yu, Y.; Wu, Y.; Chen, X.; Lai, Q.; Yang, Z.; Chen, Q.; Yang, J. Structures of a Diverse Set of Colchicine Binding Site Inhibitors in Complex with Tubulin Provide a Rationale for Drug Discovery. *FEBS J.* 2016, 283 (1), 102-111. https://doi.org/10.1111/febs.13555.

(46) Ji, Y.-T.; Liu, Y.-N.; Liu, Z.-P. Tubulin Colchicine Binding Site Inhibitors as Vascular Disrupting Agents in Clinical Developments. *Curr. Med. Chem.* 2015, 22 (11), 1348-1360. https://doi.org/10.2174/0929867322666150114163732.

(47) Nguyen, T. L.; McGrath, C.; Hermone, A. R.; Burnett, J. C.; Zaharevitz, D. W.; Day, B. W.; Wipf, P.; Hamel, E.; Gussio, R. A Common Pharmacophore for a Diverse Set of Colchicine Site Inhibitors Using a Structure-Based Approach. *J. Med. Chem.* 2005, 48 (19), 6107-6116. https://doi.org/10.1021/jm050502t.

(48) Chen, J.; Liu, T.; Dong, X.; Hu, Y. Recent Development and SAR Analysis of Colchicine Binding Site Inhibitors. *Mini. Rev. Med. Chem.* 2009, 9 (10), 1174-1190. https://doi.org/info:doi/10.2174/138955709789055234.

(49) Lu, Y.; Chen, J.; Xiao, M.; Li, W.; Miller, D. D. An Overview of Tubulin Inhibitors That Interact with the Colchicine Binding Site. *Pharm. Res.* 2012, 29 (11), 2943-2971. https://doi.org/10.1007/s 11095-012-0828-z.

(50) Macdonough, M. T.; Strecker, T. E.; Hamel, E.; Hall, J. J.; Chaplin, D. J.; Trawick, M. L.; Pinney, K. G. Synthesis and Biological Evaluation of Indole-Based, Anti-Cancer Agents Inspired by the Vascular Disrupting Agent 2-(3'-Hydroxy-4'-Methoxyphenyl)-3-(3",4",5"-Trimethoxybenzoyl)-6-Methoxyindole (OXi8006). *Bioorg. Med. Chem.* 2013, 21 (21), 6831-6843. https://doi.org/10.1016/j.bmc.2013.07.028.

(51) Flynn, B. L.; Gill, G. S.; Grobelny, D. W.; Chaplin, J. H.; Paul, D.; Leske, A. F.; Lavranos, T. C.; Chalmers, D. K.; Charman, S. A.; Kostewicz, E.; Shackleford, D. M.; Morizzi, J.; Hamel, E.; Jung, M. K.; Kremmidiotis, G. Discovery of 7-Hydroxy-6-Methoxy-2-Methyl-3-(3,4,5-Trimethoxybenzoyl)Benzo[b]Furan (BNC105), a Tubulin Polymerization Inhibitor with Potent Antiproliferative and Tumor Vascular Disrupting Properties. *J. Med. Chem.* 2011, 54 (17), 6014-6027. https://doi.org/10.1021/jm200454y.

(52) Kuo, C.-C.; Hsieh, H.-P.; Pan, W.-Y.; Chen, C.-P.; Liou, J.-P.; Lee, S.-J.; Chang, Y.-L.; Chen, L.-T.; Chen, C.-T.; Chang, J.-Y. BPR0L075, a Novel Synthetic Indole Compound with Antimitotic Activity in Human Cancer Cells, Exerts Effective Antitumoral Activity in Vivo. *Cancer Res.* 2004, 64 (13), 4621-4628. https://doi.org/10.1158/0008-5472.CAN-03-3474.

(53) Liu, L.; Beck, H.; Wang, X.; Hsieh, H.-P.; Mason, R. P.; Liu, X. Tubulin-Destabilizing Agent BPR0L075 Induces Vascular-Disruption in Human Breast Cancer Mammary Fat Pad Xenografts. *PLOS ONE* 2012, 7 (8), e43314. https://doi.org/10.1371/journal.pone.0043314.

(54) Rasolofonjatovo, E.; Provot, O.; Hamze, A.; Rodrigo, J.; Bignon, J.; Wdzieczak-Bakala, J.; Desravines, D.; Dubois, J.; Brion, J.-D.; Alami, M. Conformationally Restricted Naphthalene Derivatives Type Isocombretastatin A-4 and Isoerianin Analogues: Synthesis, Cytotoxicity and Antitubulin Activity. *Eur. J. Med. Chem.* 2012, 52, 22-32. https://doi.org/10.1016/j.ejmech.2012.03.001.

(55) Rasolofonjatovo, E.; Provot, O.; Hamze, A.; Rodrigo, J.; Bignon, J.; Wdzieczak-Bakala, J.; Lenoir, C.; Desravines, D.; Dubois, J.; Brion, J.-D.; Alami, M. Design, Synthesis and Anticancer Properties of 5-Arylbenzoxepins as Conformationally Restricted Isocombretastatin A-4 Analogs. *Eur. J. Med. Chem.* 2013, 62, 28-39. https://doi.org/10.1016/j.ejmech.2012.12.042.

(56) Chen, Z.; O'Donnell, C. J.; Maderna, A. Synthesis of 3-Methoxy-9-(3,4,5-Trimethoxyphenyl)-6,7-Dihydro-5H-Benzo[7]Annulen-4-01, a Potent Antineoplastic Benzosuberene Derivative for Anti-Cancer Chemotherapy. *Tetrahedron Lett.* 2012, 53 (1), 64-66. https://doi.org/10.1016/j.tetlet.2011.10.145.

(57) Chen, Z.; Maderna, A.; Sukuru, S. C. K.; Wagenaar, M.; O'Donnell, C. J.; Lam, M.-H.; Musto, S.; Loganzo, F. New Cytotoxic Benzosuberene Analogs. Synthesis, Molecular Modeling and Biological Evaluation. *Bioorg. Med. Chem. Lett.* 2013, 23 (24), 6688-6694. https://doi.org/10.1016/j.bmcl.2013.10.039.

(58) Galli, U.; Travelli, C.; Aprile, S.; Arrigoni, E.; Torretta, S.; Grosa, G.; Massarotti, A.; Sorba, G.; Canonico, P. L.; Genazzani, A. A.; Tron, G. C. Design, Synthesis, and Biological Evaluation of Combretabenzodiazepines: A Novel Class of Anti-Tubulin Agents. *J. Med. Chem.* 2015, 58 (3), 1345-1357. https://doi.org/10.1021/jm5016389.

(59) Prileschajew Nikolaus. Oxydation Ungesittiger Verbindungen Mittels Organischer Superoxyde. *Berichte Dtsch. Chem. Ges.* 1909, 42 (4), 4811-4815. https://doi.org/10.1002/cber.190904204100.

(60) VanRheenen, V.; Kelly, R. C.; Cha, D. Y. An Improved Catalytic OsO4 Oxidation of Olefins to Cis-1,2-Glycols Using Tertiary Amine Oxides as the Oxidant. *Tetrahedron Lett.* 1976, 17 (23), 1973-1976. https://doi.org/10.1016/S0040-4039(00)78093-2.

(61) Gustowski, D. A.; Delgado, M.; Gatto, V. J.; Echegoyen, L.; Gokel, G. W. Electrochemical Switching in Anthraquinone-Substituted Carbon-Pivot Lariat Ethers and Podands: Chain Length Effects in Geometric and Electronic Cooperativity. *J. Am. Chem. Soc.* 1986, 108 (24), 7553-7560. https://doi.org/10.1021/ja00284a019.

(62) Sandmeyer Traugott. Ueber Die Ersetzung Der Amidgruppe Durch Chlor in Den Aromatischen Substanzen. *Berichte Dtsch. Chem. Ges.* 2006, 17 (2), 1633-1635. https://doi.org/10.1002/cber.18840170219.

(63) Sandmeyer Traugott. Ueber Die Ersetzung Der Amidgruppe Durch Chlor, Brom Und Cyan in Den Aromatischen Substanzen. *Berichte Dtsch. Chem. Ges.* 2006, 17 (2), 2650-2653. https://doi.org/10.1002/cber.188401702202.

(64) Mori, A.; Mizusaki, T.; Miyakawa, Y.; Ohashi, E.; Haga, T.; Maegawa, T.; Monguchi, Y.; Sajiki, H. Chemoselective Hydrogenation Method Catalyzed by Pd/C Using Diphenylsulfide as a Reasonable Catalyst Poison. *Tetrahedron* 2006, 62 (51), 11925-11932. https://doi.org/10.1016/j.tet.2006.09.094.

(65) E. Eaton, P.; R. Carlson, G.; T. Lee, J. Phosphorus Pentoxide-Methanesulfonic Acid. Convenient Alternative to Polyphosphoric Acid. *J. Org. Chem.* 1973, 38, 4071-4073. https://doi.org/10.1021/jo00987a028.

(66) Tanis, V. M.; Moya, C.; Jacobs, R. S.; Little, R. D. Synthesis and Evaluation of the Bioactivity of Simplified Analogs of the Seco-Pseudopterosins; Progress Toward Determining a Pharmacophore. *Tetrahedron* 2008, 64 (47), 10649-10663. https://doi.org/10.1016/j.tet.2008.09.025.

(67) Lin, W.; Wang, Q.; Xiao, Y.; He, H.; Zheng; Chen, X.; Chen, S.; WuXi AppTec. Fast Synthetic Route for 3-Aryl Substituted Propanoic Acid. China, CN 101747171 A, Dec. 17, 2008.

(68) Benner Andre; Bonifazi Alessandro; Shirataki Chikako; Temme Louisa; Schepmann Dirk; Quaglia Wilma; Shoji Osami; Watanabe Yoshihito; Daniliuc Constantin; Wünsch Bernhard. GluN2B-Selective N-Methyl-d-aspartate (NMDA) Receptor Antagonists Derived from 3-Benzazepines: Synthesis and Pharmacological Evaluation of Benzo[7]Annulen-7-amines. *ChemMedChem* 2014, 9 (4), 741-751. https://doi.org/10.1002/cmdc.201300547.

(69) Walsh, J. J.; Sha, R.; McCormack, E. M.; Hudson, G. J.; White, M.; Stack, G. D.; Moran, B. W.; Coogan, A.; Breen, E. C. Tubulin Binding Agents. US20150018566A1, Aug. 27, 2012.

(70) Gilman, H.; Jones, R. G.; Woods, L. A. The Preparation of Methylcopper and Some Observations on the Decomposition of Organocopper Compounds. *J. Org. Chem.* 1952, 17 (12), 1630-1634. https://doi.org/10.1021/jo50012a009.

(71) Hua, J.; Sheng, Y.; Pinney, K. G.; Garner, C. M.; Kane, R. R.; Prezioso, J. A.; Pettit, G. R.; Chaplin, D. J.; Edvardsen, K. Oxi4503, a Novel Vascular Targeting Agent: Effects on Blood Flow and Antitumor Activity in Comparison to Combretastatin A-4 Phosphate. *Anticancer Res.* 2003, 23 (2B), 1433-1440.

(72) Benham, F. J.; Fogh, J.; Harris, H. Alkaline Phosphatase Expression in Human Cell Lines Derived from Various Malignancies. *Int. J. Cancer* 1981, 27 (5), 637-644.

(73) Rao, S. R.; Snaith, A. E.; Marino, D.; Cheng, X.; Lwin, S. T.; Orriss, I. R.; Hamdy, F. C.; Edwards, C. M. Tumour-Derived Alkaline Phosphatase Regulates Tumour Growth, Epithelial Plasticity and Disease-Free Survival in Metastatic Prostate Cancer. *Br. J. Cancer* 2017, 116 (2), 227-236. https://doi.org/10.10.38/bjc.2016.402.

(74) Gangjee, A.; Zhao, Y.; Lin, L.; Raghavan, S.; Roberts, E. G.; Risinger, A. L.; Hamel, E.; Mooberry, S. L. Synthesis and Discovery of Water Soluble Microtubule Targeting Agents That Bind to the Colchicine Site on Tubulin and Circumvent Pgp Mediated Resistance. *J. Med. Chem.* 2010, 53 (22), 8116-8128. https://doi.org/10.1021/jm101010n.

(75) Maguire, C. J.; Chen, Z.; Mocharla, V. P.; Sriram, M.; Strecker, T. E.; Hamel, E.; Zhou, H.; Lopez, R.; Wang, Y.; Mason, R. P.; Chaplin, D. J.; Trawick, M. L.; Pinney, K. G. Synthesis of Dihydronaphthalene Analogues Inspired by Combretastatin A-4 and Their Biological Evaluation as Anticancer Agents. *MedChemComm.* 2018, 9 (10), 1649-1662. https://doi.org/10.1039/C8MD00322J.

(76) Folaron, M.; Seshadri, M. Bioluminescence and MR Imaging of the Safety and Efficacy of Vascular Disruption in Gliomas. *Mol. Imaging Biol. MIB Off Publ. Acad. Mol. Imaging* 2016, 18 (6), 860-869. https://doi.org/10.1007/s11307-016-0963-8.

(77) Tumati, V.; Mathur, S.; Song, K.; Hsieh, J.-T.; Zhao, D.; Takahashi, M.; Dobin, T.; Gandee, L.; Solberg, T. D.; Habib, A. A.; Saha, D. Development of a Locally Advanced Orthotopic Prostate Tumor Model in Rats for Assessment of Combined Modality Therapy. *Int. J. Oncol.* 2013, 42 (5), 1613-1619. https://doi.org/10.3892/ijo.2013.1858.

(78) Zhao, D.; Richer, E.; Antich, P. P.; Mason, R. P. Antivascular Effects of Combretastatin A4 Phosphate in Breast Cancer Xenograft Assessed Using Dynamic Bioluminescence Imaging and Confirmed by MRI. *FASEB J. Off Publ. Fed. Am. Soc. Exp. Biol.* 2008, 22 (7), 2445-2451. https://doi.org/10.1096/fj.07-103713.

(79) Zhao, D.; Jiang, L.; Hahn, E. W.; Mason, R. P. Tumor Physiologic Response to Combretastatin A4 Phosphate Assessed by MRI. *Int. J. Radiat. Oncol. Biol. Phys.* 2005, 62 (3), 872-880. https://doi.org/10.1016/j.ijrobp.2005.03.009.

(80) Zhao, D.; Chang, C.-H.; Kim, J. G.; Liu, H.; Mason, R. P. In Vivo Near-Infrared Spectroscopy and Magnetic Resonance Imaging Monitoring of Tumor Response to Combretastatin A-4-Phosphate Correlated with Therapeutic Outcome. *Int. J. Radiat. Oncol. Biol. Phys.* 2011, 80 (2), 574-581. https://doi.org/10.1016/j.ijrobp.2010.12.028.

(81) Galbraith, S. M.; Maxwell, R. J.; Lodge, M. A.; Tozer, G. M.; Wilson, J.; Taylor, N. J.; Stirling, J. J.; Sena, L.; Padhani, A. R.; Rustin, G. J. S. Combretastatin A4 Phosphate Has Tumor Antivascular Activity in Rat and Man as Demonstrated by Dynamic Magnetic Resonance Imaging. *J. Clin. Oncol. Off J. Am. Soc. Clin. Oncol.* 2003, 21 (15), 2831-2842. https://doi.org/10.1200/JCO.2003.05.187.

(82) Vichai, V.; Kirtikara, K. Sulforhodamine B Colorimetric Assay for Cytotoxicity Screening. *Nat. Protoc.* 2006, 1 (3), 1112-1116. https://doi.org/10.1038/nprot.2006.179.

(83) Monks, A.; Scudiero, D.; Skehan, P.; Shoemaker, R.; Paull, K.; Vistica, D.; Hose, C.; Langley, J.; Cronise, P.; Vaigro-Wolff, A.; Gray-Goodrich, M.; Campbell, H.; Mayo, J.; Boyd, M. Feasibility of a High-Flux Anticancer Drug Screen Using a Diverse Panel of Cultured Human Tumor Cell Lines. *JNCI J. Natl. Cancer Inst.* 1991, 83 (11), 757-766. https://doi.org/10.1093/jnci/83.11.757.

(84) Hamel, E.; Lin, C. M. Stabilization of the Colchicine-Binding Activity of Tubulin by Organic Acids. *Biochim. Biophys. Acta BBA—Gen. Subj.* 1981, 675 (2), 226-231. https://doi.org/10.1016/0304-4165(81)90231-2.

(85) Hamel, E. Evaluation of Antimitotic Agents by Quantitative Comparisons of Their Effects on the Polymerization of Purified Tubulin. *Cell Biochem. Biophys.* 2003, 38 (1), 1-22. https://doi.org/10.1385/CBB:38:1:1.

What is claimed is:

1. A compound of formula:

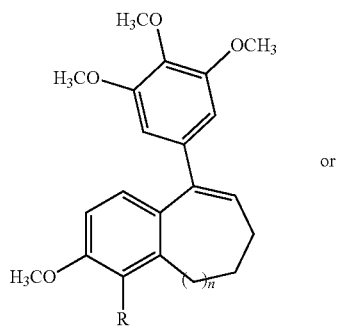

or

-continued

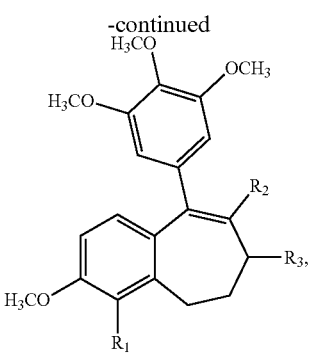

or a pharmacologically acceptable salt thereof, wherein
R is $CH_3$, $(CH_2)_3CH_3$, $O(CH_2)_2O(CH_2)_2OCH_3$, $O(CH_2)_2OH$, COOEt, $CH_2OH$, CN, or CHO,
n is 0 or 1, and wherein $R_1$, $R_2$, and $R_3$ are selected from one of the following combinations: (a) Ri is $CH_3$, $R_2$ is Br, and $R_3$ is H, (b) $R_1$ is OH, $R_2$ is Br, and $R_3$ is H, and (c) $R_1$ is $OCH_3$, $R_2$ is H, and $R_3$ is OH.

2. The compound of claim 1, wherein R is $CH_3$, $(CH_2)_3CH_3$, $O(CH_2)_2O(CH_2)_2OCH_3$, $O(CH_2)_2OH$, COOEt, $CH_2OH$, CN, or CHO, n is 1.

3. A pharmaceutical formulation comprising a therapeutically effective amount of the compound of claim 1.

4. A method for inhibiting tubulin polymerization and disrupting vascularization in a tumor in a patient, comprising administering the pharmaceutical formulation of claim 3.

5. A compound of formula:

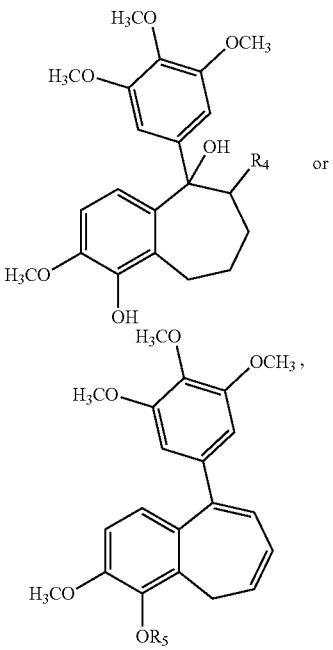

or a pharmacologically acceptable salt thereof, wherein
$R_4$ is H, OH, or (=O), and
$R_5$ is $PO(ONa)_2$.

6. The compound of claim 5, wherein $R_4$ is (=O).

7. A pharmaceutical formulation comprising a therapeutically effective amount of the compound of claim 5.

8. A method for inhibiting tubulin polymerization and disrupting vascularization in a tumor in a patient, comprising administering the pharmaceutical formulation of claim 7.

9. A compound of formula:

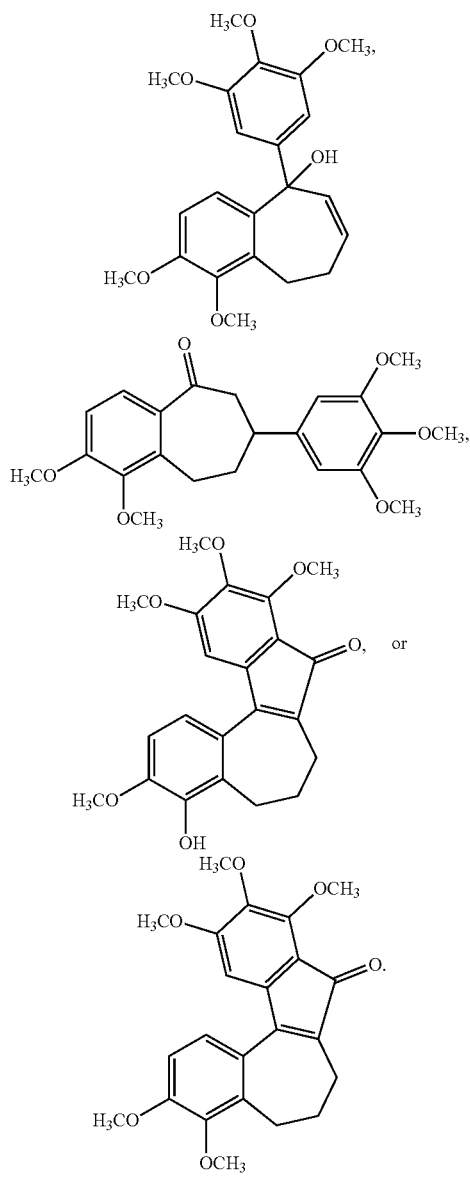

or a pharmacologically acceptable salt thereof.

10. A pharmaceutical formulation comprising a therapeutically effective amount of the compound of claim 9.

11. A method for inhibiting tubulin polymerization and disrupting vascularization in a tumor in a patient, comprising administering the pharmaceutical formulation of claim 10.

* * * * *